US007465561B2

(12) United States Patent
Gupta et al.

(10) Patent No.: US 7,465,561 B2
(45) Date of Patent: Dec. 16, 2008

(54) PROBES AND METHODS FOR HEPATITIS C VIRUS TYPING USING SINGLE PROBE ANALYSIS

(75) Inventors: Amar P. Gupta, Danville, CA (US); Stephen Gordon Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 11/474,125

(22) Filed: Jun. 23, 2006

(65) Prior Publication Data

US 2007/0020665 A1  Jan. 25, 2007

Related U.S. Application Data

(60) Provisional application No. 60/695,991, filed on Jun. 30, 2005, provisional application No. 60/696,253, filed on Jun. 30, 2005, provisional application No. 60/696,293, filed on Jun. 30, 2005, provisional application No. 60/696,303, filed on Jun. 30, 2005.

(51) Int. Cl.
  *C12P 19/34* (2006.01)
  *C12Q 1/68* (2006.01)
(52) U.S. Cl. .................... 435/91.2; 435/91.21; 435/6
(58) Field of Classification Search ............... 435/91.2
  See application file for complete search history.

(56) References Cited

U.S. PATENT DOCUMENTS

| 5,527,669 | A | 6/1996 | Resnick et al. |
| 5,580,718 | A | 12/1996 | Resnick et al. |
| 5,837,442 | A | 11/1998 | Tsang |
| 5,882,852 | A | 3/1999 | Bukh et al. |
| 6,140,054 | A | 10/2000 | Wittwer et al. |
| 6,548,244 | B2 | 4/2003 | Maertens et al. |
| 2003/0054372 | A1* | 3/2003 | Jaeger ............... 435/6 |
| 2003/0152591 | A1 | 8/2003 | Sablon et al. |
| 2004/0229253 | A1 | 11/2004 | Hyldig-Nielsen et al. |
| 2005/0079490 | A1 | 4/2005 | Stuber et al. |

FOREIGN PATENT DOCUMENTS

| EP | 0 529 493 A2 | 8/1992 |
| EP | 0 529 493 B1 | 3/1993 |
| EP | 06013306.3 | 5/2007 |
| JP | 2002272475 | 9/2002 |
| WO | WO 94/25601 A2 | 11/1994 |
| WO | WO 96/13590 A2 | 5/1996 |
| WO | WO 99/28500 A1 | 6/1999 |
| WO | WO 01/46469 A1 | 6/2001 |
| WO | WO 02/083948 A1 | 10/2002 |
| WO | WO 2003/057910 A2 | 7/2003 |
| WO | WO 2004/014313 A2 | 2/2004 |
| WO | WO 2004/033726 A1 | 4/2004 |
| WO | WO 2004/044182 A2 | 5/2004 |
| WO | WO 2004/074447 A2 | 5/2004 |
| WO | WO 2005/028650 A2 | 3/2005 |

OTHER PUBLICATIONS

Mackay et al. Nucleic acids research, vol. 30, No. 6, pp. 1292-1305, 2002.*
Schuttler et al. Journal of Clinical Microbiology, vol. 42, No. 5, pp. 1977-1981, May 2004.*
Andonov, A., et al, 1995, "Subtyping of hepatitis C Virus Isolates by a Line Probe Assay Using Hybridization", *Journal of Clinical Microbiology*, vol. 33 (1): 254-256.
Bean, P., et al, "Molecular principles underlying hepatitis C virus diagnosis", *American Clinical Laboratory*, Viral Hepatitis Series, 19-21.
Bukh, J., et al, 1993, "At least 12 genotypes of hepatitis C virus predictied by sequence analysis of the putative E1 gene of isolates collected worldwide", *Proc. Natl. Acad. Sci. USA*, vol. 90: 8234-8238.
Bullock, G., et al, 2002, "Hepatitis C Genotype Determination by Melting curve Analysis with a Single Set of Fluorescence Resonance Energy Transfer Probes", *Clinical Chemistry*, 48: 12, 2147-2154.
Comanor, L., et al, 2003, "Hepatitis C virus RNA tests: performance attributes and their impact on clinical utility", *Expert Rev. Mol. Diagn.*, 3(6): 689-702.
Corbet, S., et al, 2003, "Hepatitis C Virus Subtyping by a Core-Envelope 1-Based Reverse Transcriptase PCR Assay with Sequencing and Its Use in Determining Subtype Distribution among Danish Patients", *Journal of Clinical Microbiology*, vol. 41 (3): 1091-1100.
Dufour, D., 2002, "Hepatitis C Laboratory Tests for Diagnosis and Monitoring of Infection", *Clinical Laboratory News*, 10-14.
Elahi, E., et al, 2003, "Determination of hepatitis C virus genotype by Pyrosequencing", *Journal of Virological Methods*, 109: 171-176.
Forns, X., et al, 2002, "The challenge of developing a vaccine against hepatitis C virus", *Journal of Hepatology*, 37: 684-695.
Gasbarro, R., et al, 1999, "Hepatitis C: new perspectives in diagnosis", *Schiff ER*, 1: 3-15.
Giannini, C., et al, 2003, "Hepatitis C virus biology", *Cell Death and Differentiation*, 10: S27-S53.
Haushofer, A., et al, 2003, "Genotyping of hepatitis C virus—comparison of three assays", *Jounal of Clinical Virology*, 27: 276-285.
Howard, C., 2002, "Hepatitis C virus: Clades and properties", *Journal of Gastroenterology and Hepatology*, 17: S468-S470.
Kalinina, O., et al, 2002 "A Natural Intergenotypic Recombinant of Hepatitis C Virus identified in St. Petersburg", *Journal of Virology*, vol. 76 (8): 4034-4043.

(Continued)

*Primary Examiner*—Kenneth R. Horlick
*Assistant Examiner*—Cynthia Wilder
(74) *Attorney, Agent, or Firm*—Olga Kay

(57) ABSTRACT

This invention provides compositions and methods for HCV typing, e.g., genotyping and/or subtyping. The compositions and methods of the invention can be used to assign an HCV isolate to one of at least five HCV genotypes (for example, selected from genotypes 1, 2, 3, 4, 5 or 6), or assign an HCV isolate to one of at least six subtypes (for example, selected from subtypes 1a/b/c, 2a/c, 2b, 3a, 4a, 5a or 6a), where the methods of the invention use only a single typing probe to make the HCV type assignment.

6 Claims, 24 Drawing Sheets

OTHER PUBLICATIONS

Kleiber, J., et al, 2000, "Performance Characteristics of a Quantitative, Homogeneous TaqMan RT-PCR Test for HCV RNA", *Journal of Molecular Diagnostics*, vol. 2 (3): 158-166.

Liew, M., et al, 2004, "Genotyping of Single-Nucleotide Polymorphisms by High-Resolution Melting of Small Amplicons", *Clinical Chemistry* 50:7 1156-1164.

Liew, M., et al, 2004, "Hepatitis C Genotyping by Denaturing High-Performance Liquid Chromatography", *Journal of Clinical Microbiology*, vol. 42 (1): 158-163.

Maertens, G., et al, 1997, "Genotypes and Genetic Variation of Hepatitis C Virus", *The Molecular Medicine of Viral Hepatitis*, 183-233.

Majid, A., et al, 2002, "Current and future hepatitis C virus diagnostic testing: problems and advancements", *Microbes and Infection*, 4: 1227-1236.

Mercado, J., et al, "Genotyping diversity of Hepatitis C virus in Brazilian patients".

Nolte, F., et al, 2003, "Clinical Evaluation of Two Methods for Genotyping Hepatitis C Virus Based on Analysis of the 5' Noncoding Region", *Journal of Clinical Microbiology*, vol. 41 (4): 1558-1564.

Nolte, F., 2001, "Hepatitis C Virus Genotyping: Clinical Implications and Methods", *Molecular Diagnosis*, vol. 6 (4): 265-277.

Otagiri, H., et al, 2002, "Evaluation of a new assay for hepatitis C virus genotyping and viral load determination in patients with chronic hepatitis C", *Journal of Virological Methods*, 103: 137-143.

Pawlotsky, J., 2003, "Hepatitis C virus genetic variability: pathogenic and clinical implications", *Journal Article*, vol. 7 (1): 1-16.

Pawlotsky, J., 2003, "Use and interpretation of hepatitis C virus diagnostic assays", *Journal Article*, vol. 7 (1): 1-10.

Poddar, S., 2000, "Symmetric vs asymmetric PCR and molecular beacon probe in the detection of a target gene of adenovirus", *Molecular and Cellular Probes*, 14: 25-32.

Podzorski, R., 2002, "Molecular Testing in the Diagnosis and management of Hepatitis C Virus Infection", *Arch Pathol Lab Med*, vol. 126: 285-290.

Raghuraman, S., et al, 2003, "Distrubution of the different genotypes of HCV among patients attending a tertiary care hospital in south India", *Journal of Clinical Virology*, 26: 61-69.

Raghuraman, S., et al, 2003, "Hepatitis C virus genotypes: special reference to the Indian scene", *Indian Journal of Gastronterology*, vol. 22: 181-186.

Ranasinghe, R., et al, 2001, "Linear fluorescent oligonucleotide probes with an acridine quencher generate a signal upon hybridization", *Chem. Commun.*, 1480-1481.

Reed, G., et al, 2004, "Sensitivity and Specificity of Single-Nucleotide Polymorphism Scanning by High-Resolution Melting Analysis", *Clinical Chemistry*, 50:10 1748-1754.

Richter, S., et al, 2002, "Laboratory Assays for Diagnosis and Management of Hepatitis C Virus Infection", *Journal of Clinical Microbiology*, vol. 40 (12): 4407-4412.

Robertson, B., et al, 1998, "Classification, nomenclature, and database development for hepatitis C virus (HCV) and related viruses: proposals for standardization", *Arch Virol*, 143/12 2493-2503.

Ross, R., et al, 2000, "Genotyping of Hepatitis C Virus Isolates using CLIP Sequencing", *Journal of Clinical Microbiology*, 3581-3584.

Sandres-Suané, K., et al, "Determining hepatitis C genotype by analyzing the sequence of the NS5b region", *Journal of Virological Methods*, 109 187-193.

Schröter, M., et al, 2002, "Genotyping of Hepatitis C Virus Types 1, 2, 3, and 4 by a One=Step LightCycler Method Using Three Different Pairs of Hybridization Probes", *Journal of Clinical Microbiology*, vol. 40(6) 2046-2050.

Schröter, M., et al, 2001, "Quantitative Detection of Hepatitis C Virus RNA by Light Cycler PCR and Comparison with Two Different PCR Assays", *Journal of Clinical Microbiology*, vol. 39 (2): 765-768.

Sebastian, J., et al, 2003, "HCV Genotyping Using Real-Time PCR Assay", *Associaton for Molecular Pathology Annual Mtg.*, Poster.

Selvin, P., 2000, "The renaissance of fluorescence resonance energy transfer", *Nature Structura Biology*, vol. 7 (9): 730-734.

Stuyver, L., et al, 1994, "Classificatio of hepatitis C viruses based on phylogenetic analysis of the envelope 1 and nonstructural 5B regions and identification of five additional subtypes", *Proc. Natl. Acad. Sci. USA*, vol. 91 10134-10138.

Stuyver, L., et al, 2000, "Line Probe Assay for Monitoring drug Resistance in Hepatitis B Virus-Infected patients during Antiviral Therapy", *Journal of Clinical Microbiology*, vol. 38 (2): 702-707.

Stuyver, L., et al, 1996, "Second-Generation Line Probe Assay for Hepatitis C Virus Genotyping", *Journal of Clinical Microbiology*, vol. 34 (9): 2259-2266.

Stuyver, L., et al, 1993, "Typing of hepatitis C virus isolates and characterization of new subtypes using a line probe assay", *Journal of General Virology*, 74 : 1093-1102.

Simmonds, p., et al, 1994, "A Proposed System for the Nomenclature of Hepatitis C Viral Genotypes", *Hepatology*, 1321-1324.

Simmonds, P., et al, 1993, "Classification of hepatitis C virus into six major genotypes and a series of subtypes by phylogenetic analysis of the NS-5 region", *Journal of General Virology*, 74: 2391-2399.

Simmonds, P., et al, 1994, "Identification of genotypes of hepatitis C virus by sequence comparisons in the core, E1 and NS-5 regions", *Journal of General Virology*, 75: 1053-1061.

Simmonds, P., 1999, "Viral Heterogeneity of the Hepatitis C Virus", *Journal of Hepatology*, 31: 54-60.

Zein, N., 2000, "Clinical Significance of Hepatitis C Virus Genotypes", *Clinical Microbiology Reviews*, vol. 13 (2): 223-235.

Zhou, L., et al, 2004, "Closed-Tube Genotyping with Unlabled Oligonucleotide Probes and a Saturating DNA Dye", *Clinical Chemistry*, 50:8 1328-1335.

Zhou, L., et al, 2003, "High-resolution DNA melting curve analysis to establish HLA genotypic identity", *Tissue Antigens*, 64: 156-164.

Van Brussel, M., et al, "Identification of new type-specific patterns with the VERSANT™ HCV Genotype Assay (LiPA)".

Lau, J, et al., 1996, "Distribution of Hepatitis C Virus Genotypes Determined by Line Probe Assay in Patients with Chronic Hepatitis C Seen at Tertiary Referral Centers in the United States", *Annals of Internal Medicine*, 124(10) : 868-876.

Martin, P., 1995, "Hepatitis C Genotypes. The Key to Pathogenicity?", *Annals of Internal Medicine*, 122(3) : 227-228.

Hepatitis-Central.com, www.hepatitis-central.com, "Genetic Variation and HCV Genotyping".

Bullock, G., 2002, Hepatitis C Genotype Determination by melting Curve analysis with a single set of fluorescence resonance energy transfer probes, *Clinical Chemistry*, 48 (12): 2147-2154.

Jan, N., et al., 1991, Phagocytosis of Opsonised Fluorescent Platelets by Neutrophils to Detect Antiplatelet Antibody, *Comparative Haematology International*, 1:77-82.

Stuyver, L., et al., 1996, Second-Generation Line Probe Assay for Hepatitis C Virus Genotyping, *Journal of Clinical Microbiology*, 34 (9): 2046-2266.

Castelain, S. et al., 2004, "TaqMan amplificaiton system with an internal positive control for HCV RNA quantitation." *Journal of Clinical Virology.*, 31: 227-234.

Barbeau, J. et al., 2004, "Performance charcaterisitcs of a quantitative TaqMan Hep. C virus RNA analyte-specific reagent." *Journal of Clinical Virology*, 42:3739-3746.

Caliendo, A. et al., 2006, "Multilaboratory comparison of Hepatitis C virus viral load assays." *Journal of Clinical Virology*, 44:1726-1732.

Lindh, M. et al., 2005, "Genotyping of hepatitis c virus by TaqMan real-time PCR." *Journal of Clinical Virology*, 34:108-114.

Rolfe, K. et al., 2005, "A real-time TaqMan method for hepatitis C virus genotyping." *Journal of Clinical Virology.* 34:115-121.

* cited by examiner

| Genomic Heterogeneity Terminology | Definition | Percent Nucleotide Sequence Identity Over the Full HCV Genome |
|---|---|---|
| Genotype | Genetic heterogeneity among different HCV isolates | 65.7–68.9 % |
| Subtype | Closely related isolates within each of the major genotypes | 76.9–80.1 % |
| Quasispecies | Complex of genetic variants within individual isolates | 90.8–99 % |

| Subtype | Percent nucleotide identity with a 222-nucleotide segment derived from the NS5 region at positions 7975 to 8196 of the prototype HCV viral genome | | | | | | | | | | |
|---|---|---|---|---|---|---|---|---|---|---|---|
| | 1a | 1b | 1c | 2a | 2b | 2c | 3a | 3b | 4a | 5a | 6a |
| 1a | 100 | 81 | 85 | 65 | 66 | 63 | 67 | 66 | 68 | 69 | 64 |
| 1b | | 100 | 77 | 64 | 67 | 64 | 67 | 71 | 64 | 70 | 65 |
| 1c | | | 100 | 68 | 70 | 67 | 65 | 70 | 64 | 61 | 61 |
| 2a | | | | 100 | 82 | 77 | 67 | 67 | 66 | 66 | 68 |
| 2b | | | | | 100 | 81 | 64 | 69 | 65 | 67 | 66 |
| 2c | | | | | | 100 | 64 | 65 | 65 | 66 | 65 |
| 3a | | | | | | | 100 | 79 | 65 | 67 | 64 |
| 3b | | | | | | | | 100 | 66 | 68 | 61 |
| 4a | | | | | | | | | 100 | 66 | 66 |
| 5a | | | | | | | | | | 100 | 68 |
| 6a | | | | | | | | | | | 100 |

FIG. 4

| HCV Genotype/Subtype | Known Isolates |
|---|---|
| 1a | HCV-1, HCV-H, HC-J1 |
| 1b | HCV-J, HCV-BK, HCV-JT |
| 1c | HC-G9, Td-6, YS-117 |
| 2a | HC-J6, HC-J5, HCV-K2a |
| 2b | HC-J8, HC-J7, HCV-K2b |
| 2c | CH114, S83, T-983 |
| 3a | NZL1, E-b1, BR36, K3a/650, HCV-K3a, T-1, T-7 |
| 3b | NE137, HCV-Tr, T9, MN6, T-10 |
| 4a | GB809-4, Z4, Z8, Z5, Syr1, Syr2, N5, Cam600, Z1, N1, N2, DK13 |
| 5a | BE95, SA1, SA-7 |
| 6a | VN11, HK2, HK-2, VN506 |

| HCV Type | 5′-UTR Consensus Base Sequence | SEQ ID NO: |
|---|---|---|
| 1a/1b/1c | TGAGTACACC GGAATTGCCA GGACGACCGG GTC | 1 |
| 2a/2c | ---------- --------G ---A---T-- --- | 2 |
| 2b | ---------- ------A--G -A-A---T-- --- | 3 |
| 3a | ---------- -----C--TG --GT----- --- | 4 |
| 4a | ---------- -----C---G ---T------ --- | 5 |
| 5a | ---------- --------G ---T------ --- | 6 |
| 6a | ---------- ---------- ---T------ --- | 7 |
| 2a variant quasispecies | ---------- --------TG ---A---T-- --- | 42 |

FIG. 5

| Functional Probes | length (nt) | Base sequence | SEQ ID NO: |
|---|---|---|---|
| AG0203A | 21 | FCGGAATTGCCAGGACGACCGGP | 8 |
| AG0303B | 21 | FJCGGAATTGCCAGGACGACCGG | 9 |
| AG0503D | 24 | FCACCGGAATTGCCAGGACGACCGG | 10 |
| AG0503E | 22 | FCGGAATTGCCAGGACGACCGGG | 11 |
| AG0503F | 23 | FCGGAATTGCCAGGACGACCGGGT | 12 |
| AG0307D | 21 | FDGGAASSGDDAGGADGADDGGP | 13 |
| AG0307M | 22 | FCGGAATTGCCAGGACGACCGGGP | 14 |
| AG0307N | 22 | FDGGAASSGDDAGGADGADDGGGP | 15 |
| AG0308F | 25 | FGTACACCGGAATTGCCAGGACGACCP | 16 |
| AG0308L | 24 | FGTACACCGGAATTGCCAGGACGACP | 17 |
| AG0308Q | 23 | FACACCGGAATTGCCAGGACGACCP | 18 |
| AG0308R | 22 | FCACCGGAATTGCCAGGACGACCP | 19 |
| AG0308T | 26 | FAGTACACCGGAATTGCCAGGACGACCP | 20 |
| AG0308U | 27 | FGAGTACACCGGAATTGCCAGGACGACCP | 21 |
| AG0308V | 28 | FTGAGTACACCGGAATTGCCAGGACGACCP | 22 |
| AG0308W | 26 | FGTACACCGGAATTGCCAGGACGACCGP | 23 |
| AG0308X | 27 | FGTACACCGGAATTGCCAGGACGACCGGP | 24 |
| AG0308Y | 28 | FGTACACCGGAATTGCCAGGACGACCGGGP | 25 |
| AG0308Z | 27 | FAGTACACCGGAATTGCCAGGACGACCGP | 26 |
| AG0308AB | 25 | FAGTACACCGGAATTGCCAGGACGACP | 27 |
| Non-Functional Probes | | | |
| AG0308M | 23 | FGTACACCGGAATTGCCAGGACGAP | 28 |
| AG0308N | 22 | FGTACACCGGAATTGCCAGGACGP | 29 |
| AG0308P | 24 | FTACACCGGAATTGCCAGGACGACCP | 30 |
| AG0503G | 24 | FCGGAATTGCCAGGACGACCGGGTC | 31 |
| AG0503H | 23 | FCCGGAATTGCCAGGACGACCGGG | 32 |
| F= 6-carboxy-fluorescein (FAM); P=3'-terminal phosphate group/enzymatically blocked; J=acridine; S=5-propynyl-dU; D=5-Me-dC | | | |

| Functional Probe | Experimentally Observed T$_m$ (°C) | | | | | | Predicted T$_m$ (°C) | | | | | |
|---|---|---|---|---|---|---|---|---|---|---|---|---|
| | 1a/b | 2a/c | 3a | 4a | 5a | 6a | 1a/b | 2a/c | 2b | 3a | 4a | 5a | 6a |
| AG0203A | 61.5/60.5 | 37.0 | 34.5 | 43.0 | 48.5 | 54.7 | 70.4 | 46.3 | 44.1 | 41.5 | 52.0 | 56.7 | 64.1 |
| AG0503D | 63.5 | 44.0 | 42.5 | 52.0 | 54.5 | 58.3 | 82.2 | 66.8 | 60.8 | 60.1 | 70.8 | 73.7 | 78.8 |
| AG0503E | 63.0/62.0 | 39.0 | 36.5 | 47.5 | 51.5 | 56.7 | 82.6 | 62.0 | 58.5 | 57.6 | 69.2 | 72.6 | 78.2 |
| AG0503F | 63.5 | 41.5 | 39.5 | 49.0 | 53.0 | 57.0 | 83.3 | 63.9 | 60.2 | 59.4 | 71.0 | 74.2 | 79.6 |
| Non-Functional Probes | | | | | | | | | | | | | |
| AG0503G | 65.0 | 43.5 | 43.5 | 51.4 | 54.8 | 58.5 | 83.1 | 64.5 | 60.9 | 60.3 | 71.0 | 74 | 79.1 |
| AG0503H | 64.5 | 45.5 | 45.5 | 51.5 | 54.5 | 58.5 | 83.7 | 64.5 | 60.9 | 60.1 | 71.3 | 74.4 | 79.6 |
| All Experimental Samples contained 25 μg/mL New Methylene Blue Soluble Quencher | | | | | | | | | | | | | |

THIONIN
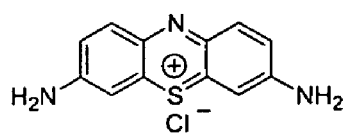
AZURE C
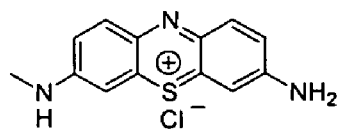
AZURE A
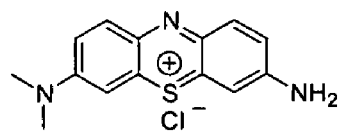
AZURE B
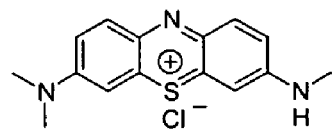
SYM-DIMETHYLTHIONIN
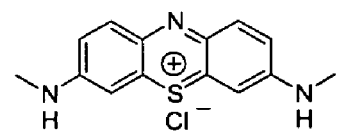
METHYLENE VIOLET BERNTHSEN
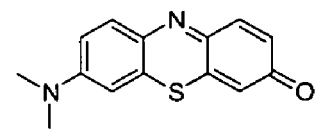
METHYLENE BLUE
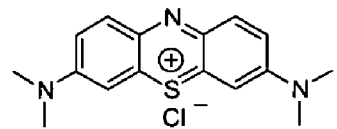
1,9-DIMETHYLMETHYLENE BLUE
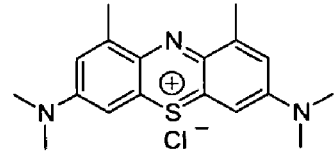
NEW METHYLENE BLUE
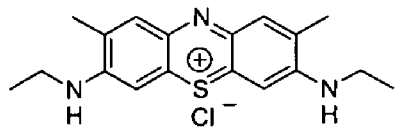
TOLUIDINE BLUE O
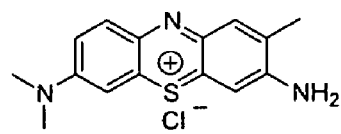
METHYLENE GREEN
FIG. 8

SEQUENCE LISTING

<160> NUMBER OF SEQ ID NOS: 42

<210> SEQ ID NO 1
<211> LENGTH: 33
<212> TYPE: DNA
<213> ORGANISM: hepatitis C virus

<400> SEQUENCE: 1
tgagtacacc ggaattgcca ggacgaccgg gtc          33

<210> SEQ ID NO 2
<211> LENGTH: 33
<212> TYPE: DNA
<213> ORGANISM: hepatitis C virus

<400> SEQUENCE: 2
tgagtacacc ggaattgccg ggaagactgg gtc          33

<210> SEQ ID NO 3
<211> LENGTH: 33
<212> TYPE: DNA
<213> ORGANISM: hepatitis C virus

<400> SEQUENCE: 3
tgagtacacc ggaattaccg gaaagactgg gtc          33

```
<210> SEQ ID NO 4
<211> LENGTH: 33
<212> TYPE: DNA
<213> ORGANISM: hepatitis C virus

<400> SEQUENCE: 4
tgagtacacc ggaatcgctg gggtgaccgg gtc                                33

<210> SEQ ID NO 5
<211> LENGTH: 33
<212> TYPE: DNA
<213> ORGANISM: hepatitis C virus

<400> SEQUENCE: 5
tgagtacacc ggaatcgccg ggatgaccgg gtc                                33

<210> SEQ ID NO 6
<211> LENGTH: 33
<212> TYPE: DNA
<213> ORGANISM: hepatitis C virus

<400> SEQUENCE: 6
tgagtacacc ggaattgccg ggatgaccgg gtc                                33

<210> SEQ ID NO 7
<211> LENGTH: 33
<212> TYPE: DNA
<213> ORGANISM: hepatitis C virus

<400> SEQUENCE: 7
tgagtacacc ggaattgcca ggatgaccgg gtc                                33

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (21)..(21)
<223> OTHER INFORMATION: n is dG 3'-modified with terminal phosphate
      group

<400> SEQUENCE: 8
nggaattgcc aggacgaccg n                                             21

<210> SEQ ID NO 9
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with acridine modified with
      6-carboxy-fluorescein

<400> SEQUENCE: 9
ncggaattgc caggacgacc gg                                            22

<210> SEQ ID NO 10
```

```
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM

<400> SEQUENCE: 10
naccggaatt gccaggacga ccgg                                              24

<210> SEQ ID NO 11
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM

<400> SEQUENCE: 11
nggaattgcc aggacgaccg gg                                                22

<210> SEQ ID NO 12
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM

<400> SEQUENCE: 12
nggaattgcc aggacgaccg ggt                                               23

<210> SEQ ID NO 13
<211> LENGTH: 21
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 5-Me-dC modified with 6-carboxy-
      fluorescein
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(19)
<223> OTHER INFORMATION: n is 5-Me-dC
<220> FEATURE:
<221> NAME/KEY: misc_feature
<222> LOCATION: (21)..(21)
<223> OTHER INFORMATION: n is dG 3'-modified with terminal phosphate
      group
```

-continued

```
<400> SEQUENCE: 13
nggaanngnn agganganng n                                              21

<210> SEQ ID NO 14
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (22)..(22)
<223> OTHER INFORMATION: n is dG 3'-modified with terminal phosphate
      group

<400> SEQUENCE: 14
nggaattgcc aggacgaccg gn                                             22

<210> SEQ ID NO 15
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is 5-Me-dC modified with 6-carboxy-
      fluorescein
<220> FEATURE:
<221> NAME/KEY: misc_feature
<222> LOCATION: (6)..(7)
<223> OTHER INFORMATION: n is 5-propynyl-dU
<220> FEATURE:
<221> NAME/KEY: misc_feature
<222> LOCATION: (9)..(10)
<223> OTHER INFORMATION: n is 5-Me-dC
<220> FEATURE:
<221> NAME/KEY: misc_feature
<222> LOCATION: (15)..(15)
<223> OTHER INFORMATION: n is 5-Me-dC
<220> FEATURE:
<221> NAME/KEY: misc_feature
<222> LOCATION: (18)..(19)
<223> OTHER INFORMATION: n is 5-Me-dC
<220> FEATURE:
<221> NAME/KEY: misc_feature
<222> LOCATION: (22)..(22)
<223> OTHER INFORMATION: n is dG 3'-modified with terminal phosphate
      group

<400> SEQUENCE: 15
nggaanngnn agganganng gn                                             22

<210> SEQ ID NO 16
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (25)..(25)
<223> OTHER INFORMATION: n is dC 3'-modified with terminal phosphate
``` group

<400> SEQUENCE: 16
ntacaccgga attgccagga cgacn                                            25

<210> SEQ ID NO 17
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (24)..(24)
<223> OTHER INFORMATION: n is dC 3'-modified with terminal phosphate
      group

<400> SEQUENCE: 17
ntacaccgga attgccagga cgan                                             24

<210> SEQ ID NO 18
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with FAM
<220> FEATURE:
<221> NAME/KEY: misc_feature
<222> LOCATION: (23)..(23)
<223> OTHER INFORMATION: n is dC 3'-modified with terminal phosphate
      group

<400> SEQUENCE: 18
ncaccggaat tgccaggacg acn                                              23

<210> SEQ ID NO 19
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (22)..(22)
<223> OTHER INFORMATION: n is dC 3'-modified with terminal phosphate
      group

<400> SEQUENCE: 19
naccggaatt gccaggacga cn                                               22

<210> SEQ ID NO 20
<211> LENGTH: 26
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)

```
<223> OTHER INFORMATION: n is dA modified with FAM
<220> FEATURE:
<221> NAME/KEY: misc_feature
<222> LOCATION: (26)..(26)
<223> OTHER INFORMATION: n is dC 3'-modified with terminal phosphate
      group

<400> SEQUENCE: 20
ngtacaccgg aattgccagg acgacn                                          26

<210> SEQ ID NO 21
<211> LENGTH: 27
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (27)..(27)
<223> OTHER INFORMATION: n is dC 3'-modified with terminal phosphate
      group

<400> SEQUENCE: 21
nagtacaccg gaattgccag gacgacn                                         27

<210> SEQ ID NO 22
<211> LENGTH: 28
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (28)..(28)
<223> OTHER INFORMATION: n is dC 3'-modified with terminal phosphate
      group

<400> SEQUENCE: 22
ngagtacacc ggaattgcca ggacgacn                                        28

<210> SEQ ID NO 23
<211> LENGTH: 26
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (26)..(26)
<223> OTHER INFORMATION: n is dG 3'-modified with terminal phosphate
      group

<400> SEQUENCE: 23
ntacaccgga attgccagga cgaccn                                          26

<210> SEQ ID NO 24
<211> LENGTH: 27
<212> TYPE: DNA
<213> ORGANISM: Artificial
```

```
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (27)..(27)
<223> OTHER INFORMATION: n is dG 3'-modified with terminal phosphate
      group

<400> SEQUENCE: 24
ntacaccgga attgccagga cgaccgn                                           27

<210> SEQ ID NO 25
<211> LENGTH: 28
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (28)..(28)
<223> OTHER INFORMATION: n is dG 3'-modified with terminal phosphate
      group

<400> SEQUENCE: 25
ntacaccgga attgccagga cgaccggn                                          28

<210> SEQ ID NO 26
<211> LENGTH: 27
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with FAM
<220> FEATURE:
<221> NAME/KEY: misc_feature
<222> LOCATION: (27)..(27)
<223> OTHER INFORMATION: n is dG 3'-modified with terminal phosphate
      group

<400> SEQUENCE: 26
ngtacaccgg aattgccagg acgaccn                                           27

<210> SEQ ID NO 27
<211> LENGTH: 25
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dA modified with FAM
<220> FEATURE:
<221> NAME/KEY: misc_feature
<222> LOCATION: (25)..(25)
<223> OTHER INFORMATION: n is dC 3'-modified with terminal phosphate
      group

<400> SEQUENCE: 27
ngtacaccgg aattgccagg acgan                                             25
```

<210> SEQ ID NO 28
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (23)..(23)
<223> OTHER INFORMATION: n is dA 3'-modified with terminal phosphate
      group

<400> SEQUENCE: 28
ntacaccgga attgccagga cgn                                            23

<210> SEQ ID NO 29
<211> LENGTH: 22
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dG modified with FAM
<220> FEATURE:
<221> NAME/KEY: misc_feature
<222> LOCATION: (22)..(22)
<223> OTHER INFORMATION: n is dG 3'-modified with terminal phosphate
      group

<400> SEQUENCE: 29
ntacaccgga attgccagga cn                                             22

<210> SEQ ID NO 30
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dT modified with FAM
<220> FEATURE:
<221> NAME/KEY: misc_feature
<222> LOCATION: (24)..(24)
<223> OTHER INFORMATION: n is dC 3'-modified with terminal phosphate
      group

<400> SEQUENCE: 30
nacaccggaa ttgccaggac gacn                                           24

<210> SEQ ID NO 31
<211> LENGTH: 24
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: dC modified with FAM

<400> SEQUENCE: 31
nggaattgcc aggacgaccg ggtc                                           24

```
<210> SEQ ID NO 32
<211> LENGTH: 23
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM

<400> SEQUENCE: 32
ncggaattgc caggacgacc ggg                                          23

<210> SEQ ID NO 33
<211> LENGTH: 31
<212> TYPE: DNA
<213> ORGANISM: Artificial
<220> FEATURE:
<223> OTHER INFORMATION: Synthetic oligonucleotide template

<400> SEQUENCE: 33
aggacccggt cgtcctggca attccggtgt a                                 31

<210> SEQ ID NO 34
<211> LENGTH: 31
<212> TYPE: DNA
<213> ORGANISM: Artificial
<220> FEATURE:
<223> OTHER INFORMATION: Synthetic oligonucleotide template

<400> SEQUENCE: 34
aggacccagt cttcccggca attccggtgt a                                 31

<210> SEQ ID NO 35
<211> LENGTH: 31
<212> TYPE: DNA
<213> ORGANISM: Artificial
<220> FEATURE:
<223> OTHER INFORMATION: Synthetic oligonucleotide template

<400> SEQUENCE: 35
aggacccggt caccccagcg attccggtgt a                                 31

<210> SEQ ID NO 36
<211> LENGTH: 31
<212> TYPE: DNA
<213> ORGANISM: Artificial
<220> FEATURE:
<223> OTHER INFORMATION: Synthetic oligonucleotide template

<400> SEQUENCE: 36
aggacccggt catcccggcg attccggtgt a                                 31

<210> SEQ ID NO 37
<211> LENGTH: 31
<212> TYPE: DNA
<213> ORGANISM: Artificial
<220> FEATURE:
<223> OTHER INFORMATION: Synthetic oligonucleotide template

<400> SEQUENCE: 37
aggacccggt catcccggca attccggtgt a                                 31

<210> SEQ ID NO 38
<211> LENGTH: 31
```

```
<212> TYPE: DNA
<213> ORGANISM: Artificial
<220> FEATURE:
<223> OTHER INFORMATION: Synthetic oligonucleotide template

<400> SEQUENCE: 38
aggacccggt catcctggca attccggtgt a                              31

<210> SEQ ID NO 39
<211> LENGTH: 26
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (26)..(26)
<223> OTHER INFORMATION: n is N6-t-butylbenzyl-dA

<400> SEQUENCE: 39
gcagaaagcg tctagccatg gcgttn                                    26

<210> SEQ ID NO 40
<211> LENGTH: 28
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (28)..(28)
<223> OTHER INFORMATION: n is N6-t-butylbenzyl-dA

<400> SEQUENCE: 40
gcaagcaccc tatcaggcag taccacan                                  28

<210> SEQ ID NO 41
<211> LENGTH: 31
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: n is dC modified with FAM
<220> FEATURE:
<221> NAME/KEY: misc_feature
<222> LOCATION: (14)..(15)
<223> OTHER INFORMATION: BHQ-2 is inserted between nucleotide positions
      14 and 15.
<220> FEATURE:
<221> NAME/KEY: misc_feature
<222> LOCATION: (31)..(31)
<223> OTHER INFORMATION: n is dG 3'-modified with terminal phosphate
      group

<400> SEQUENCE: 41
nggtgtactc accgttccgc agaccactat n                              31

<210> SEQ ID NO 42
<211> LENGTH: 33
<212> TYPE: DNA
<213> ORGANISM: hepatitis C virus

<400> SEQUENCE: 42
tgagtacacc ggaattgctg ggaagactgg gtc                            33
```

PROBES AND METHODS FOR HEPATITIS C VIRUS TYPING USING SINGLE PROBE ANALYSIS

CROSS-REFERENCE TO RELATED APPLICATIONS

This application claims priority to and benefit of the following United States Provisional Patent Applications:
Application Ser. No. 60/695,991, filed Jun. 30, 2005;
Application Ser. No. 60/696,253, filed Jun. 30, 2005;
Application Ser. No. 60/696,293, filed Jun. 30, 2005; and
Application Ser. No. 60/696,303, filed Jun. 30, 2005.

Each of these specifications are hereby incorporated by reference in their entirety.

FIELD OF THE INVENTION

The invention relates to viral diagnostic procedures. Specifically, the invention relates to hepatitis C virus typing (e.g., genotyping and subtyping). The invention provides compositions and methods for HCV typing in, for example, a sample from a patient.

BACKGROUND OF THE INVENTION

Hepatitis C Virus (HCV) infection is a growing worldwide concern. HCV infections are generally persistent and induce chronic liver disease, manifested in cirrhosis of the liver and hepatocellular carcinoma. HCV is the leading cause for liver transplantation in the United States. Worldwide, approximately one million new HCV infections are reported annually; in the United States alone, an estimated four million persons are infected and 30,000 new infections occur annually.

Currently, HCV is responsible for an estimated 8,000 to 10,000 deaths annually in the United States. Without the development of improved diagnostics and therapeutics, that number is expected to triple in the next 10 to 20 years (National Institutes of Health Consensus Development Conference Panel (1997) National Institutes of Health Consensus Development Conference Panel statement: "Management of Hepatitis C," Hepatology 26(Suppl. 1):2S-10S).

The HCV genome is highly polymorphic, and a number of strains (termed genotypes and subtypes) have been characterized. The different viral types correlate with different disease outcomes and different responsiveness to therapeutic regimens. Knowing the viral genotype (and/or subtype) present in an infection provides the clinician with an important indicator for determining an optimal course of treatment for an infected patient. However, the development of simple, diagnostic methods that can differentiate the ever-increasing number of known HCV types has become a challenge.

There is a need in the art to develop improved methods for HCV diagnostics. There is a need for improved methods that can distinguish the increasingly large number of known HCV genotypic isolates, including genotypic subtypes. Furthermore, there is also a need in the art for methods that can simultaneously genotype and quantitate (e.g., determine the viral load or copy number) of an HCV infection. The present invention provides novel compositions and methods that meet these needs, as well as provide additional benefits.

Prior to a detailed description of the present invention, pertinent aspects of HCV nomenclature and biology are discussed below. These topics, required for understanding the invention, include discussion of the HCV genome, HCV typing nomenclature, clinical relevance of HCV typing and HCV typing methodologies.

HCV Genome

The HCV genome (see, FIG. 1) has a positive-sense single-stranded RNA genome approximately 10 kb in length with marked similarities to the genomes of members of the Pestivirus and Flavivirus genera. The original HCV isolate (HCV-1) had an approximately 9.4 kB genome containing a poly(A) tail at the 3' end (Choo et al. (1991) "Genetic organization and diversity of the hepatitis C virus," Proc. Natl. Acad. Sci. USA 88:2451-2455). The HCV-1 sequence contained a 5' untranslated region (5'-UTR) of 341 bases, a long open reading frame encoding a polyprotein of 3,011 amino acids, and a 3' untranslated region (3'-UTR) of about 27 bases. See the schematic of the HCV genome and polyprotein in FIG. 1.

The viral RNA genome is translated by the host translation apparatus as a single polyprotein product, which is then subjected to proteolytic processing to produce the viral proteins. The length of the open reading frame (ORF) of each genotype is characteristically different. For example, the open reading frame in type 1 isolates is approximately 9,400 ribonucleotides in length, while that of type 2 isolates is typically 9,099 nucleotides and that of type 3 isolates is typically 9,063 nucleotides (Bukh et al. (1995) "Genetic heterogeneity of hepatitis C virus: quasispecies and genotypes," Semin. Liver Dis., 15:41-63).

The HCV genomic structure/organization is most similar to that of the family Flaviviridae. Consistent with the known functions of most flavivirus proteins, the N-terminal HCV proteins are likely structural (including the C (capsid/core), E1 and E2 envelope proteins) and the C-terminal non-structural proteins, including NS2 (metalloprotease), NS3 (serine-protease/helicase), NS4 and NS5 (NS5B RNA polymerase) are believed to function in viral replication. A schematic view showing organization of the HCV RNA genome and encoded polypeptides is provided in FIG. 1.

Following identification and characterization of the prototypical HCV isolate (now termed HCV 1a), other isolates from around the world were (and continue to be) identified. Sequence comparisons reveal that these unique isolates can differ from each other by as much as 35% nucleotide non-identity over the full length of the HCV genome (Okamoto et al. (1992) Virology 188:331-341). Sequence variability is observed throughout the viral genome, with some regions showing more variability than others. For example, generally high sequence conservation is observed in the 5'-UTR region; conversely, some regions, including the envelope (E) region, show hypervariable nucleotide sequences.

HCV Typing Nomenclature

An understanding of HCV typing nomenclature is required prior to discussion of the present invention. Historically, investigators have used several classification systems and nomenclatures to characterize the various HCV strains, resulting in confusion in the scientific literature. A consensus HCV genotype/subtype nomenclature system has now been adopted (Simmonds et al. (1994) Letter, Hepatology 19:1321-1324; see also, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England). According to this system, HCV isolates are classified on the basis of nucleotide sequence divergence into major genetic groups designated as genotypes. These genotypes are numbered (in Arabic numerals), generally in the order of their discovery. HCV strains that are more closely related to each other within a genotype are designated as subtypes, which are assigned lowercase letters, generally in the order of their discovery. Genetic variants found within an individual isolate are termed quasispecies. Quasispecies of HCV result presumably from the accumulation of mutations during viral replication in the host.

The degree of relatedness between any two HCV isolates can be quantitated, for example, by determining the percentage of nucleotide identity between the two genomes over the full length of the genome. One example of this relatedness analysis, and how the nomenclature is used to reflect viral isolate relatedness, is shown in FIG. 2 (adapted from Zein (2000) "Clinical Significance of Hepatitis C Virus Genotypes," Clinical Microbiol. Reviews 13(2):223-235). Using the nomenclature proposed by Simmonds et al. (1994, Letter, Hepatology 19:1321-1324), the increasing degree of interrelatedness between genotypes, subtypes and quasispecies can be observed in the percentage of nucleotide sequence identity over the complete genome. The table in FIG. 2 reflects the proposal that HCV isolates that are quasispecies share the greatest degree of relatedness, and isolates of the same subtype within a genotype share greater sequence identity than isolates of different subtypes also within that genotype. p Alternatively, relatedness between HCV isolates can be quantitated by examining genomic identity over a smaller domain of the genome, as shown, for example, in FIG. 3. This comparison uses a 222 nucleotide segment derived from the viral NS5 open reading frame (nucleotide positions 7975-8196 in the prototype HCV gentotype 1a isolate). This comparison of sequence identity also supports the proposal of Simmonds et al. (1994, Letter, Hepatology 19:1321-1324) that HCV isolates of one subtype are more closely related to other subtypes of that same genotype, than to isolates from any other genotype.

Currently, eleven (11) HCV genotypes are recognized worldwide. However, there is published suggestion that the evolutionary (phylogenetic) relatedness between different genotypes should be reexamined, and the number of recognized genotypes into which HCV isolates are classified/assigned should be reassessed. Some reports suggest that subsets of HCV genotypes are more closely related to each other than to other more distantly related genotypes, which should be reflected in a modified HCV nomenclature. It is suggested that the 11 genotypes can be regrouped into six HCV clades. The grouping of clades reflects phylogenetic relationships between the genotypes, where genotypes 1, 2, 4 and 5 all represent distinct clades, but where genotypes 3 and 10 are placed into a single lade 3, and genotypes 6, 7, 8, 9 and 11 are placed into a single clade 6 (Robertson et al., (1998) Arch. Virol., 143(12):2493-2503; Zein (2000) "Clinical Significance of Hepatitis C Virus Genotypes," Clinical Microbiol. Reviews 13(2):223-235).

Approximately 78 HCV subtypes encompassing all 11 genotypes are known worldwide. A summary of some of these subtypes is shown in FIG. 4. This table provides a listing of some (but not all) HCV types, especially those subtypes that appear to be frequent clinical isolates. The names of prototypical and/or representative isolates known in the art are provided.

Many HCV isolates have been sequenced in their entirety. FIG. 5 provides a table showing the consensus sequences of a 33 nucleotide domain in the 5'-UTR of some of the clinically relevant HCV isolates. Nucleotide positions that are identical to the HCV type 1a nucleotide sequence are shown with a dash. Nucleotide positions that differ from the HCV type 1a are shown with the nucleotide change.

All references to HCV genotypes, subtypes and quasispecies herein are in accordance with the system described by Simmonds et al., 1994, (Letter, Hepatology 19:1321-1324), and also described in, for example, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England.

Clinical Relevance of HCV Typing

The typing of an HCV infection in a patient remains an important prognosticator for the aggressiveness of the infection, as well as the potential for the infection to respond to various therapeutic regimens. HCV genotype 1 represents a more aggressive strain and one that is less likely to respond to alpha interferon (INF-α) treatment (and combination therapies with ribavirin) than HCV genotype 2 or 3 (Nolte, "Hepatitis C Virus Genotyping: Clinical Implications and Methods," Molecular Diagnosis 6(4):265-277 [2001]; Dufour, "Hepatitis C: Laboratory Tests for Diagnosis and Monitoring of Infection," Clinical Laboratory News, November 2002, p. 10-14; Pawlotsky "Use and Interpretation of Hepatitis C Virus Diagnostic Assays," *Clinics in Liver Disease*, Vol. 7, Number 1 [February 2003]). The goal in typing an HCV infection is frequently to identify patients infected with HCV genotype 1 as opposed to those infected with other HCV types. Furthermore, with the identification of an expanding list of known HCV subtypes, there is a need in the art for simple HCV typing methods that can distinguish the complexity of HCV phylogeny for both clinical and research purposes. There is also a need in the art for HCV typing methods that simultaneously provide HCV load information (e.g., copy number and viral genome quantitation).

Substantial regional differences exist in the distribution of the HCV types. HCV subtypes 1a and 1b are the most common subtypes in the United States and Europe. In Japan, subtype 1b is responsible for up to 73% of cases of HCV infection. Although HCV subtypes 2a and 2b are relatively common in North America, Europe, and Japan, subtype 2c is found commonly in northern Italy. HCV genotype 3a is particularly prevalent in intravenous drug abusers in Europe and the United States. HCV genotype 4 appears to be prevalent in North Africa and the Middle East, and genotypes 5 and 6 seem to be confined to South Africa and Hong Kong, respectively. HCV genotypes 7, 8, and 9 have been identified only in Vietnamese patients, and genotypes 10 and 11 were identified in patients from Indonesia. (see, Nolte, "Hepatitis C Virus Genotyping: Clinical Implications and Methods," Molecular Diagnosis 6(4):265-277 [2001]; Pawlotsky "Hepatitis C Virus Genetic Variability: Pathogenic and Clinical Implications," *Clinics in Liver Disease*, Vol. 7, Number 1 [February 2003]; Zein "Clinical Significance of Hepatitis C Virus Genotypes," Clinical Microbiol. Reviews 13(2):223-235 [2000]).

Because of the geographic clustering of distinct HCV genotypes and subtypes, HCV typing can also be a useful epidemiologic marker in tracing the source of an HCV outbreak in a given population. For example, HCV typing was used to trace the source of HCV infection in a group of Irish women to contaminated anti-D immunoglobulins (Power et al., (1995) "Molecular epidemiology of an outbreak of infection with hepatitis C virus in recipients of anti-D immunoglobulin," Lancet 345:1211-1213). Additional examples of using HCV typing as an epidemiological marker are also known (see, for example, Hohne et al., (1994) "Sequence variability in the env-coding region of hepatitis C virus isolated from patients infected during a single source outbreak," Arch. Virol., 137:25-34; and Bronowicki et al., (1997) "Patient-to-patient transmission of hepatitis C virus during colonoscopy," N. Engl. J. Med., 337:237-240).

HCV Typing Methodologies

The HCV isolate found in any given infection varies by differences in geographical strain distribution, disease outcome, and response to anti-HCV therapy. Reliable methods for determining HCV genotype are an important clinical test. Furthermore, with the identification of numerous and distinct HCV species, it is important that HCV typing methods have the ability to distinguish numerous HCV types (genotypes and subtypes). For example, it is useful for an HCV genotyping test to be able to distinguish among at least five or more genotypes. Alternatively, it is useful for an HCV typing test to be able to distinguish among at least six or more subtypes. Nucleic acid-based methods for HCV typing are summarized below.

Nucleotide Sequencing

The reference standard for HCV genotyping and subtyping is nucleotide sequencing of a amplicon derived from the HCV genome by RT-PCR of HCV genomic RNA (e.g., from a clinical specimen from a patient) followed by phylogenetic assignment. However, direct sequencing is impractical due to low throughput (even with the introduction of automated sequencing apparatus using non-radioactive reagents) and the requirement for specialized equipment. Furthermore, using sequencing methodologies for genotyping and subtyping in cases of mixed infections can result in ambiguous results.

PCR-Based HCV Genotyping

Some typing methods use PCR reamplification using type-specific PCR primers. Typing is achieved by a primary PCR amplification with universal consensus primers (i.e., primers that will generate an HCV genomic amplicon regardless of the HCV type) followed by a nested PCR with the type-specific primers, for example, type-specific primers within the core region. These assays require multiple sets of PCR primers to generate sufficient type-specific PCR amplicons to make a genotype/subtype assignment. These methods have the drawback that they require multiple sets of PCR primers to accomplish the HCV typing, and often lack sensitivity and specificity (Xavier and Bukh (1998) "Methods for determining the hepatitis C genotype," Viral Hepatitis Rev., 4:1-19; Zein (2000) "Clinical Significance of Hepatitis C Virus Genotypes," Clinical Microbiol. Reviews 13(2):223-235; Okamoto et al., (1992) "Typing hepatitis C virus by polymerase chain reaction with type-specific primers: application to clinical surveys and tracing infectious sources," J. Gen. Virol., 73:673-679; Widell et al. (1994) "Genotyping of hepatitis C virus isolates by a modified polymerase chain reaction assay using type specific primers: epidemiological applications," J. Med. Virol., 44:272-279).

Hybridization-based HCV Genotyping

The typing of HCV isolates can be achieved by using multiple type-specific hybridization probes. This viral typing uses a primary PCR amplification using universal primers followed by hybridization with type-specific hybridization probes. This hybridization with the type-specific probes is done in fixed hybridization conditions, and the presence or absence of a hybridization complex(es) under the given hybridization conditions is scored. Any one probe in the assay is unable to definitively distinguish from among multiple genotypes/subtypes, thus necessitating the use of multiple probes to make a genotype/subtype assignment. This approach suffers from the drawback of requiring multiple probes for use in the HCV typing process.

One application of the HCV type-specific hybridization assay is the line-probe assay (LiPA), as described in various sources (Stuyver et al., (1993) "Typing of hepatitis C virus isolates and characterization of new subtypes using a line probe assay," J. Gen. Virol., 74:1093-1102; Stuyver et al., (1994) Proc. Natl. Acad. Sci. USA 91:10134-10138; Andonov and Chaudhary (1995) Jour. Clin. Microbiol., 33(1):254-256; Stuyver et al., (1996) Jour. Clin. Microbiol., 34(9):2259-2266; Stuyver et al., (2000) Jour. Clin. Microbiol., 38(2):702-707; and reviewed in, e.g., Maertens and Stuyver (1997) "Genotypes and genetic variation of hepatitis C virus," p. 182-233, In Harrison and Zuckerman (eds.), *The Molecular Medicine Of Viral Hepatitis*, John Wiley & Sons, Ltd., Chichester, England). A commercial kit incorporating this technology is produced by Innogenetics (Zwijnaarde, Belgium; see U.S. Pat. No. 6,548,244, issued Apr. 15, 2003 to Maertens et al., entitiled "PROCESS FOR TYPING HCV ISOLATES"; Published PCT International Application No. WO96/13590, published May 9, 1996, by Maertens and Stuyver, entitled "NEW SEQUENCES OF HEPATITIS C VIRUS GENOTYPES AND THEIR USE AS PROPHYLACTIC, THERAPEUTIC AND DIAGNOSTIC AGENTS"; and Published PCT International Application No. WO94/25601, published Nov. 10, 1994, by Maertens and Stuyver, entitled "NEW SEQUENCES OF HEPATITIS C VIRUS GENOTYPES AND THEIR USE AS THERAPEUTIC AND DIAGNOSTIC AGENTS"). The line-probe assay uses multiple type-specific probes (as many as 21 probes) immobilized onto a substrate (a test strip) in a dot-blot or slot-blot type of assay. An HCV amplicon derived from the HCV 5'-UTR region generated from a clinical specimen is simultaneously hybridized to the various probes under static hybridization conditions, and the resulting pattern of hybridization complexes reveals the virus type.

This line-probe assay suffers from the drawback of requiring the use of multiple probes (indeed, as many as 21 probes) to determine the HCV genotype and/or subtype of an HCV in a sample, as any one probe in the assay is unable to make a genotypic assignment.

Some reports use HCV typing methods that utilize one probe (or a small number of probes) to classify an HCV infection into one of a few subtypes. The probes used in these reports are not "type-specific," in that they can hybridize to multiple genotypes/subtypes by manipulating the hybridization conditions. However, these types of probes reported in the art (see, e.g., Schroter et al., (2002) Jour. Clin. Microbiol., 40(6):2046-2050; Bullock et al., (2002) Clinical Chemistry 48(12):2147-2154) are limited in the number of genotypes/subtypes they can differentiate.

Endonuclease Cleavage (RFLP)-Based HCV Genotyping

Typing of HCV has also been attempted by a variation of the traditional restriction fragment length polymorphism (RFLP) assay. This HCV assay uses digestion of a universal PCR amplicon with restriction endonucleases that recognize genotype-specific cleavage sites (see, e.g., Nakao et al., (1991) "Typing of hepatitis C virus genomes by restriction fragment length polymorphism," J. Gen. Virol., 72:2105-2112; Murphy et al., (1994) Letter, J. Infect. Dis., 169:473-475). Type-specific restriction sites are known to occur in the NS5 and the 5'-UTR domains. The use of this assay for genotyping/subtyping is limited due to the limited number of polymorphic loci that result in changes in restriction sites.

The present invention provides compositions and methods for HCV typing, and furthermore, provides compositions and methods for HCV typing that have advantages over other HCV typing methods known in the art. The invention provides methods for typing an HCV isolate, where the methods use a single HCV typing probe that is able to distinguish at least five HCV genotypes and/or at least six HCV subtypes. Furthermore, the invention provides methods that can simultaneously type an HCV isolate (for example, from a patient with an HCV infection) as well as quantitate the HCV genomic material in the sample (e.g., determine the viral load or copy number). The compositions and methods taught by the present invention also provide other advantages, which will be apparent upon reading the description of the invention.

SUMMARY OF THE INVENTION

The invention provides compositions and methods for HCV typing, e.g., genotyping and/or subtyping, where the methods require only a single typing probe to make an HCV genotype or subtype assignment. The compositions and methods of the invention can be used to assign an HCV sample to one of at least five HCV genotypes (for example, selected from genotypes 1, 2, 3, 4, 5 or 6), or assign an HCV sample to one of at least six subtypes (for example, selected from subtypes 1a/b/c, 2a/c, 2b, 3a, 4a, 5a or 6a), where the methods of the invention use only a single typing probe to make the HCV type assignment. The methods of the invention can also be used in cases of mixed HCV infection, where each HCV species present in the sample is assigned to an HCV type (genotype or subtype). The present invention provides advantages over methods for HCV typing currently known in the art which require the use of multiple probes to make a genotype or subtype assignment, or where a single probe is unable to differentiate from among five or more genotypes or six or more subtypes.

In some embodiments, the methods of the invention for determining the type of a hepatitis C virus (HCV) in a sample have the following steps: (a) amplifying a portion of the HCV genome from the sample, thereby producing at least one amplicon; (b) hybridizing the amplicon with a first probe (an HCV typing probe) to form a target hybridization complex, wherein (i) the first probe is complementary or partially complementary to a nucleotide sequence within an HCV genome; (ii) the region of hybridization complex complementarity or partial complementarity shows sequence heterogeneity among at least five HCV genotypes or at least six HCV subtypes; and, (iii) hybridization complexes comprising the first probe and at least five HCV genotypes or at least six subtypes have a distinguishing hybridization property that differentiates each of the HCV genotypes or HCV subtypes; (c) measuring the distinguishing hybridization property of the target hybridization complex; and, (d) correlating the measured distinguishing hybridization property of the target hybridization complex with an HCV genotype or subtype, based on the distinguishing hybridization property of the target hybridization complex.

Using this method, the HCV genotype that is identified can be selected from genotypes 1, 2, 3, 4, 5 and 6. The HCV subtype that is identified can be any subtype of genotypes 1, 2, 3, 4, 5 and 6. For example, the HCV subtype can be selected from 1a, 1b, 1c, 2a, 2b, 2c, 3a, 4a, 5a and 6a. However, it is not intended that the invention be limited to the HCV types listed herein, since the compositions and methods of the invention are applicable to any HCV type.

In some embodiments, the sample tested in the assay contains or is derived from human blood or human serum.

In some embodiments of these methods, the step of amplifying the HCV genetic material is by reverse transcription (RT) combined with polymerase chain reaction (PCR). This PCR can use a primer pair comprising the nucleotide sequences of, e.g., SEQ ID NOs: 39 and 40. In some aspects, the PCR uses primers that generate a PCR amplicon from a plurality of hepatitis C virus genotypes.

In various embodiments, the HCV typing probe is present during the amplifying step, or alternatively, is added after the amplifying step. In some embodiments, the HCV typing probe is complementary or partially complementary to nucleotide sequence within the 5'-UTR or the NS5 region of an HCV genome. For example, the typing probe can comprises a nucleic acid sequence selected from SEQ ID NOs: 8 through 27. The typing probe can comprises a FRET donor, a FRET quencher or both. In some aspects, the typing probe comprises a FRET donor moiety. In other aspects, the hybridizing step comprises mixing a FRET donor typing probe with a soluble FRET quencher. The soluble FRET quencher can be, e.g., a thiazine dye. The chemical structure of the typing probe is not particularly limited, for example, the probe can be a nucleotide oligomer comprising naturally-occurring nucleotides, modified nucleotides, nucleotide analogs, one or more unnatural bases, unnatural internucleotide linkages, unnatural nucleotide backbones, or any combinations thereof.

The HCV typing probe forms a hybridization complex with the HCV target (typically an HCV amplicon). This hybridization complex has properties that are unique according to the HCV type (e.g., the HCV genotype). This hybridization complex can be characterized by any of a variety of properties, and these properties can be used to distinguish the complex from complexes that comprise different HCV types. Such a property is therefore termed a distinguishing hybridization property. In some aspects, the distinguishing hybridization property is a temperature-dependent hybridization property. For example, the temperature-dependent hybridization property can be a melting temperature ($T_m$). When $T_m$ is used as the distinguishing property, the measuring step comprises detecting the target hybridization complex at a range of temperatures, thereby determining a $T_m$ of the target hybridization complex.

Using these methods, the hybridization property(ies) that are measured for the experimental sample can be compared to the hybridization properties of known HCV types or control samples. By making this comparison, the experimental sample can be assigned to a known HCV type based on a best-fit match. That is to say, in some embodiments, the correlating step comprises comparing the distinguishing hybridization property of the target hybridization complex to the distinguishing hybridization property of hybridization complexes comprising the typing probe and each of at least five HCV genotypes or at least six HCV subtypes.

In some embodiments, the methods for HCV typing can further incorporate HCV quantitation, preferably in the same reaction mix, and thus permitting a closed system. Methods for HCV quantitation in the experimental sample can use a TaqMan type probe to monitor HCV RT-PCR amplicon accumulation to derive a $C_T$ value. HCV quantitation can be made comparing the experimental $C_T$ value to $C_T$ values for control samples of known HCV viral load. This is to say, the HCV typing methods can further be used for determining the viral load of the HCV in the sample, wherein the amplifying step further comprises monitoring a rate of accumulation of the amplicon using reagents for real-time detection of amplicon accumulation and correlating the rate of amplicon accumulation with the viral load. The reagents for real-time detection of amplicon accumulation will typically comprise an amplicon quantitation probe, e.g., an amplicon quantitation probe comprising a nucleotide sequence of SEQ ID NO: 41. The amplicon quantitation probe can comprise a FRET donor moiety and a FRET quencher moiety wherein the amplicon quantitation probe forms a quantitation hybridization complex with the amplicon under conditions wherein base-pairing occurs. In this case, the amplifying step comprises detecting the donor moiety during the amplification step.

The invention provides also provides compositions and methods for HCV typing, e.g., genotyping and/or subtyping, where the methods require only a single typing probe to make an HCV genotype or subtype assignment, and furthermore, do not require an RT-PCR amplification step to generate an HCV amplicon. In these embodiments, the sample material (or materials optionally purified from or derived from the sample material) are used in the typing analysis. These methods for determining the type of a hepatitis C virus (HCV) in a sample generally comprise the steps: (a) hybridizing a nucleic acid derived from the HCV with a first probe (an HCV typing probe) to form a target hybridization complex, wherein: (i) the first probe is complementary or partially complementary to a nucleotide sequence within an HCV genome; (ii) the region of hybridization complex complementarity or partial complementarity shows sequence heterogeneity among at least five HCV genotypes or at least six HCV subtypes; and, (iii) hybridization complexes comprising the first probe and the at least five HCV genotypes or at least six HCV subtypes have a distinguishing hybridization property that differentiates each of the HCV genotypes or subtypes; (b) measuring the distinguishing hybridization property of the target hybridization complex; and, (c) correlating the measured distinguishing hybridization property of the target hybridization complex with a hepatitis C virus type, based on the distinguishing hybridization property of the target hybridization complex. The HCV typing probe used in these methods is not particularly limited, e.g., the typing probe can comprises a nucleic acid sequence selected from SEQ ID NOS: 8 through 27.

The invention provides probes that can be used with the HCV typing methods described herein. These probes can optionally be in combination with any of a variety of other components that facilitate their use in the methods of the invention. In some aspects, the invention provides a composition comprising a probe (i.e., an HCV typing probe) comprising a nucleotide sequence that is complementary or partially complementary to a nucleotide sequence within a hepatitis C virus (HCV) genome, where the region of probe complementarity or partial complementarity shows sequence heterogeneity among at least five HCV genotypes or at least six HCV subtypes; and where hybridization complexes comprising the probe and each of the HCV genotypes or subtypes have a distinguishing hybridization property that differentiates each of the genotypes or subtypes. Examples of such HCV typing probes include, but are not limited to, probes comprising a nucleic acid sequence selected from SEQ ID NOs: 8 through 27. In some aspects, the probe/target hybridization complex distinguishing hybridization property is a melting temperature ($T_m$).

The compositions of the invention that comprise an HCV typing probe can also optionally include a reverse transcriptase and a primer suitable for the initiation of reverse transcription of an HCV genome. The compositions compromising an HCV typing probe can also optionally include a nucleic acid that is either: (a) an HCV amplicon comprising nucleotide sequence that is complementary or partially complementary to a nucleotide sequence in the probe; (b) an amplification primer capable of generating the HCV amplicon; or (c) an amplification primer pair capable of generating the HCV amplicon; where the primer and the primer pair are admixed with a thermostable DNA-dependent DNA polymerase, free deoxyribonucleotide triphosphates and a suitable DNA polymerase reaction buffer.

In other aspects, the invention provides compositions that comprise a labeled HCV typing probe and a suitable soluble quencher, where the label on the probe and the soluble quencher form a FRET pair. For example, the invention provides a composition comprising: (a) a probe labeled with a FRET donor moiety that is complementary or partially complementary to a nucleotide sequence within a hepatitis C virus (HCV) genome, where the region of probe complementarity or partial complementarity shows sequence heterogeneity among at least five HCV genotypes or at least six HCV subtypes; and where hybridization complexes comprising the probe and a plurality of the HCV genotypes or subtypes have a distinguishing hybridization property that differentiates at least two HCV genotypes or at least two HCV subtypes; and, (b) a soluble FRET quencher comprising a thiazine dye, where the FRET quencher is capable of quenching the FRET donor moiety. In some embodiments, the distinguishing hybridization property is a melting temperature ($T_m$). In some embodiments, these compositions optionally further comprise a reverse transcriptase and a primer suitable for the initiation of reverse transcription of an HCV genome. In still other embodiments, the compositions comprising an HCV typing probe and a soluble quencher further comprise (c) a nucleic acid that is either: (i) an HCV amplicon comprising nucleotide sequence that is complementary or partially complementary to nucleotide sequence in the probe; (ii) an amplification primer capable of generating the HCV amplicon; or (iii) an amplification primer pair capable of generating the HCV amplicon; where the primer and the primer pair are admixed with a thermostable DNA-dependent DNA polymerase, free deoxyribonucleotide triphosphates and a suitable DNA polymerase reaction buffer.

The invention also provides kits, for example, diagnostic kits, that comprise at least one HCV typing probe. These kits can be used for determining the type of an HCV in a sample. For example, in some aspects, the HCV typing diagnostic kit comprises (a) at least one target probe (i.e., the HCV typing probe) that is complementary or partially complementary to a nucleotide sequence within an HCV genome, where the region of target probe complementarity or partial complementarity shows sequence heterogeneity among each of at least five HCV genotypes or at least six HCV subtypes, and hybridization complexes comprising the target probe and each of the HCV genotypes or subtypes have different distinguishing hybridization properties; and (b) instructions for measuring the distinguishing hybridization property of a hybridization complex comprising the target probe. These kits can contain, for example, an HCV typing probe comprising a nucleic acid sequence selected from SEQ ID NOs: 8 through 27.

In some embodiments, the diagnostic kits also contain reagents for conducting HCV quantitation (i.e., determining viral load). For example, such kits can further comprise (c) an amplification primer pair capable of generating an HCV amplicon, wherein the amplicon comprises nucleotide sequence that is complementary or partially complementary to nucleotide sequence in the target probe; and, (d) an amplicon quantitation probe for real-time detection of amplicon accumulation, where the amplicon quantitation probe forms a quantitation hybridization complex with the amplicon under conditions wherein base-pairing occurs. For example, the amplification primer pair can comprise the primers of SEQ ID NOs: 39 and 40, and the amplicon quantitation probe can comprise the nucleotide sequence of SEQ ID NO: 41.

In some embodiments, the diagnostic kits of the invention are packaged in one or more containers. In some embodiments, the HCV typing probe comprises a FRET label moiety, and the kit further comprises a soluble FRET quencher, e.g., a thiazine dye, that is capable of quenching the FRET label moiety. In other embodiments, the kit optionally further contains one or more additional components. For example, the diagnostic kit can further contain, alternatively or in any combination, a reverse transcriptase, at least one primer suitable for reverse transcriptase initiation from a hepatitis C virus genome, a thermostable DNA-dependent DNA polymerase, free deoxyribonucleotide triphosphates, standardization samples, positive control samples, negative control samples, buffers suitable for enzymatic reactions, sample collection tubes, amplification reaction tubes and multi-well plates.

In some embodiments, the invention provides systems that integrate the various aspects of the HCV typing methods of the invention and facilitate their use. In addition to the reagents required for performing the HCV hybridization analysis (for example, an HCV typing probe), the integrated systems of the invention can optionally comprise, for example, computer hardware, software, or other instrumentation for performing the HCV typing. For example, the invention provides systems that correlate detection of a signal with a hepatitis C virus (HCV) type, where the system comprises: (a) a detector for detecting the signal, where the signal correlates with a distinguishing hybridization property of a hybridization complex, where the hybridization complex comprises a probe that is complementary or partially complementary to a nucleotide sequence within an HCV genome and an amplicon comprising an HCV nucleotide sequence; and, (b) a correlation module that is operably coupled to the detector, where the correlation module correlates the signal with one of at least five HCV genotypes or at least six HCV subtypes by comparing the signal with a signal observed when detecting a distinguishing hybridization property of hybridization complexes comprising each of the HCV genotypes or subtypes. Optionally, in the systems of the invention, the distinguishing hybridization property is a melting temperature ($T_m$), and the correlation module comprises a dataset of predicted or experimentally determined $T_m$ values for hybridization complexes comprising the probe and each of at least five HCV genotypes or at least six HCV subtypes, where the dataset is in a computer readable format.

Definitions

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "a nucleic acid," also includes a plurality of nucleic acid molecules; use of the term "probe" includes, as a practical matter, many probe molecules, and the like.

Unless otherwise indicated, nucleic acids are written left to right in 5' to 3' orientation, and amino acid sequences are written left to right in amino (N-terminus) to carboxy (C-terminus) orientation. Numeric ranges recited within the specification are inclusive of the numbers defining the range and include each integer and any non-integer fraction within the defined range.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

As used herein, the term "base" refers to any nitrogen-containing heterocyclic moiety capable of forming Watson-Crick type hydrogen bonds in pairing with a complementary base or base analog. A large number of natural and synthetic (non-natural, or unnatural) bases, base analogs and base derivatives are known. Examples of bases include purines and pyrimidines, and modified forms thereof. The naturally occurring bases include, but are not limited to, adenine (A), guanine (G), cytosine (C), uracil (U) and thymine (T). As used herein, it is not intended that the invention be limited to naturally occurring bases, as a large number of unnatural (non-naturally occurring) bases and their respective unnatural nucleotides that find use with the invention are known to one of skill in the art. Examples of such unnatural bases are given below.

The term "nucleoside" refers to a compound consisting of a base linked to the C-1' carbon of a sugar, for example, ribose or deoxyribose.

The term "nucleotide" refers to a phosphate ester of a nucleoside, as a monomer unit or within a polynucleotide. "Nucleotide 5'-triphosphate" refers to a nucleotide with a triphosphate ester group attached to the sugar 5'-carbon position, and are sometimes denoted as "NTP", or "dNTP" and "ddNTP." A modified nucleotide is any nucleotide (e.g., ATP, TTP, GTP or CTP) that has been chemically modified, typically by modification of the base moiety. Modified nucleotides include, for example but not limited to, methylcytosine, 6-mercaptopurine, 5-fluorouracil, 5-iodo-2'-deoxyuridine and 6-thioguanine. As used herein, the term "nucleotide analog" refers to any nucleotide that is non-naturally occurring.

The terms "polynucleotide," "nucleic acid," "oligonucleotide," "oligomer," "oligo" or equivalent terms, as used herein refer to a polymeric arrangement of monomers that can be corresponded to a sequence of nucleotide bases, e.g., a DNA, RNA, peptide nucleic acid, or the like. A polynucleotide can be single- or double-stranded, and can be complementary to the sense or antisense strand of a gene sequence, for example. A polynucleotide can hybridize with a complementary portion of a target polynucleotide to form a duplex, which can be a homoduplex or a heteroduplex. The length of a polynucleotide is not limited in any respect. Linkages between nucleotides can be internucleotide-type phosphodiester linkages, or any other type of linkage. A "polynucleotide sequence" refers to the sequence of nucleotide monomers along the polymer. A "polynucleotide" is not limited to any particular length or range of nucleotide sequence, as the term "polynucleotide" encompasses polymeric forms of nucleotides of any length. A polynucleotide can be produced by biological means (e.g., enzymatically), or synthesized using an enzyme-free system. A polynucleotide can be enzymatically extendable or enzymatically non-extendable.

Polynucleotides that are formed by 3'-5' phosphodiester linkages are said to have 5'-ends and 3'-ends because the nucleotide monomers that are reacted to make the polynucleotide are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

As used herein, it is not intended that the term "polynucleotides" be limited to naturally occurring polynucleotides sequences or polynucleotide structures, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Non-limiting examples of such unnatural structures include non-ribose sugar backbones, 3'-5' and 2'-5' phosphodiester linkages, internucleotide inverted linkages (e.g., 3'-3' and 5'-5'), and branched structures. Furthermore, unnatural structures also include unnatural internucleotide analogs, e.g., peptide nucleic acids (PNAs), locked nucleic acids (LNAs), $C_1$-$C_4$ alkylphosphonate linkages such as methylphosphonate, phosphoramidate, $C_1$-$C_6$ alkyl-phosphotriester, phosphorothioate and phosphorodithioate internucleotide linkages. Furthermore, a polynucleotide can be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that they hybridize to a single-stranded nucleic acid target in a manner similar to naturally occurring polynucleotides.

As used herein, the term "sequence of a polynucleotide," "nucleic acid sequence," "polynucleotide sequence", and equivalent or similar phrases refer to the order of nucleotides in the polynucleotide. In some cases, a "sequence" refers more specifically to the order and identity of the bases that are each attached to the nucleotides. A sequence is typically read (written) in the 5' to 3' direction. Unless otherwise indicated, a particular polynucleotide sequence of the invention optionally encompasses complementary sequences, in addition to the sequence explicitly indicated.

As used herein, the terms "amplification," "amplifying" and the like refer generally to any process that results in an increase in the copy number of a molecule or set of related molecules. As it applies to polynucleotide molecules, amplification means the production of multiple copies of a polynucleotide molecule, or a portion of a polynucleotide molecule, typically starting from a small amount of a polynucleotide (e.g., a viral genome), where the amplified material (e.g., a viral PCR amplicon) is typically detectable. Amplification of polynucleotides encompasses a variety of chemical and enzymatic processes. The generation of multiple DNA copies from one or a few copies of a template DNA molecule during a polymerase chain reaction (PCR), a strand displacement amplification (SDA) reaction, a transcription mediated amplification (TMA) reaction, a nucleic acid sequence-based amplification (NASBA) reaction, or a ligase chain reaction (LCR) are forms of amplification. Amplification is not limited to the strict duplication of the starting molecule. For example, the generation of multiple cDNA molecules from a limited amount of viral RNA in a sample using RT-PCR is a form of amplification. Furthermore, the generation of multiple RNA molecules from a single DNA molecule during the process of transcription is also a form of amplification.

In some embodiments, amplification is optionally followed by additional steps, for example, but not limited to, labeling, sequencing, purification, isolation, hybridization, size resolution, expression, detecting and/or cloning.

As used herein, the term "polymerase chain reaction" (PCR) refers to a method for amplification well known in the art for increasing the concentration of a segment of a target polynucleotide in a sample, where the sample can be a single polynucleotide species, or multiple polynucleotides. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers. Reverse transcriptase PCR (RT-PCR) is a PCR reaction that uses RNA template and a reverse transcriptase, or an enzyme having reverse transcriptase activity, to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Methods for a wide variety of PCR applications are widely known in the art, and described in many sources, for example, Ausubel et al. (eds.), Current Protocols in Molecular Biology, Section 15, John Wiley & Sons, Inc., New York (1994).

As used herein, the expression "asymmetric PCR" refers to the preferential PCR amplification of one strand of a DNA target by adjusting the molar concentration of the primers in a primer pair so that they are unequal. An asymmetric PCR reaction produces a predominantly single-stranded product and a smaller quantity of a double-stranded product as a result of the unequal primer concentrations. As asymmetric PCR proceeds, the lower concentration primer is quantitatively incorporated into a double-stranded DNA amplicon, but the higher concentration primer continues to prime DNA synthesis, resulting in continued accumulation of a single stranded product.

As used herein, the term "DNA-dependent DNA polymerase" refers to a DNA polymerase enzyme that uses deoxyribonucleic acid (DNA) as a template for the synthesis of a complementary and antiparallel DNA strand. Thermostable DNA-dependent DNA polymerases find use in PCR amplification reactions. Suitable reaction conditions (and reaction buffers) for DNA-dependent DNA polymerase enzymes, and indeed any polymerase enzyme, are widely known in the art, and are described in numerous sources (see, e.g., Ausubel et al. (eds.), Current Protocols in Molecular Biology, Vol. 1-4, John Wiley & Sons, Inc., New York [1994; supplemented through September 2004]). Reaction buffers for DNA-dependent DNA polymerase enzymes can comprise, for example, free deoxyribonucleotide triphosphates, salts and buffering agents.

As used herein, the term "DNA-dependent RNA polymerase" refers to an RNA polymerase enzyme that uses deoxyribonucleic acid (DNA) as a template for the synthesis of an RNA strand. The process mediated by a DNA-dependent RNA polymerase is commonly referred to as "transcription."

As used herein, the term "RNA-dependent DNA polymerase" refers to a DNA polymerase enzyme that uses ribonucleic acid (RNA) as a template for the synthesis of a complementary and antiparallel DNA strand. The process of generating a DNA copy of an RNA molecule is commonly termed "reverse transcription," or "RT," and the enzyme that accomplishes that is a "reverse transcriptase." Some naturally-occurring and mutated DNA polymerases also possess reverse transcription activity.

As used herein, the term "thermostable," as applied to an enzyme, refers to an enzyme that retains its biological activity at elevated temperatures (e.g., at 55° C. or higher), or retains its biological activity following repeated cycles of heating and cooling. Thermostable polynucleotide polymerases find particular use in PCR amplification reactions.

As used herein, the term "primer" refers to an enzymatically extendable oligonucleotide, generally with a defined sequence that is designed to hybridize in an antiparallel manner with a complementary, primer-specific portion of a target sequence. Further, a primer can initiate the polymerization of nucleotides in a template-dependent manner to yield a polynucleotide that is complementary to the target polynucleotide. The extension of a primer annealed to a target uses a suitable DNA or RNA polymerase in suitable reaction conditions. One of skill in the art knows well that polymerization reaction conditions and reagents are well established in the art, and are described in a variety of sources.

A primer nucleic acid does not need to have 100% complementarity with its template subsequence for primer elongation to occur; primers with less than 100% complementarity can be sufficient for hybridization and polymerase elongation to occur. Optionally, a primer nucleic acid can be labeled, if desired. The label used on a primer can be any suitable label, and can be detected by, for example, by spectroscopic, photochemical, biochemical, immunochemical, chemical, or other detection means.

As used herein, the expression "amplification primer" refers to a primer that is generally in molar excess relative to its target polynucleotide sequence, and primes template-dependent enzymatic DNA synthesis and amplification of the target sequence (and sequence downstream from the site of hybridization) to yield a single-stranded amplicon.

As used herein, the expression "amplification primer pair" refers to a set of two primers that are generally in molar excess relative to their target polynucleotide sequence, and together prime template-dependent enzymatic DNA synthesis and amplification of the target sequence to yield a double-stranded amplicon.

As used herein, the term "amplicon" refers to a polynucleotide molecule (or collectively the plurality of molecules) produced following the amplification of a particular target nucleic acid. The amplification method used to generate the amplicon can be any suitable method, most typically, for example, by using a PCR methodology. An amplicon is typically, but not exclusively, a DNA amplicon. An amplicon can be single-stranded or double-stranded, or in a mixture thereof in any concentration ratio.

As used herein, the expression "real-time detection of amplicon accumulation" refers to the detection of, and typically the quantitation thereof, of a specific amplicon or amplicons, as the amplicon(s) is/are being produced (typically by PCR) without the need for a detection or quantitation step following the completion of the amplification. The terms "real-time PCR" or "kinetic PCR" refer to real-time detection and/or quantitation of amplicon generated in a PCR.

A common method for real-time detection of amplicon accumulation is by a 5'-nuclease assay, also termed a fluorogenic 5'-nuclease assay, e.g., a TaqMan analysis; see, Holland et al., Proc. Natl. Acad. Sci. USA 88:7276-7280 (1991); and Heid et al., Genome Research 6:986-994 (1996). In the TaqMan PCR procedure, two oligonucleotide primers are used to generate an amplicon specific to the PCR reaction. A third oligonucleotide (the TaqMan probe) is designed to hybridize with a nucleotide sequence in the amplicon located between the two PCR primers. The probe may have a structure that is non-extendible by the DNA polymerase used in the PCR reaction, and is typically (but not necessarily) colabeled with a fluorescent reporter dye and a quencher moiety in close proximity to one another. The emission from the reporter dye is quenched by the quenching moiety when the fluor and quencher are in close proximity, as they are on the probe. In some cases, the probe may be labeled with only a fluorescent reporter dye or another detectable moiety.

The TaqMan PCR reaction uses a thermostable DNA-dependent DNA polymerase that possesses a 5'-3' nuclease activity. During the PCR amplification reaction, the 5'-3' nuclease activity of the DNA polymerase cleaves the labeled probe that is hybridized to the amplicon in a template-dependent manner. The resultant probe fragments dissociate from the primer/template complex, and the reporter dye is then free from the quenching effect of the quencher moiety. Approximately one molecule of reporter dye is liberated for each new amplicon molecule synthesized, and detection of the unquenched reporter dye provides the basis for quantitative interpretation of the data, such that the amount of released fluorescent reporter dye is directly proportional to the amount of amplicon template.

One measure of the TaqMan assay data is typically expressed as the threshold cycle ($C_T$). Fluorescence levels are recorded during each PCR cycle and are proportional to the amount of product amplified to that point in the amplification reaction. The PCR cycle when the fluorescence signal is first recorded as statistically significant, or where the fluorescence signal is above some other arbitrary level (e.g., the arbitrary fluorescence level, or AFL), is the threshold cycle ($C_T$).

Protocols and reagents for 5'-nuclease assays are well known to one of skill in the art, and are described in various sources. For example, 5'-nuclease reactions and probes are described in U.S. Pat. No. 6,214,979, entitled "HOMOGENEOUS ASSAY SYSTEM," issued Apr. 10, 2001 to Gelfand et al.; U.S. Pat. No. 5,804,375, entitled "REACTION MIXTURES FOR DETECTION OF TARGET NUCLEIC ACIDS," issued Sep. 8, 1998 to Gelfand et al.; U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al.; and U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., all of which are incorporated by reference.

Variations in methodologies for real-time amplicon detection are also known, and in particular, where the 5'-nuclease probe is replaced by double-stranded DNA intercalating dye resulting in fluorescence that is dependent on the amount of double-stranded amplicon that is present in the amplification reaction. See, for example, U.S. Pat. No. 6,171,785, entitled "METHODS AND DEVICES FOR HEMOGENEOUS NUCLEIC ACID AMPLIFICATION AND DETECTOR,"

issued Jan. 9, 2001 to Higuchi; and U.S. Pat. No. 5,994,056, entitled "HOMOGENEOUS METHODS FOR NUCLEIC ACID AMPLIFICATION AND DETECTION," issued Nov. 30, 1999 to Higuchi, each of which are incorporated by reference.

TaqMan® PCR can be performed using commercially available kits and equipment, such as, for example, ABI PRISM® 7700 Sequence Detection System (Applied Biosystems, Foster City, Calif.), or LightCycler® (Roche Applied Sciences, Mannheim, Germany). In a preferred embodiment, the 5' nuclease assay procedure is run on a real-time quantitative PCR device such as the ABI PRISM® 7700 Sequence Detection System. The system consists of a thermocycler, laser, charge-coupled device (CCD), camera and computer. The system amplifies samples in a 96-well microtiter plate format on a thermocycler. During amplification, laser-induced fluorescent signal is collected in real-time through fiber optics cables for all 96 wells, and detected at the CCD camera. The system includes software for running the instrument and for analyzing the data.

As used herein, the terms "hybridization" and "annealing" and the like are used interchangeably and refer to the base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotide molecules is typically base specific, e.g., A/T and G/C, by Watson/Crick and/or Hoogsteen-type hydrogen bonding. It is not a requirement that two polynucleotides have 100% complementarity over their full length to achieve hybridization. In some aspects, a hybridization complex can form from intermolecular interactions, or alternatively, can form from intramolecular interactions.

As used herein, the phrases "specifically hybridize," "specific hybridization" and the like refer to hybridization resulting in a complex where the annealing pair show complementarity, and preferentially bind to each other to the exclusion of other potential binding partners in the hybridization reaction. It is noted that the term "specifically hybridize" does not require that a resulting hybridization complex have 100% complementarity; hybridization complexes that have mismatches can also specifically hybridize and form a hybridization complex. The degree of specificity of the hybridization can be measured using a distinguishing hybridization property, e.g., the melting temperature of the hybridization complex ($T_m$).

As used herein, the phrase "conditions wherein base-pairing occurs" refers to any hybridization conditions that permit complementary polynucleotides or partially complementary polynucleotides to form a stable hybridization complex.

As used herein, the terms "stringent," "stringent conditions," "high stringency" and the like denote hybridization conditions of generally low ionic strength and high temperature, as is well known in the art. See, e.g., Sambrook et al., *Molecular Cloning: A Laboratory Manual*, 3$^{rd}$ Ed., Cold Spring Harbor Laboratory Press, Cold Spring Harbor, N.Y. (2001); *Current Protocols in Molecular Biology* (Ausubel et al., ed., J. Wiley & Sons Inc., New York, 1997), which are incorporated herein by reference. Generally, stringent conditions are selected to be about 5-30° C. lower than the thermal melting point ($T_m$) for the hybridization complex comprising the specified sequence at a defined ionic strength and pH. Alternatively, stringent conditions are selected to be about 5-15° C. lower than the $T_m$ for the specified sequence at a defined ionic strength and pH. The $T_m$ is the temperature (under defined ionic strength, pH and nucleic acid concentration) at which 50% of the hybridization complexes comprising complementary (or partially complementary) polynucleotides become dissociated.

As used herein, the expression "low stringency" denotes hybridization conditions of generally high ionic strength and lower temperature. Under low stringency hybridization conditions, polynucleotides with imperfect complementarity can more readily form hybridization complexes.

As used herein, the terms "complementary" or "complementarity" are used in reference to antiparallel strands of polynucleotides related by the Watson-Crick and Hoogsteen-type base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands (no mismatches in the polynucleotide duplex). However, complementarity need not be perfect; stable duplexes, for example, may contain mismatched base pairs or unmatched bases. The terms "partial complementarity," "partially complementary," "incomplete complementarity" or "incompletely complementary" and the like refer to any alignment of bases between antiparallel polynucleotide strands that is less than 100% perfect (e.g., there exists at least one mismatch or unmatched base in the polynucleotide duplex). For example, the alignment of bases between the antiparallel polynucleotide strands can be at least 99%, 95%, 90%, 85%, 80%, 75%, 70%, 65%, 60%, 55%, or 50%, or any value between.

Furthermore, a "complement" of a target polynucleotide refers to a polynucleotide that can combine (e.g., hybridize) in an antiparallel association with at least a portion of the target polynucleotide. The antiparallel association can be intramolecular, e.g., in the form of a hairpin loop within a nucleic acid molecule, or intermolecular, such as when two or more single-stranded nucleic acid molecules hybridize with one another.

As used herein, "target", "target polynucleotide", "target sequence" and the like refer to a specific polynucleotide sequence that is the subject of hybridization with a complementary polynucleotide, e.g., a labelled probe or a DNA polymerase primer. The hybridization complex formed as a result of the annealing of a polynucleotide with its target is termed a "target hybridization complex." The hybridization complex can form in solution (and is therefore soluble), or one or more component of the hybridization complex can be affixed to a solid phase (e.g., to a dot blot, affixed to a bead system to facilitate removal or isolation of target hybridization complexes, or in a microarray). The structure of the target sequence is not limited, and can be composed of DNA, RNA, analogs thereof, or combinations thereof, and can be single-stranded or double-stranded. A target polynucleotide can be derived from any source, including, for example, any living or once living organism, including but not limited to prokaryote, eukaryote, plant, animal, and virus, as well as synthetic and/or recombinant target sequences. For example, as described herein, a PCR amplicon derived from viral genomic sequence can serve as a target.

In some aspects, the target polynucleotide in a hybridization complex serves as a "template," where an extendable polynucleotide primer binds to the template and initiates nucleotide polymerization using the base sequence of the template as a pattern for the synthesis of a complementary polynucleotide.

As used herein, the term "probe" refers typically to a polynucleotide that is capable of hybridizing to a target nucleic acid of interest. Typically, but not exclusively, a probe is associated with a suitable label or reporter moiety so that the probe (and therefore its target) can be detected, visualized, measured and/or quantitated. Detection systems for labelled probes include, but are not limited to, the detection of fluorescence, fluorescence quenching (e.g., when using a FRET pair detection system), enzymatic activity, absorbance, molecular mass, radioactivity, luminescence or binding properties that permit specific binding of the reporter (e.g., where the reporter is an antibody). In some embodiments, a probe can be an antibody, rather than a polynucleotide, that has binding specificity for a nucleic acid nucleotide sequence of interest. It is not intended that the present invention be limited to any particular probe label or probe detection system. The source of the polynucleotide used in the probe is not limited, and can be produced synthetically in a non-enzymatic system, or can be a polynucleotide (or a portion of a polynucleotide) that is produced using a biological (e.g., enzymatic) system (e.g., in a bacterial cell).

Typically, a probe is sufficiently complementary to a specific target sequence contained in a nucleic acid to form a stable hybridization complex with the target sequence under a selected hybridization condition, such as, but not limited to, a stringent hybridization condition. A hybridization assay carried out using the probe under sufficiently stringent hybridization conditions permits the selective detection of a specific target sequence.

As used herein, the terms "label" or "reporter," in their broadest sense, refer to any moiety or property that is detectable, or allows the detection of, that which is associated with it. For example, a polynucleotide that comprises a label is detectable (and in some aspects is referred to as a probe). Ideally, a labeled polynucleotide permits the detection of a hybridization complex that comprises the polynucleotide. In some aspects, e.g., a label is attached (covalently or non-covalently) to a polynucleotide. In various aspects, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels vary widely in their structures and their mechanisms of action.

Examples of labels include, but are not limited to, fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, Cy 5.5 and Cy7, and are commercially available from, e.g., Amersham Biosciences Corp. (Piscataway, N.J., USA).

As used herein, the term "FRET" (fluorescent resonance energy transfer) and equivalent terms refers generally to a dynamic distance-dependent interaction between electron states of two dye molecules in which energy is transferred from a donor molecule to an acceptor molecule without emission of a photon from the donor molecule. The efficiency of FRET is dependent on the inverse of the intermolecular separation between the dyes, making it useful over distances comparable with the dimensions of biological macromolecules. Generally, FRET allows the imaging, kinetic analysis and/or quantitation of colocalizing molecules or conformational changes in a single molecule with spatial resolution beyond the limits of conventional optical microscopy. In general, FRET requires, (a) the donor and acceptor molecules must be in close proximity (typically, e.g., 10-100 Å), (b) the absorption spectrum of the acceptor must overlap the fluorescence emission spectrum of the donor, and (c) the donor and acceptor transition dipole orientations must be approximately parallel.

In most FRET applications, the donor and acceptor dyes are different, in which case FRET can be detected by the appearance of sensitized fluorescence of the acceptor or by quenching of donor fluorescence. In some cases, the donor and acceptor are the same, and FRET can be detected by the resulting fluorescence depolarization. Use of a single donor/acceptor molecule in a FRET system is described, for example, in Published US Patent Application No. 2004/0096926, by Packard and Komoriya, published May 20, 2004, entitled "COMPOSITIONS FOR THE DETECTION OF ENZYME ACTIVITY IN BIOLOGICAL SAMPLES AND METHODS OF USE THEREOF," which is hereby incorporated by reference.

FRET has become an important technique for investigating a variety of biological phenomena that are characterized by changes in molecular proximity. FRET techniques are now pervasive in many biological laboratories, and have been adapted for use in a variety of biological systems, including but not limited to, detection of nucleic acid hybridization, real-time PCR assays and SNP detection, structure and conformation of proteins, spatial distribution and assembly of protein complexes, receptor/ligand interactions, immunoassays, probing interactions of single molecules, structure and conformation of nucleic acids, primer-extension assays for detecting mutations, automated DNA sequencing, distribution and transport of lipids, membrane fusion assays (lipid-mixing assays of membrane fusion), membrane potential sensing, fluorogenic protease substrates, and indicators for cyclic AMP and zinc.

As used herein, the term "FRET donor" refers typically to a moiety that produces a detectable emission of radiation, e.g., fluorescent or luminescent radiation, that can be transferred to a suitable FRET acceptor in sufficient proximity. The expression "FRET donor" can be used interchangeably with "FRET label" or "FRET label moiety."

As used herein, the terms "quencher," "quencher moiety," "acceptor," "acceptor moiety" and "light emission modifier" and similar and equivalent terms refer generally to a moiety that reduces and/or is capable of reducing the detectable emission of radiation, for example but not limited to, fluorescent or luminescent radiation, from a source that would otherwise have emitted this radiation. Generally, a quencher refers to any moiety that is capable of reducing light emission. The degree of quenching is not limited, per se, except that a quenching effect should minimally be detectable by whatever detection instrumentation is used. In some aspects, a quencher reduces the detectable radiation emitted by the source by at least 50%, alternatively by at least 80%, and alternatively and most preferably by at least 90%.

In some embodiments, the quencher results in a reduction in the fluorescence emission from a donor, and thus the donor/quencher forms a FRET pair, and the quencher is termed a "FRET quencher," or "FRET acceptor," and the donor is a "FRET donor."

It is not intended that that the term "quencher" be limited to FRET quenchers. For example, quenching can involve any type of energy transfer, including but not limited to, photoelectron transfer, proton coupled electron transfer, dimer formation between closely situated fluorophores, transient excited state interactions, collisional quenching, or formation of non-fluorescent ground state species. In some embodiments, a quencher refers to a molecule that is capable of reducing light emission. There is no requirement for a spectral overlap between the fluorophore and the quencher. As used herein, "quenching" includes any type of quenching, including dynamic (Forster-Dexter energy transfer, etc.), and static (ground state complex). Alternatively still, a quencher can dissipate the energy absorbed from a fluorescent dye in a form other than light, e.g., as heat.

In some embodiments, some quenchers can re-emit the energy absorbed from a FRET donor at a wavelength or using a signal type that is distinguishable from the FRET donor emission, and at a wavelength or signal type that is characteristic for that quencher, and thus, in this respect, a quencher can also be a "label."

For general discussion on the use of flourescence probe systems, see, for example, *Principles of Fluorescence Spectroscopy*, by Joseph R. Lakowicz, Plenum Publishing Corporation, 2nd edition (Jul. 1, 1999) and *Handbook of Fluorescent Probes and Research Chemicals*, by Richard P. Haugland, published by Molecular Probes, 6th edition (1996).

As used herein, the expressions "soluble acceptor," "soluble quencher," "soluble light emission modifier" or the like refer to an acceptor moiety that is not attached to any other molecule, and is largely soluble or otherwise not bound to any other molecule or solid phase. For example, some thiazine dyes e.g., new methylene blue, can be used as soluble quenchers. In some embodiments, the soluble quencher is a soluble FRET quencher, where the soluble FRET quencher is part of a functional FRET pair, also comprising a FRET donor.

As used herein, the terms "thiazine dye" and "thiazin dye" (these terms are synonymous and are used interchangeably in the art) refer to any of a class of organic chemical compounds containing a ring composed of one sulfur atom, one nitrogen atom, and four carbon atoms. Examples of thiazine dyes that can be used as soluble quenchers include, e.g., methylene blue ($C_{16}H_{18}ClN_3S$), methylene green ($C_{16}H_{17}ClN_4O_2S$), thionin ($C_{12}H_{10}ClN_3S$), sym-dimethylthionin, toluidine blue 0 ($C_5H_{16}N_3SCl$), new methylene blue ($C_{18}H_{22}ClN_3S$), methylene violet bernthsen, azure A ($C_{14}H_{14}ClN_3S$), azure B ($C_{15}H_{16}ClN_3S$), azure C, 1,9-dimethylmethylene blue, toluidine blue O, and methylene violet bernthsen. The structures of some of these compounds are shown in FIG. 8.

Further detailed description of soluble light emission modifiers and the uses thereof is found in cofiled U.S. patent appl. Ser. No. 11/474,062, filed on June 23, 2006, entitled "LIGHT EMISSION MODIFIERS AND THEIR USES IN NUCLEIC ACID DETECTION, AMPLIFICATION AND ANALYSIS," by Gupta and Will, the entire content of which is hereby incorporated by reference in its entirety for all purposes.

As used herein, the expression "FRET pair" and similar and equivalent terms refers to the pairing of a FRET donor moiety and a FRET acceptor moiety, such that FRET is observed when the donor and the acceptor are within suitable proximity to each other. Generally, but not exclusively, the donor moiety and the acceptor moiety are attached to various molecules of interest (e.g., polynucleotide probes).

A wide variety of dyes, fluors, quenchers, and fluorescent proteins, along with other reagents and detection/imaging instrumentation have been developed for use in FRET analysis and are widely commercially available. One of skill in the art recognizes appropriate FRET protocols, reagents and instrumentation to use for any particular analysis.

Molecules commonly used in FRET include, for example but not limited to, fluorescein, FAM, JOE, rhodamine, R6G, TAMRA, ROX, DABCYL, and EDANS. Whether a fluorescent dye is a label or a quencher is defined by its excitation and emission spectra, and also by the fluorescent dye with which it is paired. For example, FAM is most efficiently excited by light with a wavelength of 488 nm, and emits light with a spectrum of 500 to 650 nm, and an emission maximum of 525 nm. FAM is a suitable donor label for use with, e.g., TAMRA as a quencher, which has at its excitation maximum 514 nm. Examples of non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, wherein at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Examples of quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

As used herein, a "moiety" or "group" refers to a portion or a constituent part of a larger molecule or complex. For example, an oligonucleotide probe can comprise a label moiety.

As used herein, a "distinguishing hybridization property" refers to any property of a hybridization complex that can be used to distinguish one complex from another complex or any number of other complexes. One single-stranded nucleic acid molecule can participate a large number of hybridization complexes with various target molecules, where the number, positions and types of nucleotide base mismatches (if any) vary. Examples of distinguishing hybridization properties include, for example but not limited to, melting analysis (e.g., $T_m$ analysis), HMA (heteroduplex mobility analysis; White et al., J Clin Microbiol (2000) 38:477-482), DHPLC (denaturing HPLC), CFLP (cleavage fragment length polymorphism; Marshall et al., J Clin Microbiol (1997) 35:3156-3162), TGCE (thermal gradient capillary electrophoresis); SURVEYOR™ nuclease mutation detection kits, SSCP (single strand conformation polymorphism), etc.

As used herein, a "temperature-dependent hybridization property" refers to any quantitative temperature-dependent characteristic of a hybridization complex. For example, the melting temperature ($T_m$) is a temperature-dependent distinguishing hybridization property. However, a temperature-dependent hybridization property is not limited to $T_m$. For example, the temperature at which 25% of a population of double-stranded polynucleotides or nucleobase oligomers (e.g., hybridization complexes), in homoduplexes or heteroduplexes, become dissociated into single strands ($T_{25}$) is also a defining characteristic of the hybridization complex. Similarly, the temperature at which 75% of a population of double-stranded polynucleotides or nucleobase oligomers (e.g., hybridization complexes), in homoduplexes or heteroduplexes, become dissociated into single strands ($T_{75}$) is also a defining property of the hybridization complex. Alternatively, the percentage of dissociation of a hybridization complex at any defined temperature is a quantitative temperature dependent hybridization property. Alternatively still, an "annealing curve" (as opposed to a melting curve) can be used to characterize a hybridization complex. In the annealing curve analysis, the behavior of the target and the probe polynucleotide strands is observed with decreasing temperature (as opposed to increasing temperature as used in a melting curve analysis). Methods for measuring the extent of dissociation or annealing of a hybridization complex are well known to one of skill in the art.

As used herein, the term "$T_m$" is used in reference to the "melting temperature." The melting temperature is the temperature at which one half of a population of double-stranded polynucleotides or nucleobase oligomers (e.g., hybridization complexes), in homoduplexes or heteroduplexes, become dissociated into single strands. The prediction of a $T_m$ of a duplex polynucleotide takes into account the base sequence as well as other factors including structural and sequence characteristics and nature of the oligomeric linkages. Methods for predicting and experimentally determining $T_m$ are known in the art. For example, a $T_m$ is traditionally determined by a melting curve, wherein a duplex nucleic acid molecule is heated in a controlled temperature program, and the state of association/dissociation of the two single strands in the duplex is monitored and plotted until reaching a temperature where the two strands are completely dissociated. The $T_m$ is read from this melting curve. Alternatively, a $T_m$ can be determined by an annealing curve, wherein a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The $T_m$ is read from this annealing curve.

As used herein, the term "sample" is used in its broadest sense, and refers to any material subject to analysis. The term "sample" refers typically to any type of material of biological origin, for example, any type of material obtained from animals or plants. A sample can be, for example, any fluid or tissue such as blood or serum, and furthermore, can be human blood or human serum. A sample can be cultured cells or tissues, cultures of microorganisms (prokaryotic or eukaryotic), or any fraction or products produced from or derived from biological materials (living or once living). Optionally, a sample can be purified, partially purified, unpurified, enriched or amplified. Where a sample is purified or enriched, the sample can comprise principally one component, e.g., nucleic acid. More specifically, for example, a purified or amplified sample can comprise total cellular RNA, total cellular mRNA, cDNA, cRNA, or an amplified product derived there from.

The sample used in the methods of the invention can be from any source, and is not limited. Such sample can be an amount of tissue or fluid isolated from an individual or individuals, including, but not limited to, for example, skin, plasma, serum, whole blood, blood products, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc.

As used herein, the term "genome" refers to the total genetic information or hereditary material possessed by an organism (including viruses), i.e., the entire genetic complement of an organism or virus. The size of a genome is generally given as its total number of nucleotides or bases (when describing single-stranded genomes) or basepairs (when describing double-stranded genomes). A genome can comprise RNA or DNA. A genome can be linear, circular, and/or reside on discrete units such as chromosomes.

As used herein, the expression "sequence heterogeneity" refers to base sequence divergence between two or more homologous nucleotide sequences derived from different sources. Sequence divergence can be reflected in base pair incongruity (mismatches), gaps, insertions and/or genomic rearrangements. As used herein, one HCV genome, or a portion of the genome, can be aligned with a second (or more) HCV genome (or portion thereof) and analyzed for sequence heterogeneity. For example, a collection of viral genomes show sequence heterogeneity if they collectively show sequence divergence in a particular domain, e.g., in the 5'-UTR, or in a portion of the 5'-UTR.

As used herein, the expression "hepatitis C virus type" refers to the categorization of a hepatitis C virus (HCV) based on its genomic organization (e.g., phylogenetic analysis). The categorization of an HCV isolate into a particular type category reflects its genomic relatedness to other HCV isolates and its relatively lesser relatedness to other HCV isolates. As used herein, HCV typing nomenclature is consistent with the widely adopted nomenclature proposed by Simmonds et al (1994) Letter, Hepatology 19:1321-1324. See, also, Zein (2000) "Clinical Significance of Hepatitis C Virus Genotypes," Clinical Microbiol. Reviews 13(2):223-235; Maertens and Stuyver (1997) "Genotypes and Genetic Variation of Hepatitis C Virus," p. 182-233, In Harrison, and Zuckerman (eds.), *The Molecular Medicine of Viral Hepatitis*, John Wiley & Sons, Ltd., Chichester, England.). The system of Simmonds et al (1994) places the known HCV isolates into one of eleven (11) HCV genotypes, namely genotypes 1 through 11. Each genotype is further subdivided into groupings termed subtypes that reflect relatedness among strains of the same genotype. An HCV subtype is written by a lowercase roman letter following the genotype, e.g., subtype 1a, subtype 1c, subtype 6a, etc. Genetic variants found within an individual isolate are termed quasispecies. Approximately 78 HCV subtypes encompassing all 11 genotypes are known worldwide; the number of subtypes is not static; as more HCV isolates are studied and sequenced, it is likely that additional subtypes (and possibly genotypes) may be recognized.

As used herein, the term "virus types" can refer to either genotypes or subtypes. It is noted that as used herein, the term "HCV type" can mean HCV genotype or HCV subtype. As used herein, the term "HCV typing" means assigning the experimental (e.g., unknown type) HCV to a known genotype (e.g., 1, 2, 3, 4, 5 or 6, or a subset thereof) or assigning the experimental HCV to a known subtype (e.g., 1a, 1b, 1c, 2a, 2b, 2c, etc., or a subset thereof). In contrast, it is also noted that as commonly used in the art, the term "HCV genotyping" most frequently refers to assigning an HCV to one of any subtype of HCV, e.g., most typically, 1a, 1b, 1c, 2a, 2b, 2c, etc. However, as used herein, the term "genotyping" refers to assignment only to 1, 2, 3, 4, 5 or 6.

Some reports (see, e.g., Robertson et al., (1998) Arch. Virol., 143(12):2493-2503) suggest that viral genomic organization is best represented by the creation of viral clades, reflecting the observation that some HCV genotypes are more closely related to each other than to other HCV genotypes. In this system, clades 1, 2, 4 and 5 correspond to genotypes 1, 2, 4 and 5, while lade 3 comprises genotypes 3 and 10, and clade 6 comprises genotypes 6, 7, 8, 9 and 11. The description of the present invention does not use the lade nomenclature.

As used herein, the expression "functional probe" refers to an HCV typing probe, wherein when that probe forms hybridization complexes with at least five different HCV genotypes (e.g., genotypes selected from 1, 2, 3, 4, 5 and 6) or at least six different HCV subtypes (e.g., subtypes selected from 1a, 1b, 1c, 2a, 2b, 2c, 3a, 4a, 5a and 6a), different values or defining characteristics of some hybridization property can be distinguished corresponding to each HCV type, and therefore, the probe can distinguish each HCV type.

As used herein, the expression "non-functional probe" refers to an HCV typing probe, wherein when that probe forms hybridization complexes with at least five different HCV genotypes (e.g., genotypes selected from 1, 2, 3, 4, 5 and 6) or at least six different HCV subtypes (e.g., subtypes selected from 1a, 1b, 1c, 2a, 2b, 2c, 3a, 4a, 5a and 6a), different values or defining characteristics of some hybridization property can not be distinguished for each hybridization complex, and therefore, the probe can not distinguish each of the HCV genotypes or HCV subtypes.

As used herein, the expression "derived from" refers to a component that is isolated from or made using a specified sample, molecule, organism or information from the specified molecule or organism. For example, a nucleic acid molecule that is derived from a hepatitis C virus can be a molecule of the HCV genome, or alternatively, a transcript from the HCV genome.

As used herein, the expression "viral load," "viral burden," "viral copy number" and equivalent or similar expressions refer to the quantitative evaluation of a virus genome in a sample. A viral load can be expressed as the number of viral particles (e.g., virion) per unit of sample volume. Alternatively, a viral load can be expressed as the number of viral genome particles in a sample per unit of volume. For example, the viral load of an HCV in a sample can be expressed as the number of RNA genome molecules per unit of sample volume.

As used herein, the terms "subsequence," "fragment" or "portion" and the like refer to any portion of a larger sequence (e.g., a polynucleotide or polypeptide sequence), up to and including the complete sequence. The minimum length of a subsequence is generally not limited, except that a minimum length may be useful in view of its intended function. For example, a polynucleotide portion can be amplified from a viral genome to produce an amplicon, which in turn can be used in a hybridization reaction that includes a polynucleotide probe. Thus, in this case, the amplified portion should be long enough to specifically hybridize to a polynucleotide probe. Portions of polynucleotides can be any length, for example, at least 5, 10, 15, 20, 25, 30, 40, 50, 75, 100, 150 or 200 nucleotides or more in length.

As used herein, the term "monitor" refers to periodic or continuous surveillance, testing, data collecting and/or quantitation. Monitoring can be automated, and the information (e.g., a dataset) gathered during the monitoring can be printed or can be compiled as a computer readable and/or computer storable format.

As used herein, the term "correlate" refers to making a relationship between two or more variables, values or entities.

If two variables correlate, the identification of one of those variables can be used to determine the value of the remaining variable.

As used herein, the term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components. In some embodiments, the present invention provides kits for "closed-tube" HCV typing employing RT-PCR. These kits can include, for example but not limited to, reagents for sample collection (e.g., the collection of a blood sample), reagents for the collection and purification of RNA from blood, a reverse transcriptase, primers suitable for reverse transcription and first strand and second strand cDNA synthesis to produce an HCV amplicon, a thermostable DNA-dependent DNA polymerase and free deoxyribonucleotide triphosphates. In some embodiments, the enzyme comprising reverse transcriptase activity and thermostable DNA-dependent DNA polymerase activity are the same enzyme, e.g., *Thermus* sp. ZO5 polymerase or *Thermus thermophilus* polymerase.

BRIEF DESCRIPTION OF THE FIGURES

FIG. 2 provides a table describing HCV typing nomenclature.

FIG. 3 provides a table showing the percentages of nucleotide sequence identity between various HCV subtypes in a 222-nucleotide segment derived from the NS5 region at positions 7975 to 8196 of the prototype HCV viral genome.

FIG. 4 provides a table listing various HCV subtypes and examples of known isolates.

FIG. 5 provides a table listing various HCV types, and the consensus nucleotide sequences of a 33 nucleotide domain in the 5'-UTR region of each of the respective subtypes.

FIG. 6 provides a table listing selected HCV typing probes, their length (in nucleotides), and their respective base sequences. Functional probes, as well as three examples of non-functional probes, are provided.

FIG. 7 provides a table listing some of the probes described in FIG. 6 with their predicted and experimentally observed $T_m$ values for hybridization complexes comprising the probes and the indicated HCV types. The experimentally observed $T_m$ values were obtained in melting analysis experiments using RT-PCR amplicons generated from RNA template from in vitro transcribed HCV genomic material.

FIG. 8 provides examples of structures of thiazine dye soluble quenchers.

FIG. 17 is an expanded view of the data portrayed in FIG. 16.

DETAILED DESCRIPTION

Figure 1:
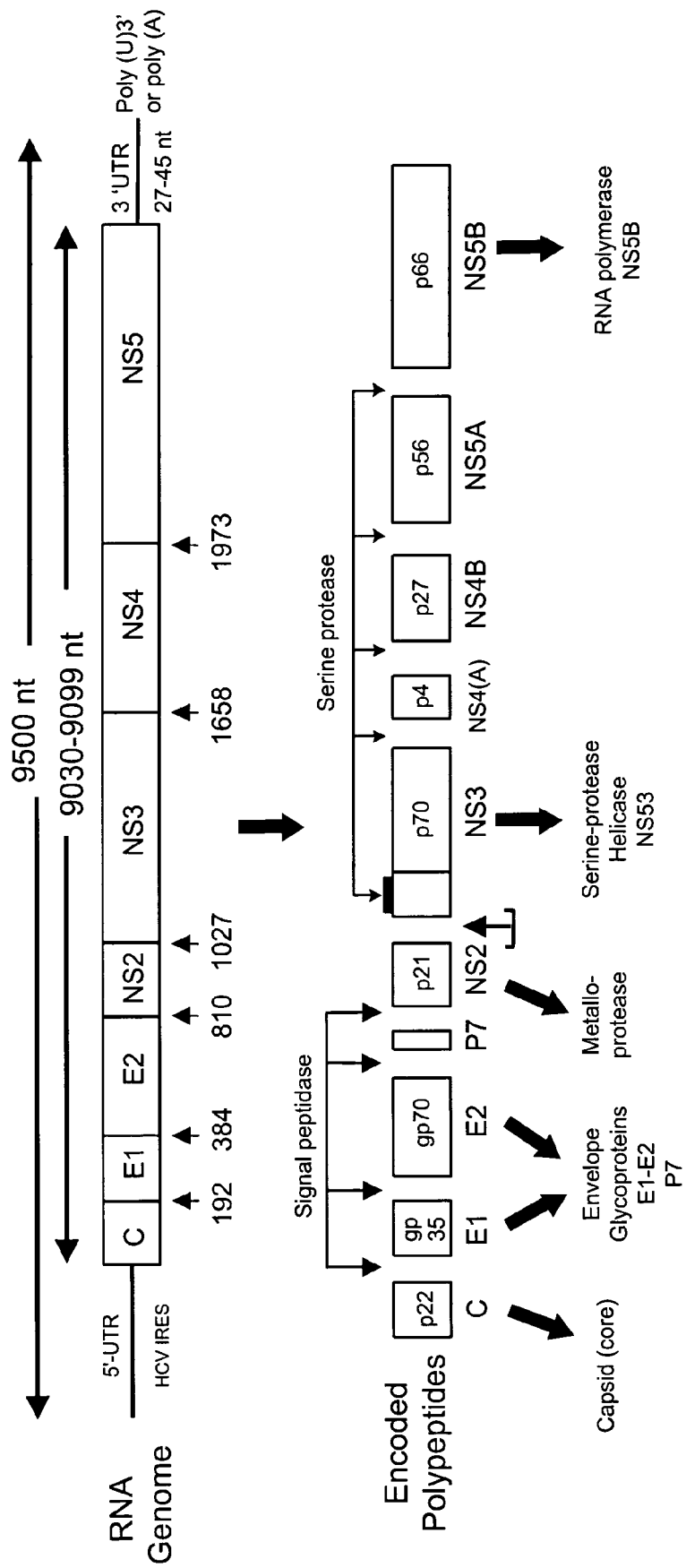
FIG. 1 provides a schematic representation of the HCV genome and the respective encoded polypeptides. Approximate lengths of the full length genome and the open reading frame are given. Polyprotein cleavage sites are also indicated. Exact sizes of the various genomic domains will vary depending on the HCV genotype and subtype.

The typing of an HCV isolate (for example, in a sample from a patient) is a valuable clinical tool in determining a most appropriate course for therapy. Knowing the type (genotype and/or subtype) of the HCV in an infection also has other benefits, including epidemiological analysis (e.g., determining the source and/or spread of a particular HCV outbreak).

Current methods for HCV typing face various limitations. For the purpose of providing improved methods for HCV typing to overcome present limitations in the art, and to provide compositions and methods that fulfill currently unmet needs, and also provide typing methods that have additional benefits, the present application provides compositions and methods for HCV typing analysis, where the methods described herein require only a single probe to assign an HCV in a sample to one of at least five genotypes or one of at least six subtypes (for example, the six most common HCV subtype isolates). The use of a single probe to assign an HCV-containing sample to an HCV type selected from at least five HCV genotypes or from at least six subtypes provides advantages over methods currently known in the art.

HCV Typing Using a Single Typing Probe

This present invention provides compositions and methods for HCV typing, where the methods used require only a single probe to make an HCV genotype or subtype assignment. The compositions and methods of the invention can be used to assign an HCV to one of at least five HCV genotypes (for example, selected from genotypes 1, 2, 3, 4, 5 or 6), or assign an HCV to one of at least six subtypes (for example, selected from subtypes 1a/b/c, 2a/c, 2b, 3a, 4a, 5a or 6a). The methods of the invention can also be used in cases of mixed HCV infection, with each HCV species present in the sample is assigned to an HCV type (genotype or subtype).

The present invention, namely compositions and methods related to using a single probe to make an assignment to a genotype selected from one of at least five HCV genotypes or one of at least six subtypes, provides advantages over methods for HCV typing currently known in the art, which require the use of multiple probes to make a genotype or subtype assignment, or where the probe is unable to differentiate from among more than five genotypes or six subtypes.

Generally, in one aspect, the HCV typing methods of the invention comprise the steps outlined below:

(A) Optionally, Amplifying a Portion of the HCV Genome from a Sample.

In some embodiments, a sample comprising a hepatitis C virus of unknown type is used directly in the typing analysis (without the need for an amplification step). In this case, HCV genomic material, or alternatively HCV transcripts, can optionally be isolated from the sample, for example, using any suitable nucleic acid isolation technique. That isolated material can be used in the subsequent analysis. Techniques for the analysis of (e.g., fluorescence detection of) nucleic acids with very low copy number are known in the art and find use with the invention. See, for example, Mirkin et al., "PCR-Less detection of genomic DNA with nanoparticle probes," Abstracts of Papers, 222nd ACS National Meeting, Chicago, Ill., United States (Aug. 26-30, 2001).

In some embodiments, an HCV amplification step is optionally employed prior to the typing analysis. This amplification is typically by an asymmetric RT-PCR reaction, where the region amplified encompasses a domain of sufficient variability such that each type (genotype or subtype) hypothetical amplicon shows unique nucleotide sequences relative to the other types. The region that is amplified is not particularly limited, and can be from any suitable part of the viral genome. The amplified region can reside in what is recognized to be a highly conserved region (e.g., the 5'-UTR region) or a hypervariable region (e.g., the NS5B region that encodes the HCV polymerase) Alternatively, the core or E1 regions can also be used. In some embodiments, the PCR primers used to generate the HCV amplicon are "universal primers," where the primers will generate an amplicon regardless of the HCV genotype or subtype. Universal type HCV primers (and HCV-specific PCR kits) suitable for generating universal HCV amplicons are widely known, and are also commercially available (see, e.g., Roche COBAS AMPLICOR™ HCV MONITOR test kit (Roche Molecular Systems, Inc, Pleasanton, Calif.). In other embodiments, two or more sets of primers can be used.

The DNA polymerase used in the PCR reactions is not particularly limited. As the PCR amplicon is generated from HCV RNA genomic material, the PCR reaction can be a one step reverse transcription (RT) PCR reaction using a thermo-stable polymerase that also has RT activity (e.g., *Thermus* sp. strain ZO5, Roche Molecular Systems). Alternatively, the RT-PCR can be a stepwise reaction using two different enzymes, one for the reverse transcription step to generate a cDNA, and the other for the amplification step. In certain embodiments, one of the PCR amplification primers also serves to prime the RT activity to create an HCV cDNA first strand. PCR and RT-PCR reagents and methods are routine widely known in the art.

The RT-PCR reaction can optionally contain dUTP in place of dTTP, and in a higher molar concentration than the other deoxyribonucleotides. This can be used for the generation of dUTP-containing amplicons, useful for preventing cross contamination of PCRs with exogenous DNA. In systems utilizing dUTP-containing amplicons, a uracil N-glycosylase (UNG) nuclease digest followed by UNG inactivation prior to HCV reverse transcription and amplification can eliminate cross-contamination from other dUTP-containing polynucleotides. Such systems are commonly used in the art, and are available from various sources (see, e.g., Roche Diagnostics AmpErase®).

In one aspect, the sample is a blood or blood product (e.g. plasma) sample from a patient, where the patient is proven to have an HCV infection, or is suspected of having an HCV infection. Typically, but not a requirement, a sample is at least partially purified for the purpose of enriching the RNA component of the sample, which will contain the HCV genomic material. Any suitable RNA purification method can be used, and can be either total RNA purification or polyA RNA purification. Preferably, the method used to enrich the RNA is a rapid method that can be applied in a manner suitable for use in high-throughput methodologies or robotic systems. For example, the QIAamp® Viral RNA Mini Kit (QIAGEN N.V. Venlo, the Netherlands) and the High Pure RNA Isolation Kit (Roche Applied Sciences, Indianapolis, Ind.).

(B) Hybridizing the HCV Material with a First Probe to form a Target Hybridization Complex.

The HCV material (e.g., isolated sample material or an HCV amplicon generated from the RT-PCR amplification) is then used in a hybridization reaction with an HCV typing probe to form a hybridization complex. The HCV typing probe is designed with various considerations, including (i) the probe sequence is at least partially complementary to a nucleotide sequence within the HCV amplicon, where there is sufficient complementarity to allow hybridization under at least non-stringent conditions; (ii) the region of hybridization complex complementarity shows sequence heterogeneity (e.g., at least one nucleotide difference) among at least five HCV genotypes or at least six HCV subtypes; (iii) hybridization complexes comprising the typing probe and the at least five HCV genotypes or the at least six virus subtypes have a distinguishing hybridization property that differentiates each from the remaining types.

Thus, when the probe forms a hybridization complex with a particular HCV genotype or subtype, the resulting hybridization complex has a unique property(ies) that is characteristic of that particular genotype or subtype, and is different from the property(ies) of hybridization complexes it can form with other genotypes or subtypes.

In some embodiments, the distinguishing hybridization property is a melting temperature ($T_m$). Methods for the in silico prediction and experimental determination of Tm's are well known to one of skill in the art. However, it is not intended that the invention be limited to the use of Tm as the only distinguishing hybridization property. Other techniques can also be used for distinguishing differences between hybridization complexes. For example, the distinguishing hybridization property can be $T_{25}$ or $T_{75}$. In other embodiments, different hybridization complexes (e.g., comprising an HCV typing probe) can be differentiated from each other by using heteroduplex mobility analysis (HMA), denaturing HPLC (DHPLC), cleavase fragment length polymorphism (CFLP) or thermal gradient capillary electrophoresis (TGCE). In addition, different distinguishing hybridization properties can be combined to enhance resolution of the hybridization complex. Examples of functional probes are provided in FIG. 6.

As noted in FIG. 6 and EXAMPLE 6, probe sequences are provided that also indicate the fluorescent labels as part of the sequences. For example, character "F" in FIG. 6 indicates the label "FAM." However, it is not intended that the base sequences of these probes be limited to the FAM label. One of skill recognizes that any of a variety of labels known in the art finds use with the base sequences of these probes.

As used in the invention, it is not intended that the term hybridization be limited to soluble-phase hybridizations. One of skill in the art recognizes that a variety of alternative hybridization methodologies find use with the invention. For example, solid phase hybridization techniques may be performed on a variety of surfaces, including membranes, filter papers, beads, gels, and the like. The hybridization probes may be covalently or non-covalently attached to the surface of the solid phase. Alternatively, a capture oligonucleotide may hybridize to a portion of the hybridization probe not involved in formation of the HCV hybridization complex, or a capture antibody specific for such a portion of the hybridization probe may be attached to the solid phase.

(C) Measuring the Hybridization Property of the Hybridization Complex.

Once the hybridization complex between the HCV amplicon and the HCV typing probe is formed, the distinguishing hybridization property is measured. In one aspect, as discussed above, the hybridization property is a Tm, and a Tm melting curve analysis is conducted. However, it is not intended that the invention be limited to the use of Tm as a distinguishing property. Indeed, the use (measurement) of other properties, either alone or in combination, can be advantageous, especially for high throughput applications.

In some embodiments (when, e.g., Tm is used as a distinguishing property), the RT-PCR reaction, the probe/target hybridization reaction and the measurement of the Tm is done in a single, "closed tube" system without the need for addition of any further reagents after the initiation of the RT-PCR reaction. In the closed tube system, all reagents necessary for each step are present in the tube from the outset of the analysis. For example, the closed tube RT-PCR and Tm system will contain the RNA sample, universal RT-PCR primers, the DNA polymerase (preferably with RT activity), deoxyribonucleotides, a suitable HCV typing probe (optionally where the probe is labeled with one or more suitable FRET components) and optionally a soluble FRET quencher. In certain embodiments, the closed tube RT-PCR and Tm system can be placed in a suitable thermocycler, and the progression of the RT-PCR, hybridization and Tm melting curve analysis is controlled simply by controlling the temperature of the reaction vessel, without the need to move the reaction vessel for different stages of the reactions and analysis. Similarly, in some embodiments, the thermocycler is coupled with a suitable fluorescence spectrophotometer so that a melting/annealing curve analysis fluorescence monitoring can be done without moving the reaction vessel.

It is not intended that the invention be limited to any particular method for the determination of Tm. Methods for the experimental determination of $T_m$ are widely known in the art and are described in a variety of sources, e.g., Liew et al., "Genotyping of Single-Nucleotide Polymorphism by High-Resolution Melting of Small Amplicons," Clinical Chemistry 50(7):1156-1164 (2004); Reed and Wittwer "Sensitivity and Specificity of Single-Nucleotide Polymorphism Scanning by High-Resolution Melting Analysis," Clinical Chemistry 50(10):1748-1754 (2004); Zhou et al., "Closed-Tube Genotyping with Unlabeled Oligonucleotide Probes and a Saturating DNA Dye," Clinical Chemistry 50(8):1328-1335 (2004); and Zhou et al., "High-resolution DNA melting curve analysis to establish HLA genotypic identity," Tissue Antigens 64:156-164 (2004). Melting curve analysis instrumentation is commercially available from a variety of manufacturers. It is recognized that different melting curve instrumentation can have different sensitivities. For example, one instrument may be able to resolve $T_m$ to ±0.5° C., whereas a different apparatus may be able to resolve $T_m$ to ±0.1° C. Thus, one HCV typing probe that is able to theoretically yield $T_m$ values of each HCV type with a separation of 0.2° C. can be used effectively on one make and model of $T_m$ instrumentation, but not on another HCV instrumentation that does not have the required sensitivity.

(D) Correlating the Measured Hybridization Property (e.g. $T_m$) with an HCV Type.

Once the hybridization property has been measured as described in (C), that information is used to assign an HCV type to the HCV in the sample, based on the value of the hybridization property that was measured. For example, when Tm is the measured distinguishing property, a table of standardized Tm values is assembled prior to analysis of the experimental sample. The standardized Tm table will consist of Tm values predetermined for each HCV genotype or subtype under the same hybridization conditions used in the analysis of the experimental sample. Once the Tm value for the experimental sample is measured, that value is compared to the standardized table of $T_m$ values. Identical or near identical values for the standardized and experimental samples indicates a correspondence between that standard type and the experimental type.

Alternatively, standardized samples of each HCV genotype or subtype can be analyzed in parallel with the experimental sample, and an HCV type assignment can be made based on comparing the experimental value with the standard values (e.g., the $T_m$ values) measured at the time of the assay.

In some embodiments, the methods for HCV typing are coupled to methods for determining HCV viral load. The combination of qualitative (typing) and quantitative (viral concentration) HCV analyses in the same assay is a great benefit to the clinician who is treating a patient. Methods for HCV quantitation are well known in the art, e.g., COBAS AMPLICOR™ HCV MONITOR Kit (Roche Molecular Systems, Inc., Pleasanton, Calif.). These commercial systems typically use a TaqMan-type probe in a PCR reaction to monitor the real-time accumulation of a universal HCV amplicon in an RT-PCR reaction.

The rate of PCR amplicon accumulation, as monitored by TaqMan probe fluorescence, is directly proportional to the amount of RNA genome starting material in a sample. By inclusion of appropriate HCV concentration standards in a TaqMan PCR reaction, it can be determined how many HCV genome molecules were present in the starting reaction. With that knowledge, the concentration of HCV genome particles in the experimental sample can be extrapolated.

In some embodiments of the invention, a TaqMan-type probe is included in the RT-PCR reaction mix, and the real-time accumulation of PCR amplicon is monitored. From that information, the concentration of HCV genome in the sample is calculated. In certain embodiments, the HCV quantitation is coupled with the HCV genotyping in a closed-tube system, where the TaqMan-type probe is included in the reaction mix that contains all the reagents for RT-PCR amplification and hybridization characterization (e.g., Tm melting curve analysis). When the quantitative HCV analysis is coupled with the HCV typing, an asymmetric PCR reaction is typically used in the RT-PCR amplification reaction. In that case, the TaqMan-type detection probe is designed to be complementary to the limiting amplicon strand, and the HCV typing probe is designed to be complementary to the abundant excess amplicon strand. Furthermore, the TaqMan quantitation probe is designed to hybridize to a conserved region of the HCV amplicon so that the probe will hybridize to the genome of any HCV type. In certain embodiments, the probe will hybridize to all HCV type amplicon sequences with equal affinity. Viral load calculations can be made using fluorescence derivative plots (e.g., first derivative and second derivative plots).

DESIGN OF HCV TYPING PROBES OF THE INVENTION

Generally, HCV typing probes of the invention are designed using the following guidelines:

1) Identify HCV Genome Candidate Targets Showing Heterogeneity Among at Least Five HCV Genotypes or at Least Six HCV Subtypes.

The HCV target sequences for hybridization are not particularly limited. The probe can hybridize to relatively conserved domains that have sufficient heterogeneity (e.g., the 5'-UTR) or reside within more variable domains in the HCV genome. When a suitable probe target is identified, the use of proper universal amplification primers is also considered, where the HCV amplicon must contain the probe target sequence, but also, sequences that flank the probe target sequence must be sufficiently conserved to allow the use of universal PCR primers that will generate an HCV amplicon regardless of the HCV type. A candidate HCV typing probe is designed that will hybridize to the region of heterogeneity.

Various commercial programs are widely available for the design of hybridization probes. Examples of such commercially available programs include Visual OMP (DNA Software, Inc., Ann Arbor, Mich.), and the $T_m$ utility tool from Idaho Technology, Inc. (Salt Lake City, Utah). It is not intended that the invention be limited to the use of any particular software for designing probe sequences.

It is not a requirement that an HCV typing probe of the invention have a nucleotide sequence that is identical (100% complementary) to any one HCV type. An HCV typing probe of the invention can have a nucleotide sequence that is intentionally less than 100% complementary to each HCV genome type. That case may be desirable for the purpose of giving that probe desired hybridization properties that will allow the probe to distinguish between each of the HCV types. For example, mismatches can be intentionally designed into a probe for the purpose of changing the $T_m$ of the resulting hybridization complex. Examples of functional HCV typing probes are provided in FIG. 6.

2) Test Candidate Typing Probe Sequences in Silico.

Once a candidate probe sequence is identified, that sequence is optionally tested in silico for its ability to display a differentiating property when hybridized to each of the known HCV type sequences. For example, when a candidate probe sequence is identified, in silico modeling can be used to predict the $T_m$ of the hypothetical hybridization complexes with that probe and the complementary target in each of the known HCV types. An effective probe candidate must display a sufficiently distinguishing property (e.g., $T_m$) with each of the HCV types to be effective.

Various commercial programs are widely available for the prediction of $T_m$ of a particular hybridization complex. For example, Visual OMP (DNA Software, Inc., Ann Arbor, Mich.), and the $T_m$ utility tool from Idaho Technology, Inc. (Salt Lake City, Utah). It is not intended that the invention be limited to the use of any particular software for predicting $T_m$. Examples of predicted (and experimentally observed) $T_m$ values for various probes is shown in FIG. 7.

The in silico testing of the candidate HCV typing probes is for initial guidance in identifying effective versus ineffective probes. The in silico screening is not strictly required before proceeding to the step of experimental testing and measuring the hybridization properties of the HCV typing probes. Furthermore, it is understood that in silico prediction of $T_m$ values is only an approximation, and experimental observation and confirmation is required.

3) Test Candidate Probes In Vitro.

As a final step in probe design, the typing probe is tested in vitro for its ability to distinguish each HCV type. This step is necessary to confirm the results of the in silico prediction, which does not have 100% accuracy in predicting probe behavior. In some embodiments where $T_m$ values are determined, the probe is used in melting curve analyses with artificial synthetic HCV targets (chemically synthesized) that have nucleotide sequences corresponding to each HCV type. The $T_m$ for each hybridization complex that includes the typing probe and each HCV synthetic template is determined experimentally. The RT-PCR reaction to generate an HCV amplicon is not required in these assays. A functional (successful) probe is a probe that yields a different and distinguishable $T_m$ value for each of at least five HCV genotypes or at least six HCV subtypes. The experimental determination of $T_m$ values using synthetic (chemically synthesized) HCV templates is described in EXAMPLE 1. FIG. 7 shows the experimentally observed $T_m$ values for various probes. These probes showed sufficient separation of experimentally observed $T_m$ values with each of the HCV synthetic templates.

A second level of verification testing can optionally be used. For example, the $T_m$ melting curve analysis using artificial templates described above can be adapted to use synthetic transcripts (enzymatically synthesized, e.g., by in vitro transcription) from known HCV isolates in place of the chemically synthesized artificial templates. For example, artificial transcripts can be produced by in vitro transcription from plasmids carrying HCV genomic inserts of known genotype and subtype (see EXAMPLES 2 and 3).

An example of comparisons between predicted and experimentally observed Tm values is shown in FIG. 7. The experimentally observed $T_m$ values were obtained in melting analysis experiments using RT-PCR amplicons generated from RNA template from in vitro transcribed HCV genomic material.

Probe and Primer Synthesis

The invention also provides a number of probes and primers, for example, HCV typing probes, HCV quantitation (TaqMan®-type) probes and HCV amplification primers (for use in RT-PCR). It is not intended that the methods used to produce these probes and primers be in any way limited. One of skill in the art is well familiar with the wide variety of chemical synthesis strategies and reagents for producing probes and primers.

Also, it is not intended that the HCV typing probes and primers of the invention be limited to naturally occurring nucleotide structures or naturally occurring bases (e.g., adenine, guanine, thymine, cytosine, and uracil). In addition to the naturally occurring heterocyclic bases that are typically found in nucleic acids, non-natural nucleic acid analogs also find use with the invention. Non-natural analogs include those having non-naturally occurring heterocyclic or other modified bases. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) Helv. Chim. Acta 82:1640. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 7-deazaadenine, 2-methyladenine, 2-methylguanine, 3-methylcytosine, 5-methylcytosine, N6-methyladenine, 7-methylguanine, 7-deazaguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like. To further illustrate, other examples of modified oligonucleotides include those having one or more locked nucleid acid (LNA™) monomers (oligonucleotides comprising LNA™ monomers available from, e.g., Link Technologies, Ltd., Lanarkshire, Scotland; under license from Exiqon A/S, Vedbaek, Denmark). Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

Oligonucleotide probes and primers can be prepared using any technique known in the art. In certain embodiments, for example, the oligonucleotide probes and primers are synthesized chemically using any nucleic acid synthesis method, including, e.g., according to the solid phase phosphoramidite method described by Beaucage and Caruthers (1981) *Tetrahedron Letts.* 22(20):1859-1862, which is incorporated by reference. To further illustrate, oligonucleotides can also be synthesized using a triester method (see, e.g., Capaldi et al. (2000) "Highly efficient solid phase synthesis of oligonucleotide analogs containing phosphorodithioate linkages" *Nucleic Acids Res.* 28(9):e40 and Eldrup et al. (1994) "Preparation of oligodeoxyribonucleoside phosphorodithioates by a triester method" *Nucleic Acids Res.* 22(10): 1797-1804, which are both incorporated by reference). Other synthesis techniques known in the art can also be utilized, including, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications as described herein or as otherwise known in the art.

Probes utilized in the reaction mixtures, methods, and other aspects of the invention are typically labeled to permit detection of probe-target hybridization duplexes. Labels can be attached to oligonucleotides directly or indirectly by a variety of techniques known in the art. To illustrate, depending on the type of label used, the label can be attached to a terminal (5' or 3' end of an oligonucleotide primer and/or probe) or a non-terminal nucleotide, and can be attached indirectly through linkers or spacer arms of various sizes and compositions. Using commercially available phosphoramidite reagents, one can produce oligonucleotides containing functional groups (e.g., thiols or primary amines) at either the 5' or 3' terminus via an appropriately protected phosphoramidite, and can label such oligonucleotides using protocols described in, e.g., Innis et al. (Eds.) *PCR Protocols: A Guide to Methods and Applications*, Elsevier Science & Technology Books (1990)(Innis), which is incorporated by reference.

Essentially any nucleic acid (standard or non-standard, labeled or non-labeled) can be custom or standard ordered from any of a variety of commercial sources, such as The Midland Certified Reagent Company (Midland, Tex.), Operon Technologies Inc. (Huntsville, Ala.), Proligo LLC (Boulder, Colo.), and many others.

Labels

The invention also provides a number of probes to be used in conjunction with the invention, for example, HCV typing probes and HCV quantitation (TaqMan-type) probes. As probes, these molecules typically comprise a suitable label. It is not intended that the label, label detection system or instrumentation for label detection and quantitation be limited in any way. One of skill in the art is well familiar with the wide variety of labeling strategies and reagents for producing suitably labeled polynucleotides.

Labels can, alternatively or in combination: (i) provide a detectable signal; (ii) interact with a second label to modify the detectable signal provided by the second label, e.g., FRET; (iii) stabilize hybridization, i.e., duplex formation; (iv) confer a capture function, i.e., hydrophobic affinity, antibody/antigen, ionic complexation, or (v) change a physical property, such as electrophoretic mobility, hydrophobicity, hydrophilicity, solubility, or chromatographic behavior. Labeling can be accomplished using any one of a large number of known techniques employing known labels, linkages, linking groups, reagents, reaction conditions, and analysis and purification methods. Labels include light -emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28).

Essentially any labeling moiety is optionally utilized to label a probe and/or primer by techniques well known in the art. In some embodiments, for example, labels comprise a fluorescent dye (e.g., a rhodamine dye, e.g., R6G, R110, TAMRA, ROX, etc., see U.S. Pat. Nos. 5,366,860; 5,847,162; 5,936,087; 6,051,719; 6,191,278), a fluorescein dye (e.g., JOE, VIC, TET, HEX, FAM, etc.; 6-carboxyfluorescein; 2',4', 1,4, -tetrachlorofluorescein; and 2',4',5',7', 1,4-hexachlorofluorescein; see U.S. Pat. Nos. 5,188,934; 6,008,379; 6,020, 481), benzophenoxazines (U.S. Pat. No. 6,140,500), a halofluorescein dye, a cyanine dye (e.g., CY3, CY3.5, CY5, CY5.5, CY7, etc., see Published International Application No. WO 97/45539 by Kubista), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIG-DYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc.

FRET labeling techniques are commonly used in both real-time amplicon quantitation and for monitoring nucleic acid probe hybridization. In some preferred embodiments, FRET label systems are used with the probes of the invention. It is not intended that the invention be limited to any particular FRET pair system. One of skill in the art recognizes the wide range of FRET labels that can be used with the probes of the invention. Fluorescent energy-transfer dye pairs of donors and acceptors include, e.g., U.S. Pat. Nos. 5,863,727; 5,800, 996; 5,945,526, as well as any other fluorescent label capable of generating a detectable signal.

Whether a fluorescent dye is a label or a quencher is generally defined by its excitation and emission spectra, and the fluorescent dye with which it is paired. Fluorescent molecules commonly used as quencher moieties in probes and primers include, e.g., fluorescein, FAM, JOE, rhodamine, R6G, TAMRA, ROX, DABCYL, and EDANS. Many of these compounds are available from the commercial suppliers referred to above. Examples of non-fluorescent or dark quenchers that dissipate energy absorbed from a fluorescent dye include the Black Hole Quenchers™ or BHQ™, which are commercially available from Biosearch Technologies, Inc. (Novato, Calif., USA). Other quenchers include Iowa Black quenchers (e.g., Iowa Black FQ™ and Iowa Black RQ™) and Eclipse® Dark Quenchers (Epoch Biosciences, Inc, Bothell, Wash.).

The EXAMPLES provided herein describe HCV typing probes that are labeled with a FRET donor moiety, and are used in conjunction with a soluble quencher. However, it is not intended that the invention be limited to those types of probe configurations. For example, an HCV typing probe of the invention can be a molecular beacon type of probe, where the probe comprises both the donor and the quencher moieties, as known in the art. Alternatively, an HCV typing probe of the invention can be a TaqMan type probe, also where the probe comprises both donor and quencher moieties (but does not necessarily have an intervening stem structure and does not get cleaved by a polymerase with exonuclease activity).

Alternatively, the donor-labeled HCV typing probes of the invention can be used in conjunction with a quencher-labeled anchor probe in place of a soluble quencher. In this scenario, an anchor probe is designed to hybridize to a conserved HCV region immediately adjacent to the HCV typing probe, and where the anchor probe is labeled with a suitable quencher moiety. When both probes are hybridized to their respective targets, FRET donor quenching occurs. During conditions during the melting curve analysis, the HCV typing probe will eventually dissociate from its target sequence, leaving only the anchor probe bound to the HCV amplicon, resulting in an increase in donor fluorescence. Anchor probe FRET systems are known in the art, and are described, for example, in Schroter et al., (2002) Jour. Clin. Microbiol., 40(6):2046-2050.

Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, calorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. patent application Ser. No. 10/719,257, filed on Nov. 21, 2003, which references are each incorporated by reference.

Another class of labels are hybridization-stabilizing moieties which serve to enhance, stabilize, or influence hybridization of duplexes, e.g., intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81).

Yet another class of labels effect the separation or immobilization of a molecule by specific or non-specific capture, for example biotin, digoxigenin, and other haptens (Andrus, "Chemical methods for 5' non-isotopic labelling of PCR probes and primers" (1995) in PCR 2: A Practical Approach, Oxford University Press, Oxford, pp. 39-54).

Non-radioactive labelling methods, techniques, and reagents are reviewed in: Non-Radioactive Labelling, A Practical Introduction, Garman, A. J. (1997) Academic Press, San Diego.

In some embodiments, the two types of probes that are used in the invention, namely the HCV typing probe and the HCV quantitation probe, use the same label, for example, a fluorescein label. This provides various advantages, as the HCV quantitation assay and the HCV typing assay can be read in the same detector, e.g., a fluorescence spectrophotometer. However, it is not intended that the invention be limited to that type of configuration. For example, the two different probes can use two different fluorescent labels that have non-identical emission spectra (or even different labelling systems, such as fluorescent and non-fluorescent label systems).

Use of Soluble Quencher Technology

In some embodiments, FRET label systems are used with the probes of the invention, e.g., TaqMan-type probes and HCV quantitation probes. However, it is not intended that the invention be limited to the use of FRET donor/quencher systems. Indeed, FRET systems are merely a subset of possible energy transfer systems that find use with the invention (e.g., non-fluorescent energy transfer systems are known in the art), nor is the invention limited to any particular FRET pair system. In some embodiments, a FRET system that uses a soluble quencher is utilized.

As used herein, the expressions "soluble acceptor" or "soluble quencher" or the like refer to an acceptor moiety that is not attached to any other molecule, and is largely soluble or otherwise not bound to any other molecule or solid phase. In some embodiments, a soluble quencher can be part of a FRET pair, where the soluble quencher is a FRET quencher and can interact with a FRET donor in a functional FRET pair. For example, ethidium bromide and some thiazine dyes e.g., methylene blue, Azure A, Azure B, Azure C, thionin, and new methylene blue, can be used as soluble quenchers.

A thiazine dye soluble quencher acts by binding to double-stranded nucleic acid, but has reduced affinity for single-stranded nucleic acid. Without being bound to any particular theory, it is believed that the predominant binding mode is through intercalation, but minor and major groove binding is also possible depending on the sequence context and hybridization conditions (see, Rohs et al. (2000) J. Am. Chem. Soc., 122:2860-2866; and Tuite et al. (1994) J. Am. Chem. Soc., 116:7548-7556). Thus, the fluorescence donor label attached to a probe that forms a hybridization complex with a target polynucleotide is subject to a quenching effect by the intercalating soluble quencher that has an affinity for double-stranded nucleic acid due to the close proximity of the quencher to the donor moiety on the probe. If the solution containing the hybridization complex is heated (as in a melting curve analysis), the probe eventually dissociates from the target polynucleotide, thereby reducing the affinity of the quencher for the nucleic acid, resulting in reduced proximity of the soluble quencher to the probe donor and an increase in fluorescence from the donor. Thus, the formation/dissociation of hybridization complexes in a reaction can be monitored by the use of a FRET system having a soluble FRET quencher.

The concentration of the soluble quencher used in a particular HCV typing reaction is not limited, and ranges of effective concentrations will be apparent to one of skill in the art. For example, when using thiazine dye soluble quenchers, in some embodiments, a range defined by and including of 5 µg/mL and 100 µg/mL is contemplated. In some embodiments, a preferred range is 10-50 µg/mL, or alternatively, 10-25 µg/mL. Alternatively still, a concentration of 25 µg/mL of the thiazine dye soluble quencher is used.

Further detailed description of soluble light emission modifiers (e.g., soluble FRET quenchers) and the uses thereof is found in cofiled U.S. Utility Patent Appl. Serial No. 11/474,062, filed on Jun. 23, 2006, entitled "LIGHT EMISSION MODIFIERS AND THEIR USES IN NUCLEIC ACID DETECTION, AMPLIFICATION AND ANALYSIS," by Gupta and Will, the entire content of which is hereby incorporated by reference in its entirety for all purposes.

Closed System vs. Open System Typing Assays

The invention also provides methods for HCV typing, and also provides methods for concurrent HCV typing and HCV quantitation. In certain embodiments, the reactions for HCV typing and HCV typing/quantitation are "closed-tube" systems (see, EXAMPLES 3 and 5).

In the closed tube system, all reagents necessary for each step are present in the tube from the outset of the analysis. In contrast, an "open-tube" system requires the addition of a reagent(s) or additional component(s) after the start of the HCV typing analysis. Closed-tube systems have certain advantages over open-tube systems, since closed-tube systems reduce need for operator intervention and allow for highly parallel rapid throughput. Closed tube systems are also far preferable for commercial applications such as "kits," since the instructions provided to a kit user are simpler, contain fewer steps and the method has fewer possible opportunities where user-errors or contamination can be introduced. In some circumstances, open-tube systems can be advantageous, e.g., to enable use of incompatible reagents.

For example, in some preferred embodiments of the invention, the HCV typing and HCV quantitation concurrent analysis is run as a closed-tube system. In such a system, the reaction tube (or reaction well or chamber) will comprise from the outset, for example, the RNA sample, universal RT-PCR primers to generate the HCV amplicon, a DNA polymerase having RT activity, deoxyribonucleotides, a TaqMan®-type probe for HCV amplicon quantitation, a suitable HCV typing probe (optionally where the probe is labeled with a suitable FRET component), and a soluble FRET quencher. With these reagents in the tube, the reaction has all the components necessary for HCV amplicon production, real-time monitoring of HCV amplicon accumulation and the HCV melting curve $T_m$ analysis for the HCV type identification.

Kits and Articles of Manufacture

The present invention provides articles of manufacture, for example, kits, and in particular, diagnostic kits and kits for HCV genotyping. These kits provide the materials necessary for typing HCV infections, using the methods described herein. These kits find use for the clinician, who can use the HCV typing information in the clinic to predict responsiveness of a particular HCV infection to various treatments based on the virus type (e.g., the genotype or the subtype). The invention provides kits to facilitate the methods of the present invention, e.g., methods for typing the HCV in a sample.

Materials and reagents to carry out these methods can be provided in kits to facilitate execution of the methods.

In some embodiments, the kits are diagnostic kits, where the information obtained from performing the methods enabled by the kits is used to identify the type of HCV infection in a sample taken from a patient.

In certain embodiments, the invention provides kits suitable for "closed-tube" HCV genotyping employing RT-PCR, as described herein. In other embodiments, the invention provides kits suitable for closed-tube HCV typing employing RT-PCR with HCV quantitation.

The kits of the invention can provide any or all of the synthetic oligonucleotides used in methods described herein. For example, the kits can provide oligonucleotide primer(s) suitable for priming reverse transcription from an HCV RNA molecule to produce an HCV cDNA. The kits can provide amplification primers suitable for amplification of any suitable portion of the HCV genome, e.g., sequences in the 5'-UTR domain. The invention provides suitable HCV amplification primers that can be included in kits of the invention. It is understood that the invention is not limited to the primers recited herein, as any other suitable amplification primers also find use with the invention.

The kits of the invention can include oligonucleotide probes suitable for the HCV typing melting curve analysis. The invention provides a number of suitable probes, e.g., the functional probes provided in FIG. 6. It is understood, however, that the kits of the invention are not limited to the functional probes provided in FIG. 6, as the invention also provides guidance for the identification and synthesis of additional suitable probes. The probes provided in kits of the invention can be labeled or unlabeled. Optionally, an HCV typing probe provided with the kits of the invention can be labeled with a suitable FRET donor moiety, as known in the art. Optionally, an HCV typing probe provided with the kits of the invention can be a TaqMan-type probe, comprising both a donor and a quencher moiety (in this case, a soluble quencher will not be necessary). Optionally, kits of the invention can include a suitable soluble quencher, e.g., a thiazine dye such as new methylene blue. Optionally, any suitable FRET pair system can be provided in kits of the invention.

In some embodiments, the kits of the invention can include oligonucleotide probes suitable for HCV amplicon quantitation, e.g., TaqMan-type probes specific for HCV base sequences located within the HCV amplicon. For example, the invention provides HCV quantitation probe of SEQ ID NO: 41. It is understood, however, that the kits of the invention are not limited to this one quantitation probe, as one of skill in the art will recognize that the invention (and kits of the invention) can comprise any suitable quantitation probe.

In addition, kits of the present invention can also include, for example but not limited to, apparatus and reagents for sample collection and/or sample purification (e.g., isolation of RNA from a blood sample), sample tubes, holders, trays, racks, dishes, plates, instructions to the kit user, solutions, buffers or other chemical reagents, suitable samples to be used for standardization, normalization, and/or control samples (e.g., positive controls, negative controls or calibration controls). Kits of the present invention can also be packaged for convenient storage and shipping, for example, in a container having a lid. The components of the kits may be provided in one or more containers within the kit, and the components may be packaged in separate containers or may be combined in any fashion. In some embodiments, kits of the invention can provide materials to facilitate high-throughput analysis of multiple samples, such as multiwell plates that can be read in a suitable fluorescence spectrophotometer.

Detection/Correlation Systems of the Invention

In some embodiments, the invention provides integrated systems for correlating the detection of a signal with a hepatitis C virus type. The system can include instrumentation and means for interpreting and analyzing collected data, especially where the means for deriving the HCV type comprises algorithms and/or electronically stored information (e.g., collected fluorescence data, predetermined HCV type correlations, etc). Each part of an integrated system is functionally interconnected, and in some cases, physically connected. In some embodiments, the integrated system is automated, where there is no requirement for any manipulation of the sample or instrumentation by an operator following initiation of the HCV typing analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure hybridization of the HCV typing probe with the HCV target amplicon (during the melting curve analysis when Tm is being measured), and optionally, to measure accumulation of the HCV amplicon during HCV quantitation (e.g., with a TaqMan-type probe). A detector can be in the form of a multiwell plate reader to facilitate the high-throughput capacity of an HCV typing assay.

In some embodiments, the integrated system includes a thermal cycling device, or thermocycler, for the purpose of controlling the temperature of a reaction, e.g., during the phases of an RT-PCR reaction, or during melting analysis when $T_m$ is to be determined. In some embodiments, the thermal cycling device and the detector are an integrated instrument, where the thermal cycling and emission detection (e.g., fluorescence detection) are done in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the HCV type of the sample is determined (electronically). In some embodiments, the correlation module comprises a computer program that calculates the Tm based on the fluorescence readings from the detector and furthermore derives the HCV type of the unknown sample based on the fluorescence and Tm data.

In some embodiments, the correlation module compares the hybridization property (e.g., $T_m$) of the unknown sample with a database (or table) of values for known HCV types to make a correlation between the hybridization property of the unknown sample and the HCV type of the unknown sample.

In some embodiments, the correlation module in the system determines the type of an HCV, where the type is selected from one of five genotypes, or one of six subtypes. A correlation module can comprise, among other features, experimentally predetermined values for hybridization properties of hybridization complexes that contain known HCV types, or the correlation module can comprise predicted values for hybridization properties of hybridization complexes that contain known HCV types. Alternatively, the correlation module can rely on experimentally determined values for hybridization properties of hybridization complexes that contain known HCV types that are obtained at the same time as the experimental sample with the HCV of unknown type.

With a suitable correlation module and a suitable probe, a system of the invention can assign a type to an HCV in a sample, where the type is selected from more than five genotypes, and preferably, from as many as 11 or more genotypes. For example, depending on the instrumentation used, the Tm of a particular hybridization complex can be determined with a variable degree of accuracy. For example, some Tm apparatus (a combined thermal cycling apparatus and coupled fluorescence spectrophotometer) from one manufacturer can have an accuracy of ±1.0° C., while a second apparatus from a different manufacturer can have an accuracy of ±0.1° C. Use of the more sensitive apparatus will allow the differentiation of a greater number of HCV types if the Tm values are closely clustered together. Similarly, using suitably sensitive apparatus, there is the potential to be able to determine the type of an HCV in a sample, where the type can be assigned to far more than six subtypes, as there are as many as 78 or more known HCV subtypes.

A system of the invention is not limited to the use of $T_m$ as the sole distinguishing hybridization property of a hybridization complex. For example, HMA (heteroduplex mobility analysis), DHPLC (denaturing HPLC), CFLP (cleavase fragment length polymorphism), TGCE (thermal gradient capillary electrophoresis); SURVEYOR™ nuclease mutation detection kits, and SSCP (single strand conformation polymorphism), can all be used to distinguish hybridization complexes with different properties, and therefore, can be used to assign one or more type designation to an HCV sample.

A typical system of the invention can include one or more HCV typing probe (see, e.g., the functional probes provided in FIG. 6), one or more HCV quantitation probe (see, e.g., the quantitation probe of SEQ ID NO: 41), primers suitable for HCV amplification, a suitable detector (with or without an integrated thermal cycling instrument), a computer with a correlation module, and instruction (electronic or printed) for the system user. Typically, the system includes a detector that is configured to detect one or more signal outputs from the set of HCV typing probes and/or the HCV quantitation probes. In some embodiments, the HCV typing probe and the HCV quantitation probe have the same signal output (and therefore can use the same detector). In some embodiments, the system can further contain reagents used in the HCV typing or HCV typing/quantitation analysis. These can include but are not limited to one or more of a DNA polymerase with RT activity, suitable buffers, contamination control reagents (e.g., dUTP and/or UNG nuclease), stabilizing agents, dNTPs, soluble quenchers, etc. Kits can be supplied to operate in conjunction with one or more systems of the invention.

A wide variety of signal detection apparatus is available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used with the HCV typing and/or quantitation probes. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is commonly used for detection of amplified nucleic acids (however, upstream and/or downstream operations can also be performed on amplicons, which can involve other detection methods). In general, the detector detects one or more label (e.g., light) emission from a probe label.

The detector(s) optionally monitors one or a plurality of signals from an amplification reaction. For example, the detector can monitor optical signals which correspond to "real time" amplification assay results, as with the HCV quantitation (TaqMan-type) probe.

System instructions that correlate a detected signal with an HCV type (e.g., a genotype or a subtype) are also a feature of the invention. For example, the instructions can include at least one look-up table that includes a correlation between the detected signal and the HCV type. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the detected signal and the HCV type. The instructions also typically include instructions providing a user interface with the system, e.g., to permit a user to view results of a sample analysis and to input parameters into the system.

The system typically includes components for storing or transmitting computer readable data detected by the methods of the present invention, e.g., in an automated system. The computer readable media can include cache, main, and storage memory and/or other electronic data storage components (hard drives, floppy drives, storage drives, etc.) for storage of computer code. Data representing HCV types by the method of the present invention can also be electronically, optically or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a blood or blood products from a patient. The material comprising the sample can be isolated or partially purified or purified. In some aspects, the sample material comprises RNA, polyA RNA, cRNA, total RNA, cDNA, amplified cDNA, or the like.

The phrase "system that correlates" in the context of this invention refers to a system in which data entering a computer corresponds to physical objects or processes or properties external to the computer, e.g., a hepatitis C virus, and a process that, within a computer, causes a transformation of the input signals to different output signals. In other words, the input data, e.g., the fluorescence readings from a TM melting curve, is transformed to output data, e.g., the HCV type such as a genotype or a subtype. The process within the computer is a set of instructions, or "program," by which positive amplification or hybridization signals are recognized by the integrated system and attributed to individual samples as an HCV type. Additional programs correlate the identity of individual samples with phenotypic values, e.g., statistical methods. In addition there are numerous programs for computing, e.g., C/C++, Delphi and/or Java programs for GUI interfaces, and productivity tools (e.g., Microsoft Excel and/or SigmaPlot) for charting or creating look up tables of relevant HCV typing or HCV quantitation correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as Visual Basic are also suitably employed in the integrated systems of the invention.

For example, HCV typing probe $T_m$ values assigned to a particular HCV type can be recorded in a computer readable medium, thereby establishing a database corresponding Tm with unique HCV type (or a subset of HCV types). Any file or folder, whether custom-made or commercially available (e.g., from Oracle or Sybase) suitable for recording data in a computer readable medium can be acceptable as a database in the context of the invention. Data regarding HCV type analysis as described herein can similarly be recorded in a computer accessible database. Optionally, HCV typing data can be obtained using an integrated system that automates one or more aspects of the assay (or assays) used to determine the HCV type. In such a system, input data corresponding to HCV types can be relayed from a detector, e.g., an array, a scanner, a CCD, or other detection device directly to files in a computer readable medium accessible to the central processing unit. A set of system instructions (typically embodied in one or more programs) encoding the correlations between Tm and the HCV types can be then executed by the computational device to identify correlations between Tm and HCV type.

Typically, the system also includes a user input device, such as a keyboard, a mouse, a touchscreen, or the like, for, e.g., selecting files, retrieving data, reviewing tables of $T_m$ values, etc., and an output device (e.g., a monitor, a printer, etc.) for viewing or recovering the product of the statistical analysis.

Thus, in one aspect, the invention provides an integrated system comprising a computer or computer readable medium comprising set of files and/or a database with at least one data set that corresponds to predetermined or experimental $T_m$ values. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., samples) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support can be a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for HCV typing of the present invention can, thus, include a digital computer with one or more of high-throughput liquid control software, thermocycler control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes. The image scanner interfaces with the image analysis software to provide a measurement of, e.g., nucleic acid probe label intensity during HCV amplification or during HCV melting curve analysis, where the probe label intensity measurement is interpreted by the data interpretation software to show whether, and to what degree, the labeled probe hybridizes to a target. The data so derived is then correlated with sample identity, to determine the HCV type in a particular sample, and optionally, determine the load (e.g., concentration) of an HCV in a sample.

EXAMPLES

The following examples are offered to illustrate, but not to limit the claimed invention. One of skill will recognize a variety of non-critical parameters that may be altered and alternative reagents that can be utilized without departing from the scope of the claimed invention.

Example 1

HCV Probe Melting Curve Analysis (HCV Typing) Using Synthetic HCV Target Sequences The present example describes a melting curve analysis using one HCV typing probe and six synthetic templates derived from six different HCV types (shown in TABLE 1). The effectiveness of this probe to differentiate at least five genotypes and at least six subtypes was assessed.

A collection of suitable HCV typing probes were designed and synthesized. Each of these probes hybridizes to a domain within the 5'-UTR of the HCV genome showing sequence heterogeneity among at least five different genotypes and at least six different subtypes (see, FIG. 5). The probe AG0203A was used in the analysis (see probe sequence provided in FIG. 6; and SEQ ID NO: 8). The probe contained a single fluorescein (FAM) label. This probe was alternatively hybridized with each of the six different synthetic single-stranded templates corresponding to various HCV types. The sequences of these synthetic templates are the reverse complements of the HCV type consensus sequences shown in FIG. 5; these synthetic templates are shown in TABLE 1 below.

TABLE 1

| HCV Genotype/ Subtype | Synthetic Template | SEQ ID NO: |
|---|---|---|
| 1a/b | AGGACCCGGTCGTCCTGGCAATTCCGGTGTA | 33 |
| 2a/c | AGGACCCAGTCTTCCCGGCAATTCCGGTGTA | 34 |
| 3a | AGGACCCGGTCACCCCAGCGATTCCGGTGTA | 35 |
| 4a | AGGACCCGGTCATCCCGGCGATTCCGGTGTA | 36 |

TABLE 1-continued

| HCV Genotype/ Subtype | Synthetic Template | SEQ ID NO: |
|---|---|---|
| 5a | AGGACCCGGTCATCCCGGCAATTCCGGTGTA | 37 |
| 6a | AGGACCCGGTCATCCTGGCAATTCCGGTGTA | 38 |

The probe was annealed to each of the six synthetic templates in six separate reactions under the following conditions:

| Component | Concentration |
|---|---|
| poly rA carrier | 9 µg/mL |
| Glycerol | 6.2% |
| DMSO | 2.5% |
| Tricine, pH 8.3 | 50 mM |
| KOAc | 100 mM |
| dATP<br>dCTP<br>dGTP | 300 µM each |
| dUTP | 550 µM |
| ST280ATBUA1 (mock amplification primer) SEQ ID NO: 39 | 0.4 µM (40 pmol per reaction) |
| ST778AATBA1 (mock amplification primer) SEQ ID NO: 40 | 0.4 µM (40 pmol per reaction) |
| AG0203A Genotyping Probe SEQ ID NO: 8 | 0.125 µM |
| UNG nuclease | 10 U/reaction |
| ZO5 polymerase | 40 U/reaction |
| EDTA | 5 mM |
| Mn(OAc)$_2$ | 3 mM |
| Methylene Blue | 10-25 µg/mL |
| Synthetic HCV Target | 0.15 µM |

| Amplification primer | Sequence | SEQ ID NO |
|---|---|---|
| ST280ATBUA1 | GCAGAAAGCGTCTAGCCATGGCGTTB | 39 |
| ST778AATBA1 | GCAAGCACCCTATCAGGCAGTACCACAB | 40 |

B = N6-t-butylbenzyl-dA

Although this reaction mix was used only in the melting analysis, it also contained additional components to simulate an RT-PCR HCV typing analysis. For example, the free nucleotides, the amplification primers, the uracil N-glycosylase (UNG) nuclease, the ZO5 polymerase and the EDTA were not required for the melting analysis, but would otherwise be present in an RT-PCR reaction.

For the melting analysis, the various hybridization mixtures were heated to 95° C. for 2 min, followed by cooling to 20° C. to allow annealing and the formation of hybridization complexes. The reaction containing the hybridization complexes is then heated in approximately 76 cycles where each cycle increases the temperature 1° C. for 30 seconds. Fluorescence was measured for 50 milliseconds at the end of each 30 second cycle. The melting reactions were run in 96 well microtiter plates, and fluorescence was monitored using an ABI PRISM® RTM 7700 Sequence Detection System (Applied Biosystems, Foster City, Calif.). Fluorescence was measured in this experiment (and all experiments that used FAM-labelled probes) using an excitation filter at 485 nm with a 20 nm bandwidth, and an emission filter at 520 nm with a 10 nm bandwidth.

The formation/dissociation of hybridization complexes in the mix was monitored by the use of a FRET system. The FAM label covalently attached to the probe provided a suitable donor emission. The quenching action was provided by the soluble FRET acceptor new methylene blue (see, FIG. 8). New methylene blue is a member of a family of soluble quenchers based on thiazine dyes structures. The new methylene blue quencher has a binding affinity for double-stranded DNA, and thereby results in a quenching effect due to its close proximity to the fluorescent label on the probe when the probe is in a duplex structure with the target. However, the soluble quencher has reduced affinity for single-stranded DNA. Thus, when the solution containing the hybridization complex comprising the probe is heated and eventually dissociates, the affinity of the quencher for the nucleic acid is reduced, resulting in an increase in fluorescence. The new methylene blue soluble quencher was used at various concentrations generally ranging from 10-25 µg/mL. The optimal concentration of soluble quencher was determined empirically. Significantly, it was observed that the resolution of $T_m$ values (i.e., greater separation between $T_m$ values between the various HCV types) can be improved with some HCV typing probes by varying the soluble quencher concentration.

The fluorescence data can be shown graphically by plotting a fluorescence value as a function of temperature (which is a function of thermal cycle number). In this case in FIG. 9, the fluorescence value is a percent fluorescence, where the percent fluorescence is determined by comparing the experimentally measured fluorescence to a fluorescence value in a control tube containing only the single-stranded AG0203A probe in the absence of any HCV target sequences and in the absence of any soluble quencher, and where the control tube is at the same temperature as the experimental tube.

Figure 9:
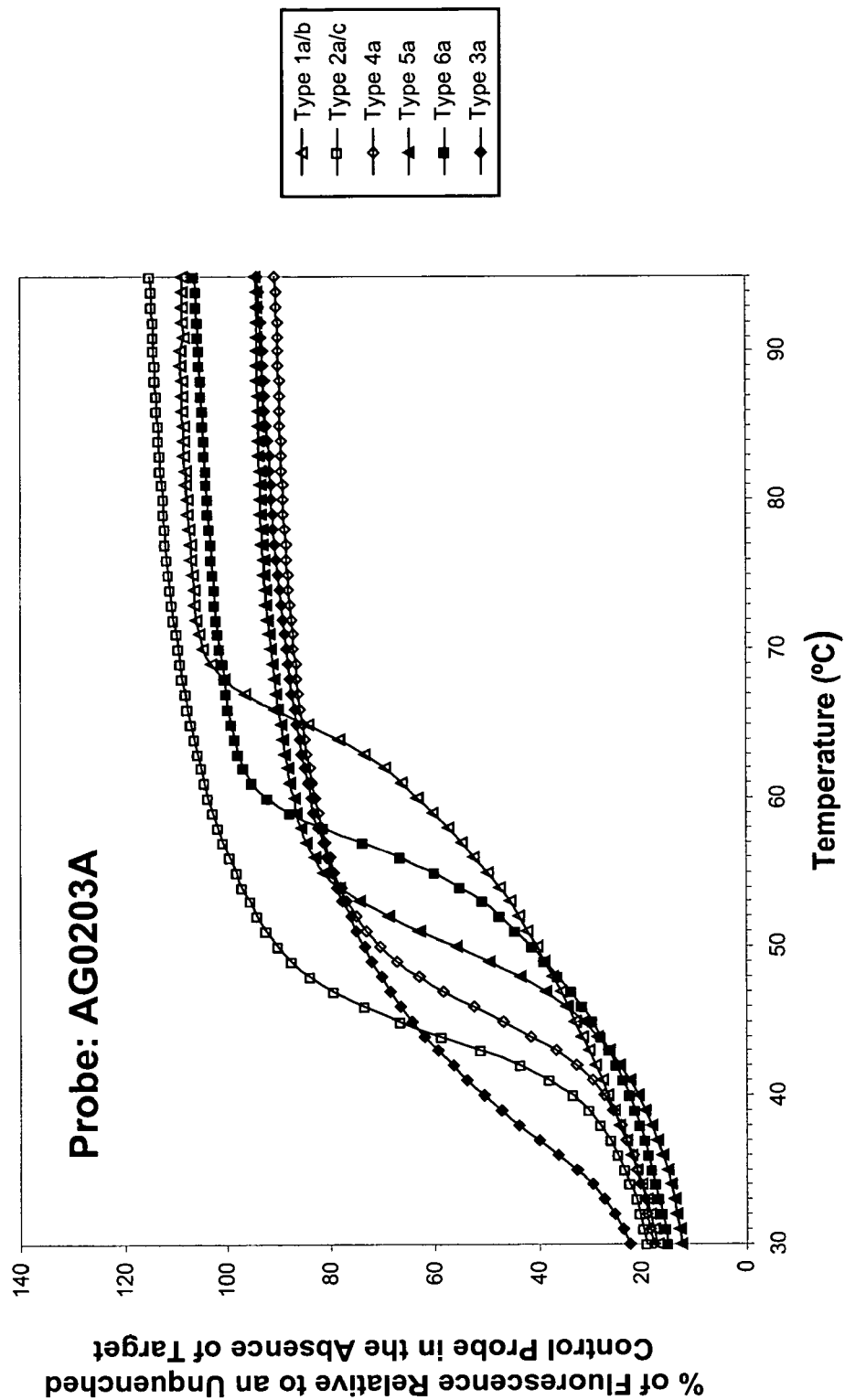
FIG. 9 provides a graph with the results of a melting curve analysis showing percent fluorescence plotted as a function of temperature. The percent fluorescence refers to the percentage of the fluorescence observed compared to the fluorescence of an unquenched probe in the absence of any template and at the same temperature. The experiments used the FAM-labelled AG0203A HCV typing probe and synthetic templates corresponding in base sequence to HCV types as indicated. Fluorescence was measured in this experiment (and all experiments that used FAM-labelled probes) using an excitation filter at 485 nm with a 20 nm bandwidth, and an emission filter at 520 nm with a 10 nm bandwidth. The results of the six separate experiments are overlaid on the same graph. A representative set of data is shown.

The results of six separate experiments (one for each melting analysis using the AG0203A probe and each HCV synthetic template) were overlaid on the same plot, and are shown in FIG. 9. As can be seen, each probe/template complex gave a distinct dissociation profile upon heating.

Figure 10:
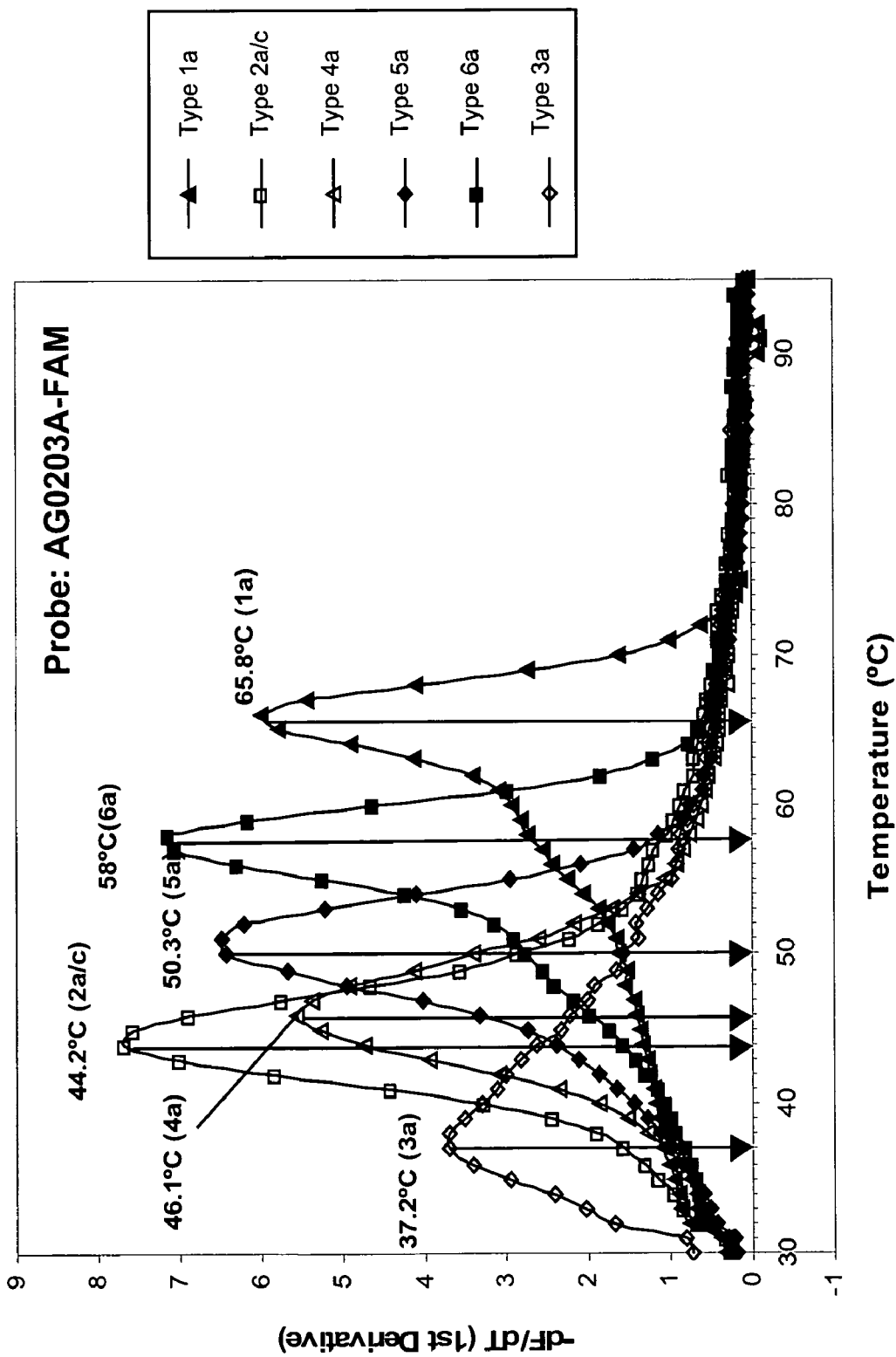
FIG. 10 provides a graph depicting the same melting curve experimental data as FIG. 9, except displaying the data as a first derivative plot (as a function of temperature).

The data in FIG. 9 can be more readily interpreted (and quantitated) by using a first derivative plot of the same data. FIG. 10 shows the data in FIG. 9 as a first derivative plot. The peak of each curve represents the $T_m$ of the hybridization complex at those particular hybridization conditions. As can be seen, the $T_m$ for each HCV genotype can be easily distinguished on the graph.

This analysis was repeated using the same probe and HCV synthetic templates, except the synthetic templates were synthesized using dU in place of dT. This is a potentially useful experimental application, as it allows the elimination of carry-over contamination between experiments by using the UNG nuclease system. The results from that experiment showed equally successful discrimination between the six HCV genotype synthetic templates tested (1a, 2a/c, 3a, 4a, 5a and 6a; data not shown).

In addition to the AG0203A probe that successfully distinguished the six genotypes, as described above, a total of 39 other probes hybridizing to the same 5'-UTR region were also designed and tested. Of those 39 probes, 20 were able to experimentally distinguish six different HCV genotypes (1a, 2a/c, 3a, 4a, 5a and 6a) based on $T_m$ differentiation (and are termed "functional probes" in FIG. 6). Eighteen of the 39 probes were unable to distinguish between all six HCV genotypes in experiments employing either synthetic templates or RT-PCR-generated amplicons, despite the in silico prediction that they would be able to distinguish the six genotypes. Some examples of these unsuccessful probe sequences (termed non-functional probes) are also provided in FIG. 6. Comparisons of predicted and experimentally observed $T_m$ values for some of the probes in FIG. 6 is shown in FIG. 7. The experimentally observed $T_m$ values were obtained in melting analysis experiments using RT-PCR amplicons generated from RNA template from in vitro transcribed HCV genomic material.

Comparison of the successful probe sequences provided in FIG. 6 indicates that relative melting behavior (and as a result the $T_m$) can be modulated by changing sequence length or adding modified bases (e.g., 5-propynyl-dU and 5-Me-dC). For example, HCV typing probes AG0307D and AG0307N both contain 5-propynyl-dU and 5-Me-dC, and both probes effectively resolve at least five HCV genotypes and at least six HCV subtypes.

Example 2

HCV Probe Melting Curves (HCV Typing) Using RT-PCR HCV Amplicons with Post-PCR Addition of Typing Reagents This example describes a melting curve HCV typing analysis using HCV amplicons produced by RT-PCR, followed by the addition of the HCV typing melting curve reagents. This system is considered an "open-tube" system, as the experiment requires access to the RT-PCR reaction products to add the typing reagents (including the typing probe). The AG0203A-FAM probe that was successfully used in EXAMPLE 1 is used in this EXAMPLE. The effectiveness of this probe to differentiate at least five HCV genotypes or at least six different HCV subtypes was assessed using test material generated by amplification of an RT-PCR product.

Template RNA for generating HCV amplicons by RT-PCR was derived by in vitro transcription from plasmids carrying HCV genomic material inserts corresponding to types 1a, 2a, 3a, 4a, 5a and 6a. The sequences of these inserts correspond to the consensus sequences of each of the respective types as described in FIG. 5, except for type 2a. The HCV type 2a cloned insert is a type 2a quasispecies variant having a one nucleotide variation in the 5'-UTR domain targeted by the AG0203A-FAM probe. The relevant portion of the 5'-UTR sequence of this type 2a variant is provided in FIG. 5 and SEQ ID NO: 42. The material used to isolate and subclone the HCV genomic sequences was patient samples. Following the in vitro transcription, the RNA was purified by oligo-dT-sepharose chromatography. The genotype/subtype of each plasmid insert was previously confirmed using other assays, including sequencing.

RT-PCR conditions used were as follows:

| Component | Concentration |
| --- | --- |
| poly rA carrier | 9 µg/mL |
| Glycerol | 6.2% |
| DMSO | 7.5% |
| Tricine, pH 8.3 | 50 mM |
| KOAc | 100 mM |
| dATP | 300 µM each |
| dCTP | |
| dGTP | |
| dUTP | 550 µM |
| ST280ATBUA1 | 0.1 µM |

-continued

| Component | Concentration |
| --- | --- |
| amplification primer SEQ ID NO: 39 | (10 pmol/rx) |
| ST778AATBA1 amplification primer SEQ ID NO: 40 | 0.5 µM (50 pmol/rx) |
| ZO5 polymerase | 40 U/reaction |
| Mn(OAc)$_2$ | 3 mM |
| HCV RNA TARGET | 1,000,000 (10$^6$)copies |

| Amplification primer | Sequence | SEQ ID NO |
| --- | --- | --- |
| ST280ATBUA1 | GCAGAAAGCGTCTAGCCATGGCGTTB | 39 |
| ST778AATBA1 | GCAAGCACCCTATCAGGCAGTACCACAB | 40 |

B = N6-t-butylbenzyl-dA

Figure 18:
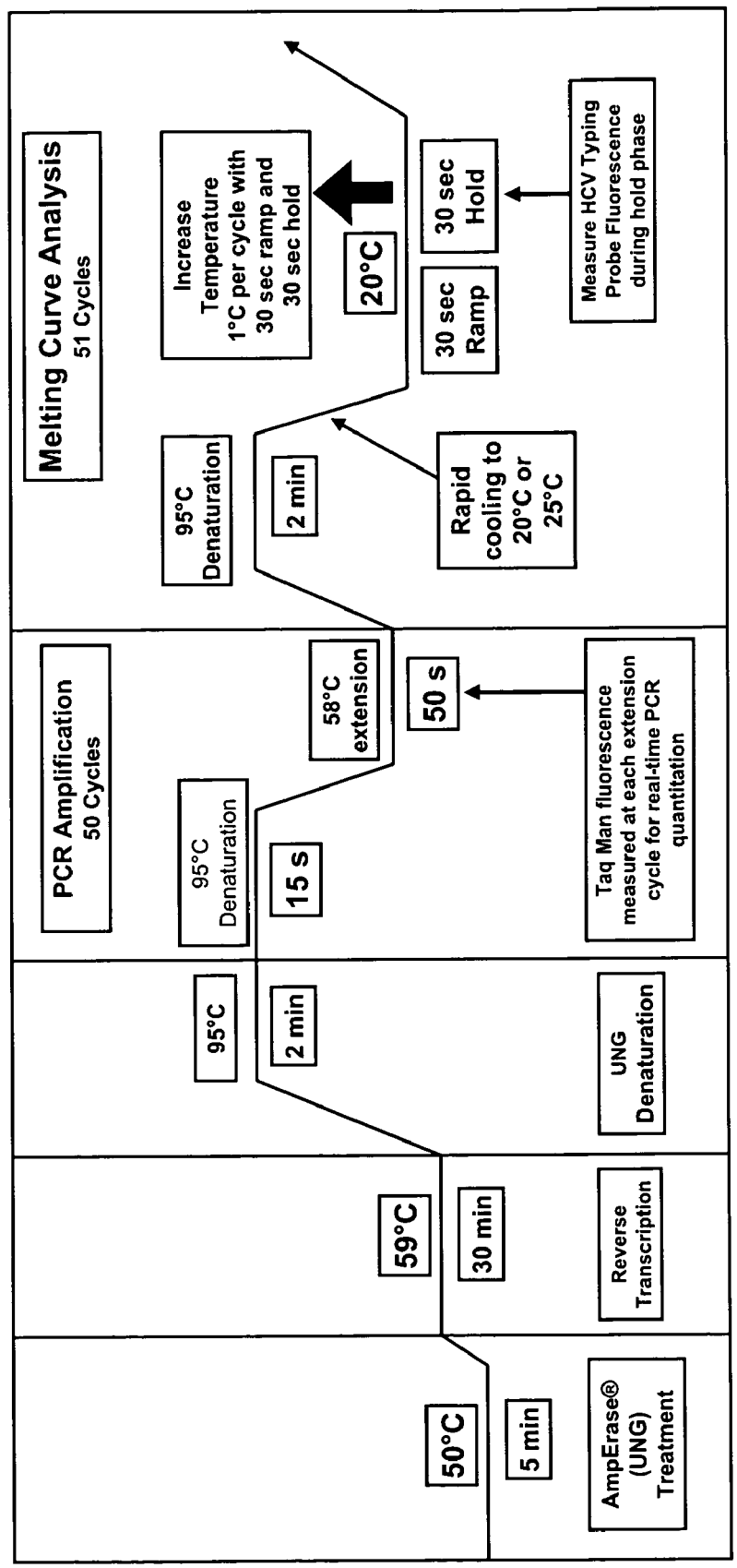
FIG. 18 provides a diagram detailing the thermocycling conditions used in the "closed-tube" RT-PCR, HCV quantitation and HCV genotyping (melting curve) combined experimental reactions, as used in FIGS. 19-24. Other closed-tube experiments described herein (e.g., FIGS. 13-17) used these same thermocycling conditions, except without the TaqMan real-time PCR quantitation.

The RT-PCR thermal cycling conditions are shown in FIG. 18. The reaction is initiated with an UNG decontamination step at 50° C. to eliminate any carry-over contamination by dU-containing polynucleotides. The reverse transcriptase reaction is then carried out at 59° C., where one of the PCR amplification primers also primes the reverse transcription. The RT-PCR reaction used RNA transcripts derived from in vitro transcription of plasmids carrying subcloned HCV genomic material corresponding to each of the HCV types as indicated. The amplification primers used in the RT-PCR reaction are indicated.

The RT-PCR reaction was an asymmetric reaction where one of the amplification primers was in 5-fold excess over the opposite primer, resulting in an overabundance of amplification of the HCV genomic strand that will hybridize to the HCV typing probe. The amplification with the indicated primers produced an approximately 200 base amplicon.

Following the RT-PCR thermal cycling program, the following reagents were added to the reaction before the start of the melting analysis. The EDTA was added to the reaction to sequester Mg and thereby inactivate the ZO5 polymerase.

| Component | Concentration |
| --- | --- |
| RT-PCR reaction product starting volume | 90 µL |
| EDTA | 5 mM final conc. |
| AG0203A-FAM HCV Typing Probe SEQ ID NO: 8 | 3 µM (15 pmol) final conc. |
| New Methylene Blue | 25 µg/mL final conc. |
| Total reaction volume | 100 µL |

The AG0203A-FAM probe was used in the melting curve analysis with each of six different HCV amplicons corresponding to the various HCV types. The melting analysis used the same thermal cycling and fluorescence measuring conditions as described in EXAMPLE 1.

Figure 11:
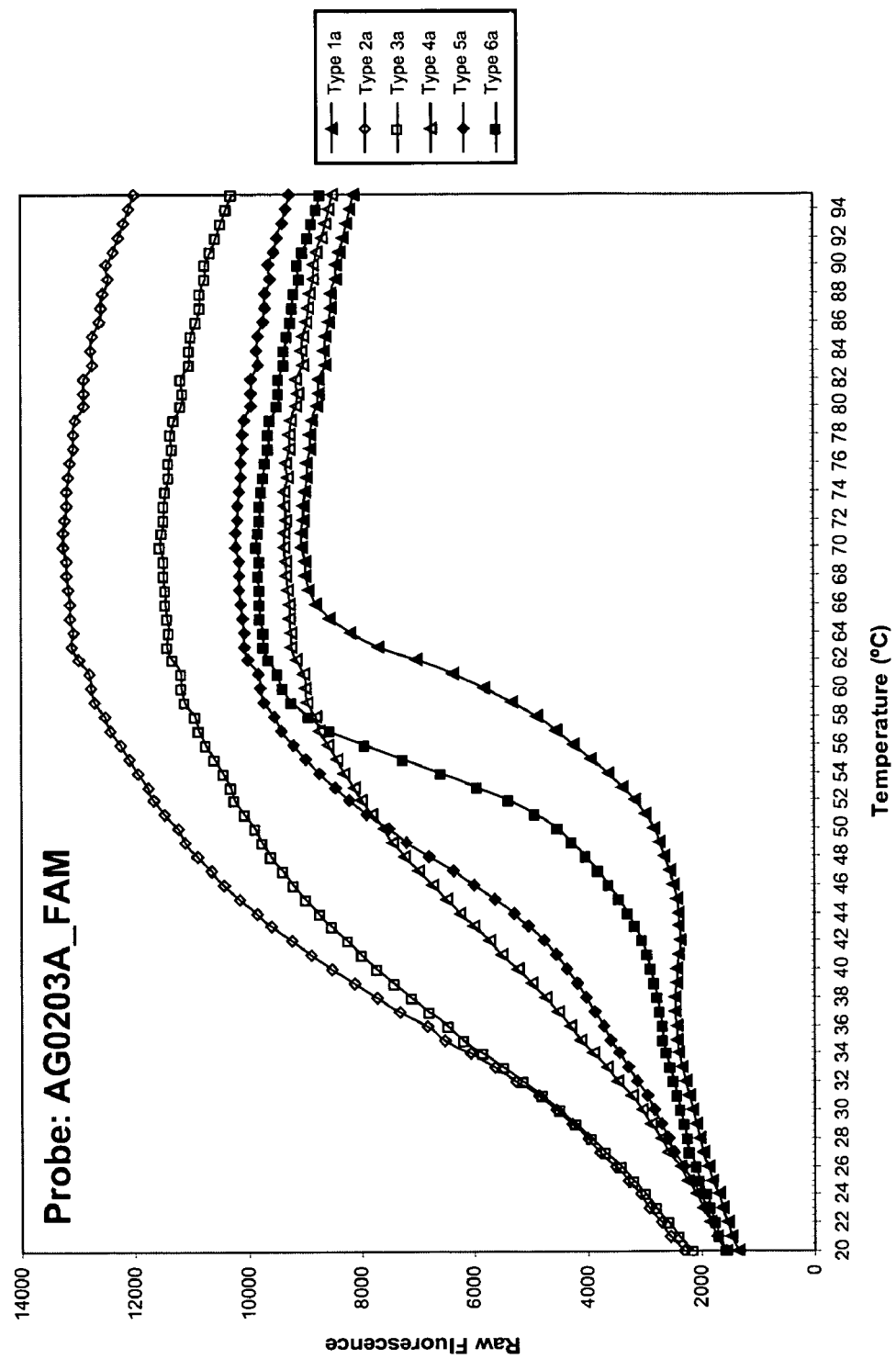
FIG. 11 provides a graph with the results of an "open-tube" combined RT-PCR followed by a melting curve analysis. The graph shows the melting curve raw fluorescence data plotted as a function of temperature. The melting curve analysis used the type-specific amplicons generated in the RT-PCR and the AG0203A-FAM typing probe. The results of six separate experiments are overlaid on the same graph. A representative set of data is shown.

The collected fluorescence data of the melting analysis is shown graphically in a plot of raw fluorescence as a function of temperature, as shown in FIG. 11. The results of six separate experiments (one for each melting analysis using the AG0203A probe and each HCV amplicon) were overlaid on the same plot. As can be seen, each probe/template gave a distinct dissociation profile upon heating.

Figure 12:
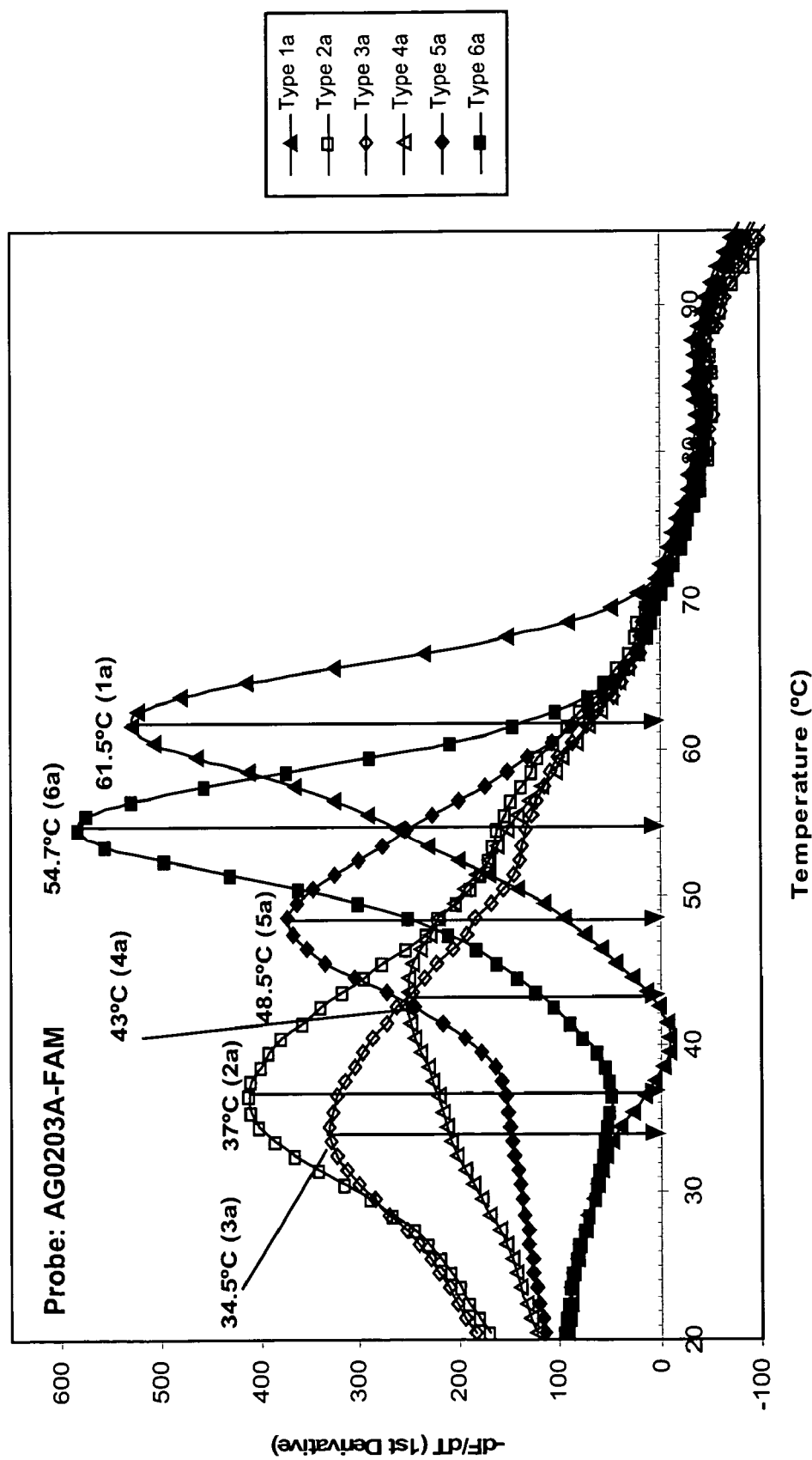
FIG. 12 provides a graph depicting the same melting curve experimental data as FIG. 11, except displaying the data as a first derivative plot (as a function of temperature).

FIG. 12 shows the data in FIG. 11 displayed using a first derivative plot as a function of temperature. The peak of each curve in FIG. 12 represents the $T_m$ of the hybridization complex at those particular hybridization conditions. As can be seen, the $T_m$ for each HCV genotype can be differentiated and distinguished from the other peaks (the $T_m$ values) on the graph.

This analysis was repeated using the same HCV RT-PCT amplicons and probes AG0503A, AG0305B, AG0503D, AG0503E, AG0503F, AG0503G, and AG0503H, all using the same RT-PCR conditions and melting curve analysis. The results from this analysis showed successful discrimination between the six HCV genotypes (1, 2, 3, 4, 5 and 6) and subtypes (1a/b, 2a/c, 3a, 4a, 5a and 6a) using probes AG0503D, AG0503E and AG0503F. Probes AG0503A, AG0305B, AG0503G and AG0503H were unable to distinguish between HCV types 2a and 3a.

Example 3

HCV Probe Melting Curves (HCV Typing) Using RT-PCR HCV Amplicons in a Closed-Tube System This example describes a melting curve HCV typing analysis, where the HCV target material is an amplicon generated by an RT-PCR amplification reaction, and furthermore, where the RT-PCR and the melting curve analysis are conducted in a single reaction mix without the need for any additional manipulation of reagents, e.g., addition of the HCV typing probe. This system is considered a "closed-tube" system, as the reaction mixture does not require any further manipulation other than the external thermocycling conditions and fluorescence measurements. A number of probes were used in this analysis. The effectiveness of the various probes to differentiate various HCV amplicons generated by RT-PCR was assessed.

Template RNA for generating HCV amplicons by RT-PCR was derived by in vitro transcription from plasmids carrying HCV genomic material inserts corresponding to genotypes 1a, 2a, 3a, 4a, 5a and 6a. Following the in vitro transcription, the RNA was purified by oligo-dT-sepharose chromatography.

A single genotyping/melting analysis reaction was established as follows:

| Component | Concentration |
|---|---|
| poly rA carrier | 9 µg/mL |
| Glycerol | 6.2% |
| DMSO | 7.5% |
| Tricine, pH 8.3 | 50 mM |
| KOAc | 100 mM |
| dATP<br>dCTP<br>dGTP | 300 µM each |
| dUTP | 550 µM |
| ST280ATBUA1 amplification primer SEQ ID NO: 39 | 0.1 µM (10 pmol/rx) |
| ST778AATBA1 amplification primer SEQ ID NO: 40 | 0.5 µM (50 pmol/rx) |
| AG0203A-FAM HCV Typing Probe SEQ ID NO: 8 | 20 pmol |
| UNG nuclease | 10 U/reaction |
| ZO5 polymerase | 40 U/reaction |

-continued

| Component | Concentration |
|---|---|
| Mn(OAc)$_2$ | 3 mM |
| Methylene Blue | 10-25 µg/mL |
| HCV TARGET RNA | $10^3$-$10^6$ copies per reaction |

An asymmetric RT-PCR reaction was run using the above reaction mix and with the thermal cycling conditions shown in FIG. 18. These thermal cycling conditions resulted in the RT-PCR amplification of the HCV amplicon, but also proceeded directly to a melting curve analysis. In the experiment described in FIG. 13, the AG0203A-FAM probe was used in the melting curve analysis alternatively with each of six different HCV amplicons corresponding to the various HCV types. The melting analysis used the same thermal cycling and fluorescence measuring conditions as described in EXAMPLE 1.

Figure 13:
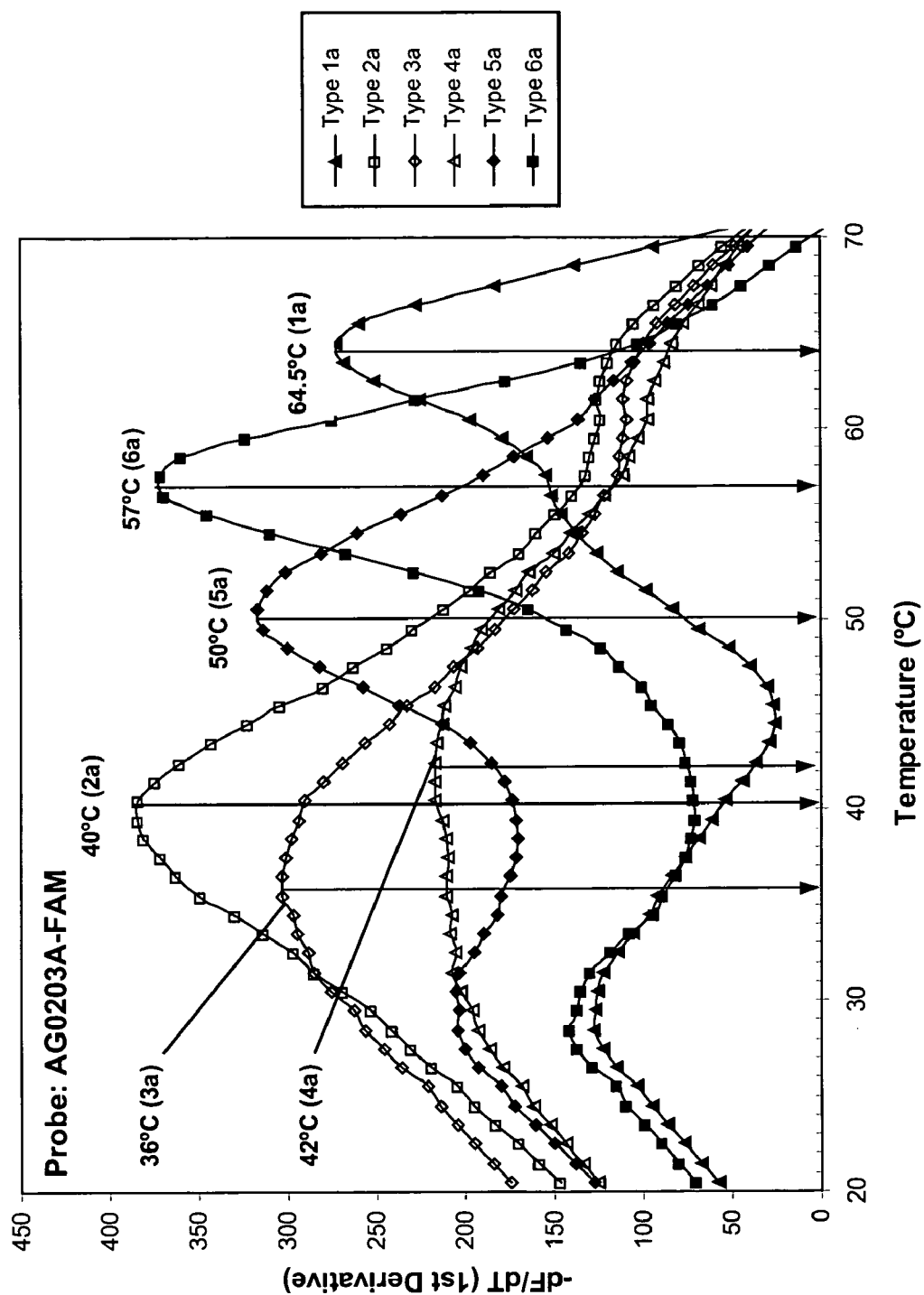
FIG. 13 provides a graph with the results of a "closed-tube" combined RT-PCR and melting curve analysis experiment, where the graph plots the first derivative of melting curve fluorescence data as a function of temperature. The RT-PCR reaction used amplification primers that amplified a region within the 5'-UTR. The melting curve analysis used amplicons generated in RT-PCR reactions and used the AG0203A-FAM typing probe. The results of the six separate experiments are overlaid on the same graph. A representative set of data is shown.

The collected fluorescence data of the melting analysis is shown graphically in FIG. 13 in a first derivative plot of fluorescence as a function of temperature. The results of six separate RT-PCR and melting analyses (one for each genomic amplicon, all using the AG0203A-FAM probe) were overlaid on the same plot. As can be seen, each probe/amplicon gave a distinct $T_m$.

Figure 14:
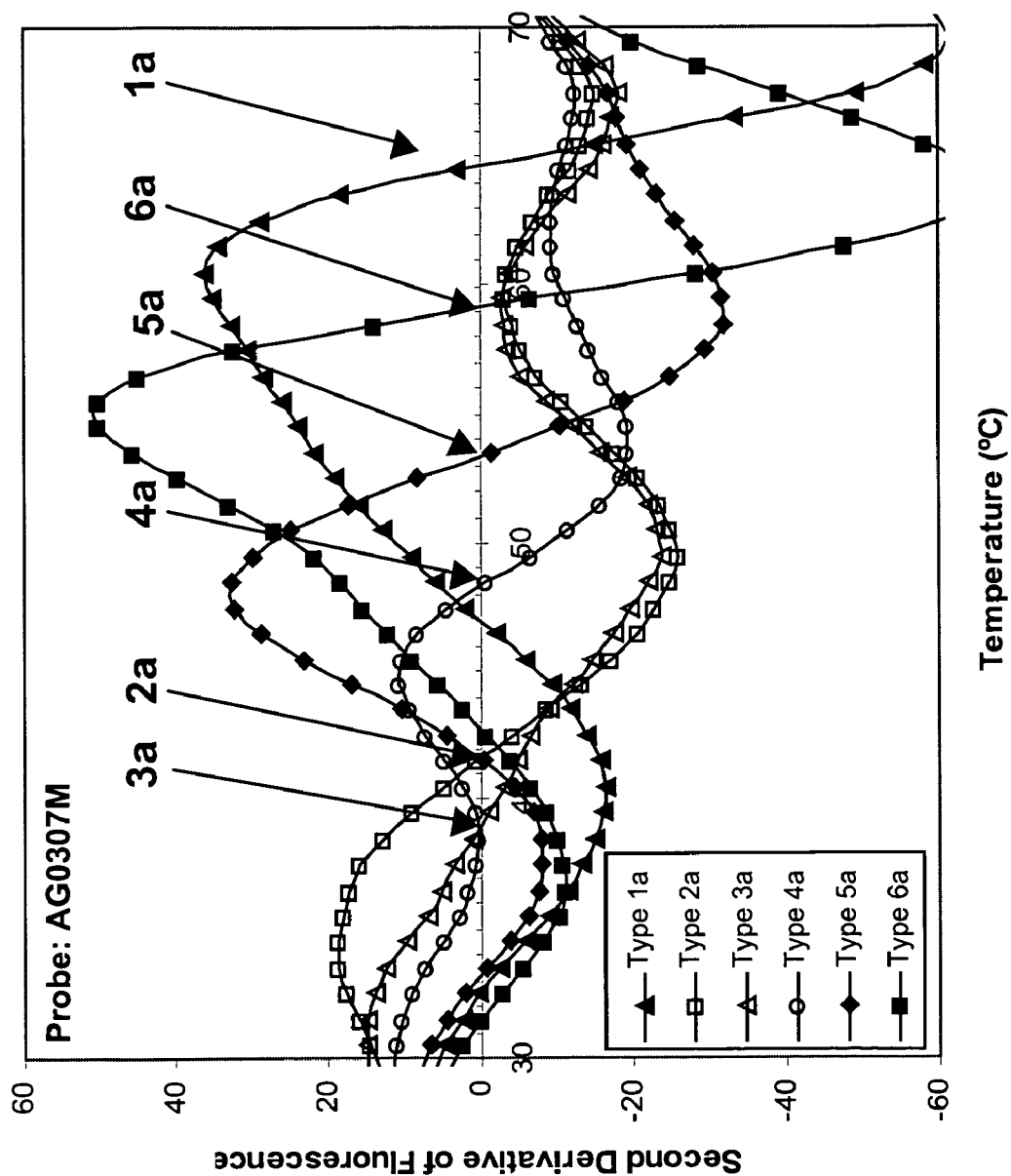
FIG. 14 provides a graph with the results of a "closed-tube" combined RT-PCR and melting curve analysis experiment, where the graph plots the second derivative of the melting curve fluorescence data as a function of temperature. The RT-PCR reaction used RNA transcripts derived from in vitro transcription of plasmids carrying subcloned HCV genomic material corresponding to each of the HCV types as indicated. The RT-PCR reaction used amplification primers that amplified a region within the 5'-UTR. The melting curve analysis used the type-specific amplicons generated in the RT-PCR and the AG0307M typing probe. The results of the six separate experiments are overlaid on the same graph. A representative set of data is shown.
Figure 15:
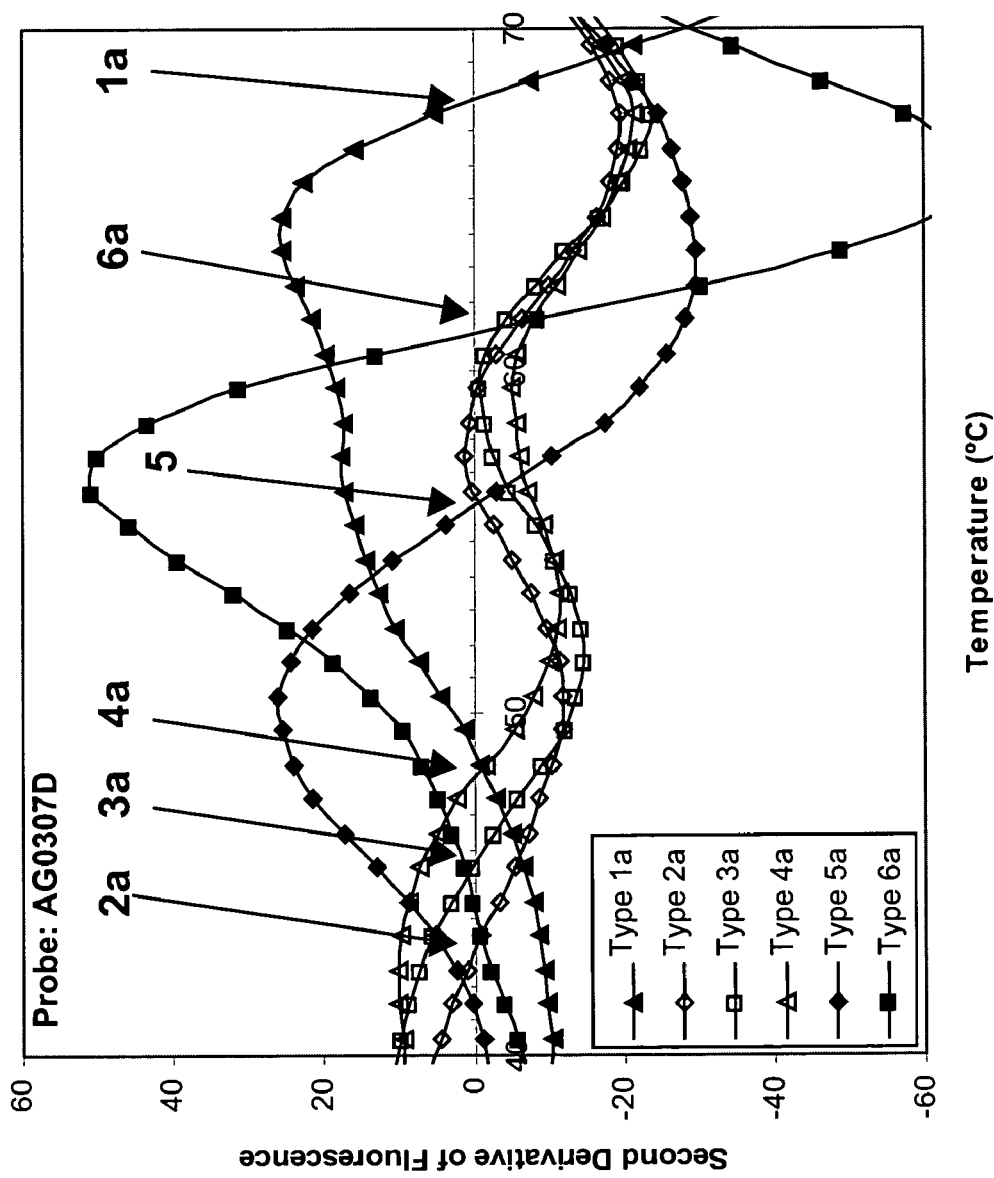
FIG. 15 provides a graph with the results of a "closed-tube" combined RT-PCR and melting curve analysis experiment, where the graph plots the second derivative of the melting curve fluorescence data as a function of temperature. The RT-PCR reaction used RNA transcripts derived from in vitro transcription of plasmids carrying subcloned HCV genomic material corresponding to each of the HCV types as indicated. The RT-PCR reaction used amplification primers that amplified a region within the 5'-UTR. The melting curve analysis used the subtype-specific amplicons generated in the RT-PCR and the AG0307D genotyping probe. The results of six separate experiments are overlaid on the same graph.

Other probes were also used in this closed tube HCV genotyping system using the same RT-PCR conditions and melting curve analysis parameters. Results for additional probes are shown in FIG. 14 (probe AG0307M; SEQ ID NO: 14) and FIG. 15 (probe AG0307D; SEQ ID NO: 13) using second derivative plots. These two probe sequences are also provided in FIG. 6. As can be seen in these figures, these two probes also yield $T_m$ values with each of the HCV types that can be differentiated within the accuracy of the thermal cycling and fluorescence measurement instrumentation.

Example 4

Effect of Target Copy Number (Viral Load) on HCV Typing Probe Melting Curves

This example was designed to confirm the accuracy of the HCV typing assay over a broad range of virus target template concentrations. The effects of varying the HCV template concentration (copy number) on the HCV hybridization complex (comprising a viral template and an HCV typing probe) melting temperature ($T_m$ values) were analyzed.

In one experiment, probe AG0203A-FAM was used in a melting analysis with an HCV subtype 1a RT-PCR amplicon target. The copy number of the target was varied between 1,000 copies per reaction to 1,000,000 copies per reaction while the concentration of the genotyping probe remained constant. The assay used the methylene blue soluble quencher at a concentration of 25 µg/mL. RT-PCR and melting curve analyses were done in a combined, closed-tube system using the same protocol described in EXAMPLE 3.

Figure 16:
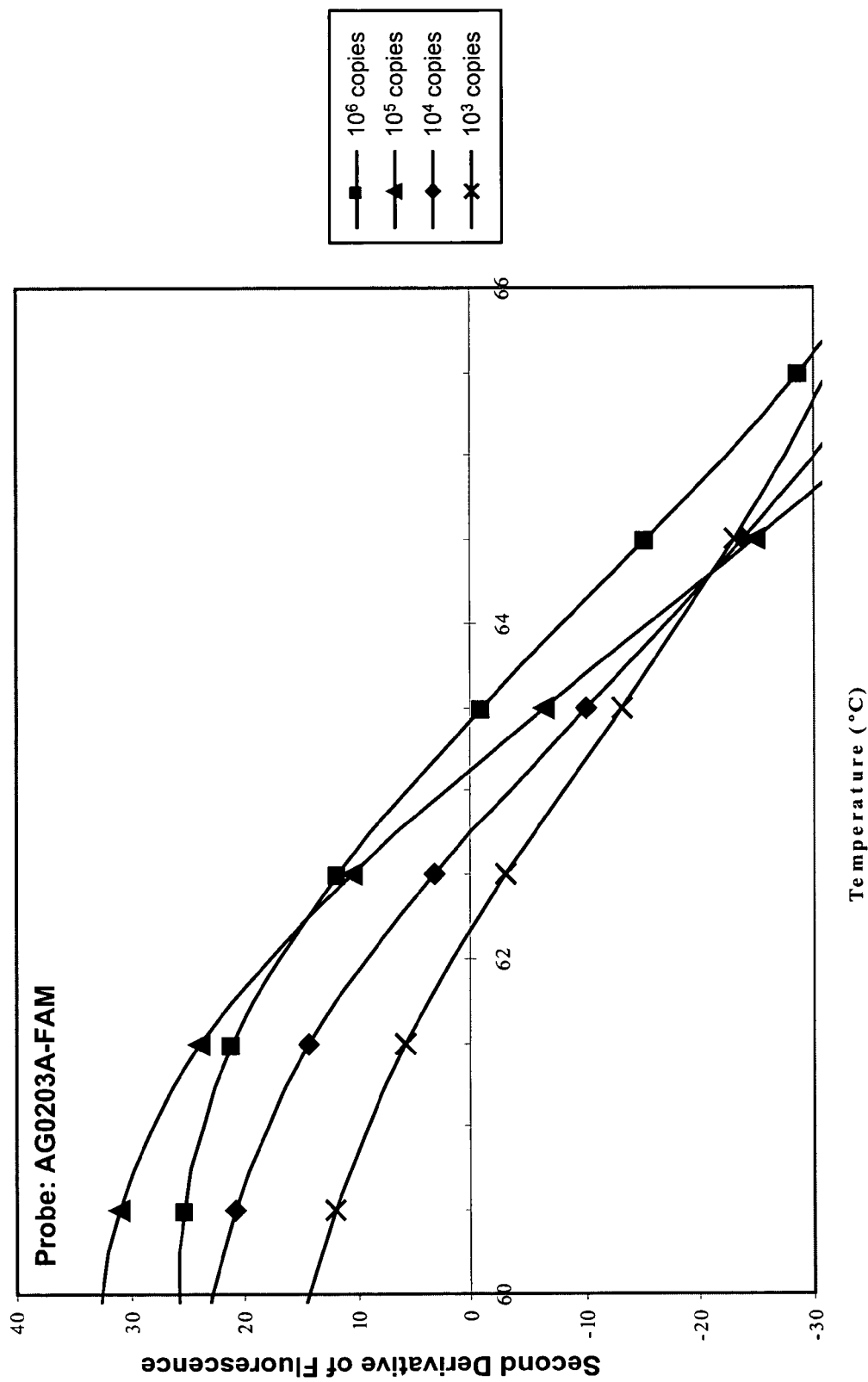
FIG. 16 provides a graph with the results of a melting curve analysis experiment designed to test the effect of input target RNA copy number on $T_m$ differentiation. The experiment used the AG0203A-FAM typing probe, and amplification primers that amplified a region within the 5'-UTR. The template material for the RT-PCR reaction used RNA transcripts derived from in vitro transcription of a plasmid carrying subcloned HCV genomic material corresponding to HCV type 1a. The in vitro transcribed RNA was used at four different concentrations (i.e., copy numbers) ranging from 1,000 copies to 1,000,000 copies per hybridization reaction. Fluorescence data is displayed as a second derivative plot as a function of temperature. A representative set of data is shown.

The results of this analysis are shown in FIG. 16. As can be seen in this figure, the $T_m$ values vary over a relatively small 1.25° C. interval as a function of the 1,000-fold range in template concentration, where there is a small decrease in the $T_m$ at lower target concentrations. This variability was well within a tolerable range, considering the much more sizeable $T_m$ differences between different HCV types previously observed.

Figure 17:
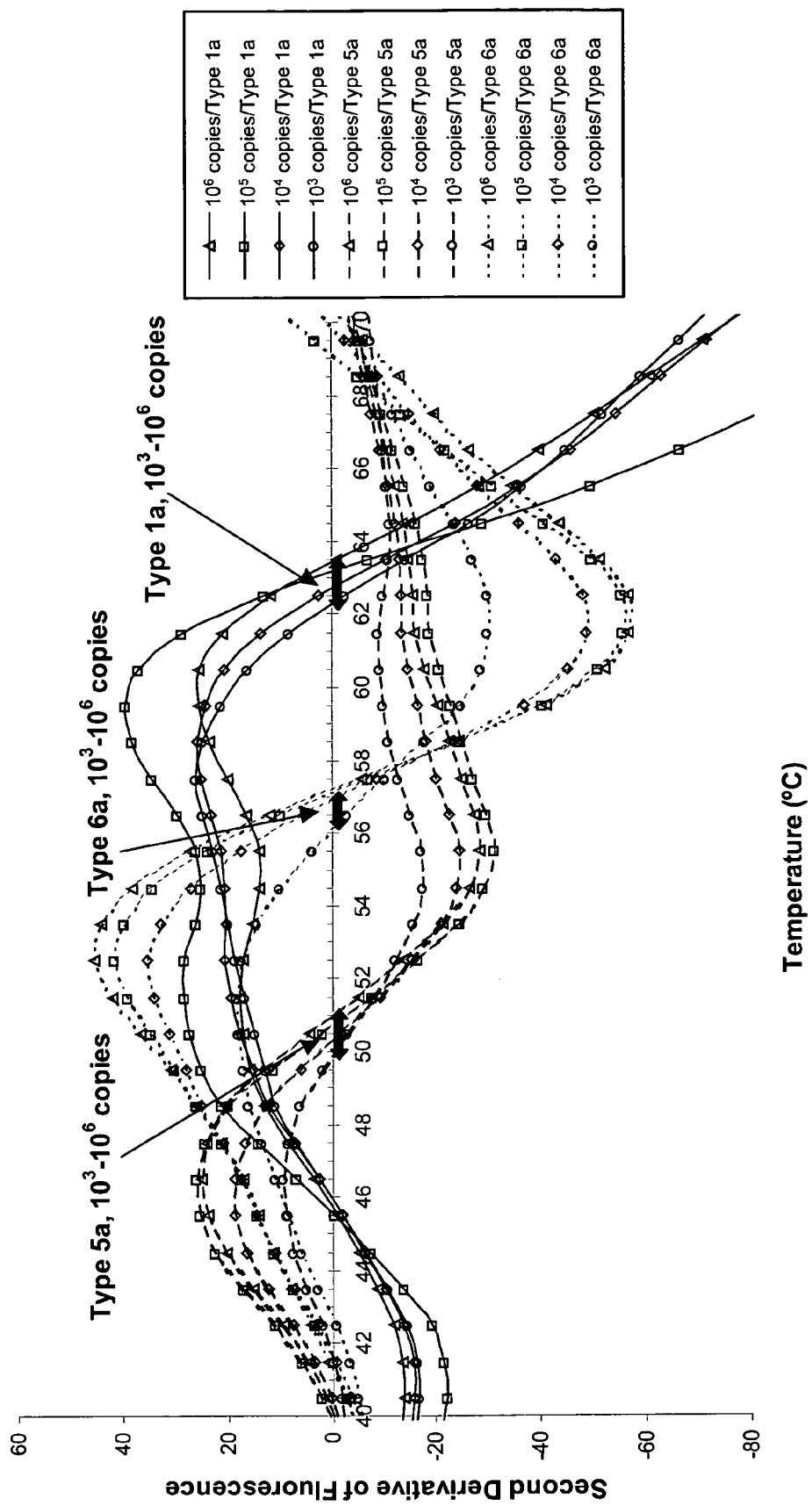
FIG. 17 provides a graph with the results of a melting curve analysis experiment designed to test the effect of input target RNA copy number on $T_m$ differentiation. The experiment used the AG0203A-FAM typing probe, and amplification primers that amplified a region within the 5'-UTR. The template material for the RT-PCR reaction used RNA transcripts derived from in vitro transcription of plasmids carrying subcloned HCV genomic material corresponding to HCV types 1a, 5a and 6a. The in vitro transcribed RNA was used at three different concentrations (i.e., copy numbers) ranging from 1,000 copies to 1,000,000 copies per hybridization reaction. Fluorescence data is displayed as a second derivative plot as a function of temperature. A representative set of data is shown. The data shown

The experiment depicted in FIG. 16 was expanded to included HCV targets corresponding to genotypes 5a and 6a, which was done in order to assess the effects of template concentration (i.e., copy number) on the $T_m$ using multiple HCV types. In this broader experiment, the probe AG0203A-FAM was again used. Each HCV type was tested using four template concentrations, which were $10^3$, $10^4$, $10^5$ and $10^6$ copies per reaction. RT-PCR and melting curve analyses were done in a combined, closed-tube system using the same protocol described in EXAMPLE 3. Methylene Blue soluble quencher was used at 25 μg/mL. Results from this melting analysis are shown in FIG. 17. The graph shown in FIG. 17 is a broader view of the experiment shown in FIG. 16.

As can be seen, although the $T_m$ of each concentration within one HCV type varied slightly, the melting points of the different types were all sufficiently differentiated. Although the $T_m$ is somewhat dependent on the input target RNA copy number, the three genotypes shown are easily distinguished over a four log range of target concentration.

Example 5

Simultaneous HCV Typing and Viral Quantitation in a Single Closed-Tube Assay System This example describes a method for the simultaneous determination of HCV viral load (i.e., HCV quantitation) and HCV type in a single closed-tube reaction.

The HCV typing is accomplished as described in EXAMPLE 3, namely by generating an HCV amplicon in an RT-PCR reaction, followed by a melting curve analysis using a suitable HCV typing probe (as provided in FIG. 6). The HCV quantitation takes place in the same reaction tube by including a probe suitable for use in a 5'-nuclease assay (e.g., a TaqMan probe) which monitors the accumulation of the HCV amplicon generated by RT-PCR from the HCV RNA sample (derived from in vitro transcribed product). This approach can ideally be applied as a "closed-tube" system that does not require any purification steps or addition of supplemental components once the reaction mix is made.

A single closed-tube quantitation/typing/melting analysis reaction was established as follows:

| Component | Concentration |
|---|---|
| poly rA carrier | 9 μg/mL |
| Glycerol | 6.2% |
| DMSO | 7.5% |
| Tricine, pH 8.3 | 50 mM |
| KOAc | 100 mM |
| dATP | 300 μM each |
| dCTP | |
| dGTP | |
| dUTP | 550 μM |
| ST280ATBUA1 amplification primer SEQ ID NO: 39 | 0.1 μM (10 pmol/rx) |
| ST778AATBA1 amplification primer SEQ ID NO: 40 | 0.5 μM (50 pmol/rx) |
| ST650AAFBHQ2 TaqMan Quantitation Probe SEQ ID NO: 41 | 0.1 μM (10 pmol/rx) |
| AG0308F HCV Typing Probe SEQ ID NO: 16 | 0.1 μM (10 pmol/rx) |
| UNG nuclease | 10 U/reaction |
| Z05 polymerase | 40 U/reaction |
| Mn(OAc)$_2$ | 3 mM |
| New Methylene Blue | 25 μg/mL |
| HCV TARGET RNA | $10^3$-$10^6$ copies per reaction |

ST650AAFBHQ2 TaqMan Quantitation Probe
SEQ ID NO:41
FCGGTGTACTCACCGQTTCCGCAGACCACTATGP
F = FAM; Q = BHQ-2; P = Terminal Phosphate In an initial experiment, a "closed-tube" reaction that combined RT-PCR, HCV quantitation and HCV typing (melting curve) analysis was established, as described above. The reaction used a single RT-PCR template corresponding to HCV subtype 1a at four different template concentrations ranging from 1,000 ($10^3$) to 1,000,000 ($10^6$) copies per reaction. The thermal cycling program used for the reaction is provided in FIG. 18.

Figure 19:
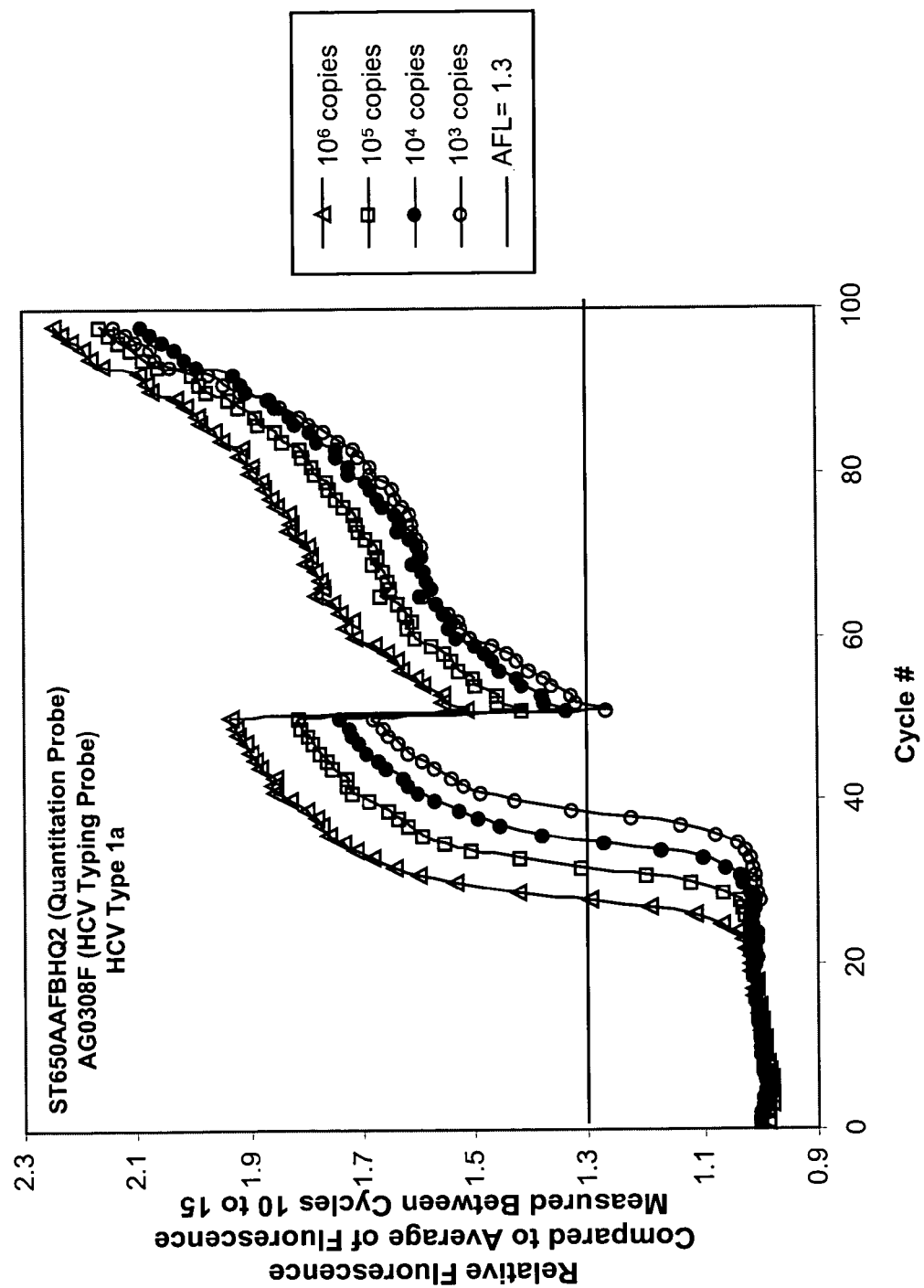
FIG. 19 provides a graph with the results of a "closed-tube" RT-PCR and HCV typing (melting curve) analysis that also incorporates HCV quantitation by use of a TaqMan probe (ST650AAFBHQ2). The experiment used an RT-PCR template corresponding to HCV type 1a at four different template concentrations ranging from 1,000 ($10^3$) to 1,000,000 ($10^6$) copies per reaction (i.e., four different simulated viral copy numbers). The template material for the RT-PCR reaction used RNA transcripts derived from in vitro transcription of a plasmid carrying subcloned HCV genomic material corresponding to HCV type 1a, and the RT-PCR amplification primers amplified a region within the 5'-UTR. The melting analysis used new methylene blue soluble quencher. Data is displayed as relative fluorescence as a function of cycle number. The melting analysis portion of the thermocycling program starts at cycle 50. The results of each copy number analysis are overlaid on the same graph. A representative set of data is shown.

The fluorescence data collected from the experiment is shown in FIG. 19. Fluorescence data is shown as relative fluorescence as a function of cycle number. Relative fluorescence is calculated by dividing the observed fluorescence value at each cycle by a fluorescence value that is obtained by averaging each of the fluorescence values measured between cycles 10-15 (considered basal or background fluorescence). This graph also indicates the arbitrary fluorescence level (AFL). The PCR cycle where the fluorescence signal is above some arbitrary level (the AFL) is the threshold cycle (CT). Input copy number is inversely proportional to the CT.

The RT-PCR used the HCV type 1a RNA template generated by in vitro transcription. The reaction also included amplification primers ST280ATBUA1 (SEQ ID NO: 39) and ST778AATBA1 (SEQ ID NO: 40), and TaqMan probe ST650AAFBHQ2 (SEQ ID NO: 41). An asymmetric RT-PCR reaction was run using the above reaction mix and with the thermal cycling conditions shown in FIG. 18. Inclusion of the TaqMan probe allowed the real-time monitoring of accumulation and quantitation of the HCV amplicon during the RT-PCR. Fluorescence from the TaqMan probe was measured for 50 milliseconds during each PCR amplification cycle for 50 cycles at the 58° C. phase.

Following the generation of the HCV amplicon from the RT-PCR, the thermal cycling proceeded directly to a melting curve analysis. The HCV typing melting curve analysis used the AG0308F HCV typing probe with new methylene blue soluble quencher. The results of each copy number analysis are overlaid on the same graph, for a total of four plots in FIG. 19. As can be seen in the graph, each HCV 1a template concentration gave a distinct CT value.

Figure 20:
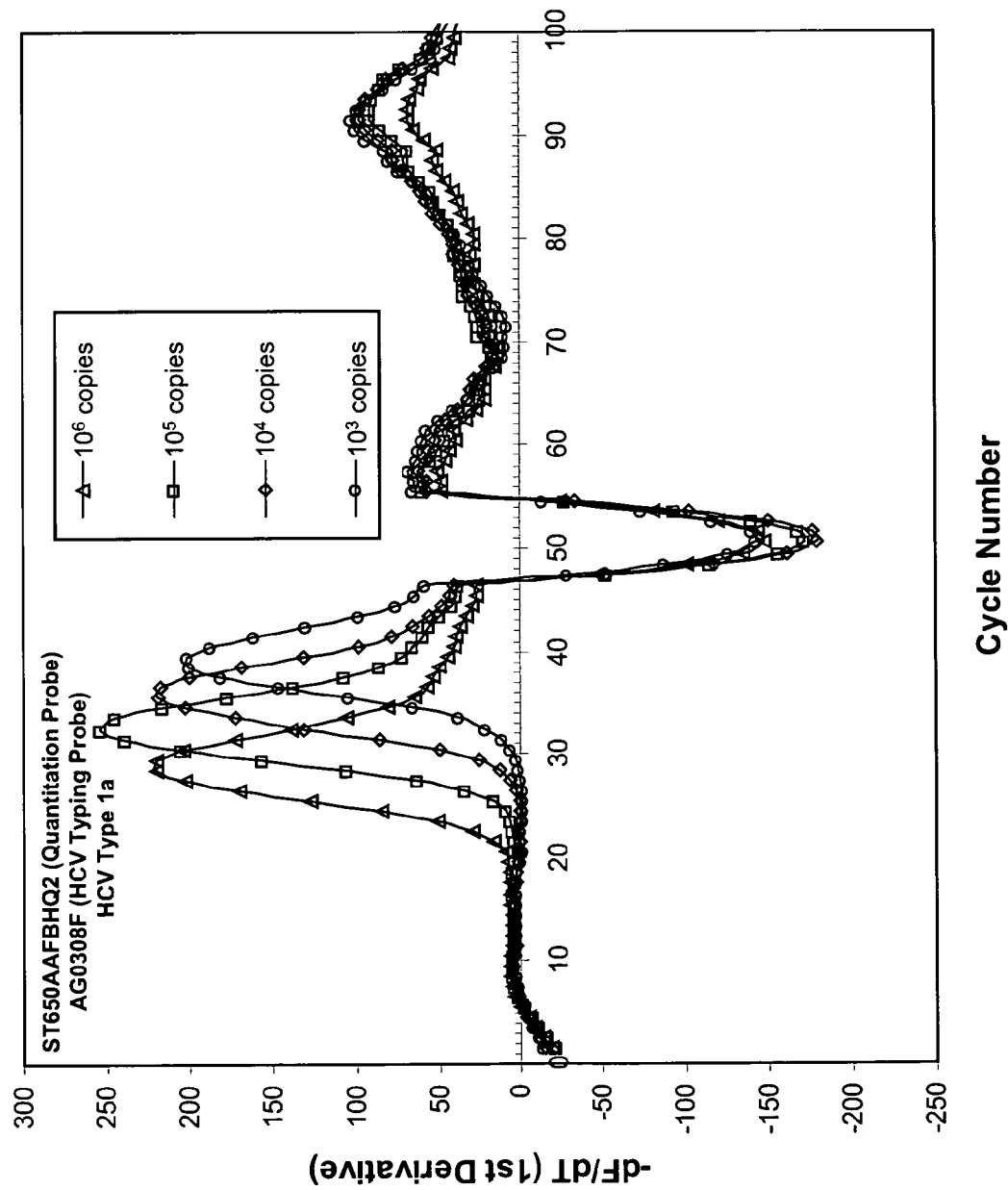
FIG. 20 provides a graph with the results of the closed-tube combined RT-PCR, HCV quantitation and HCV genotyping (melting curve) analysis described in FIG. 19 using a first derivative plot.
Figure 21:
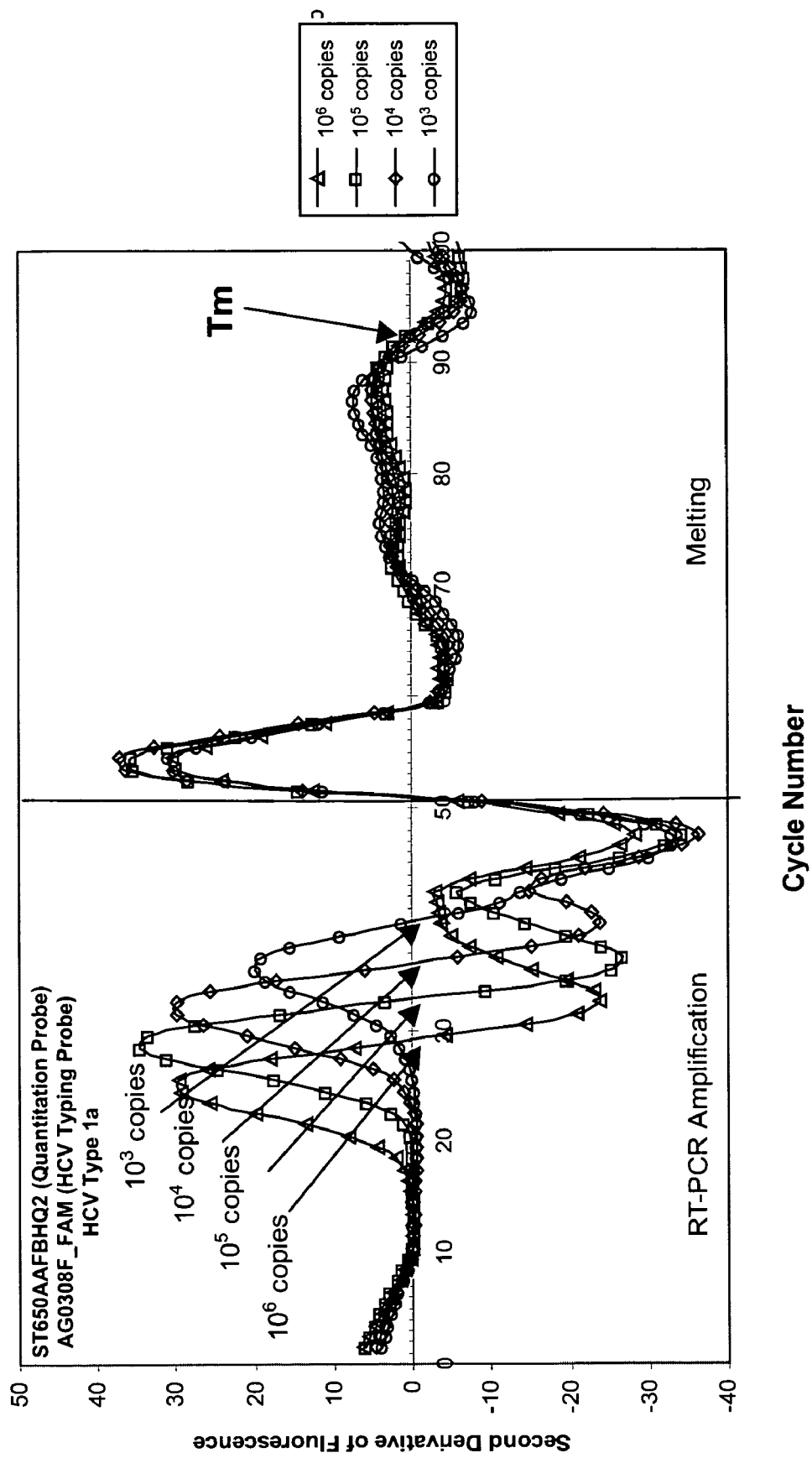
FIG. 21 provides a graph with the results of the closed-tube combined RT-PCR, HCV quantitation and HCV genotyping (melting curve) analysis described in FIG. 19 using a second derivative plot. The $T_m$ of each hybridization complex can be determined by subtracting 26 from the cycle number.

FIG. 20 provides a graph with the results of the same closed-tube combined RT-PCR, HCV quantitation and HCV typing (melting curve) analysis described in FIG. 19 using a first derivative plot. FIG. 21 provides a graph with the results of the same closed-tube combined RT-PCR, HCV quantitation and HCV typing (melting curve) analysis described in FIG. 19 using a second derivative plot. In this second derivative plot, the different CT values for each template concentration can be clearly distinguished. Since HCV subtype 1a was used in each sample, the melting temperature ($T_m$) is identical or nearly identical for each sample. The $T_m$ of each hybridization complex can be determined by subtracting 26 from the cycle number in the melting curve portion of the graph (after cycle number 50) at the point where the graph intersects zero on the y-axis.

Figure 22:
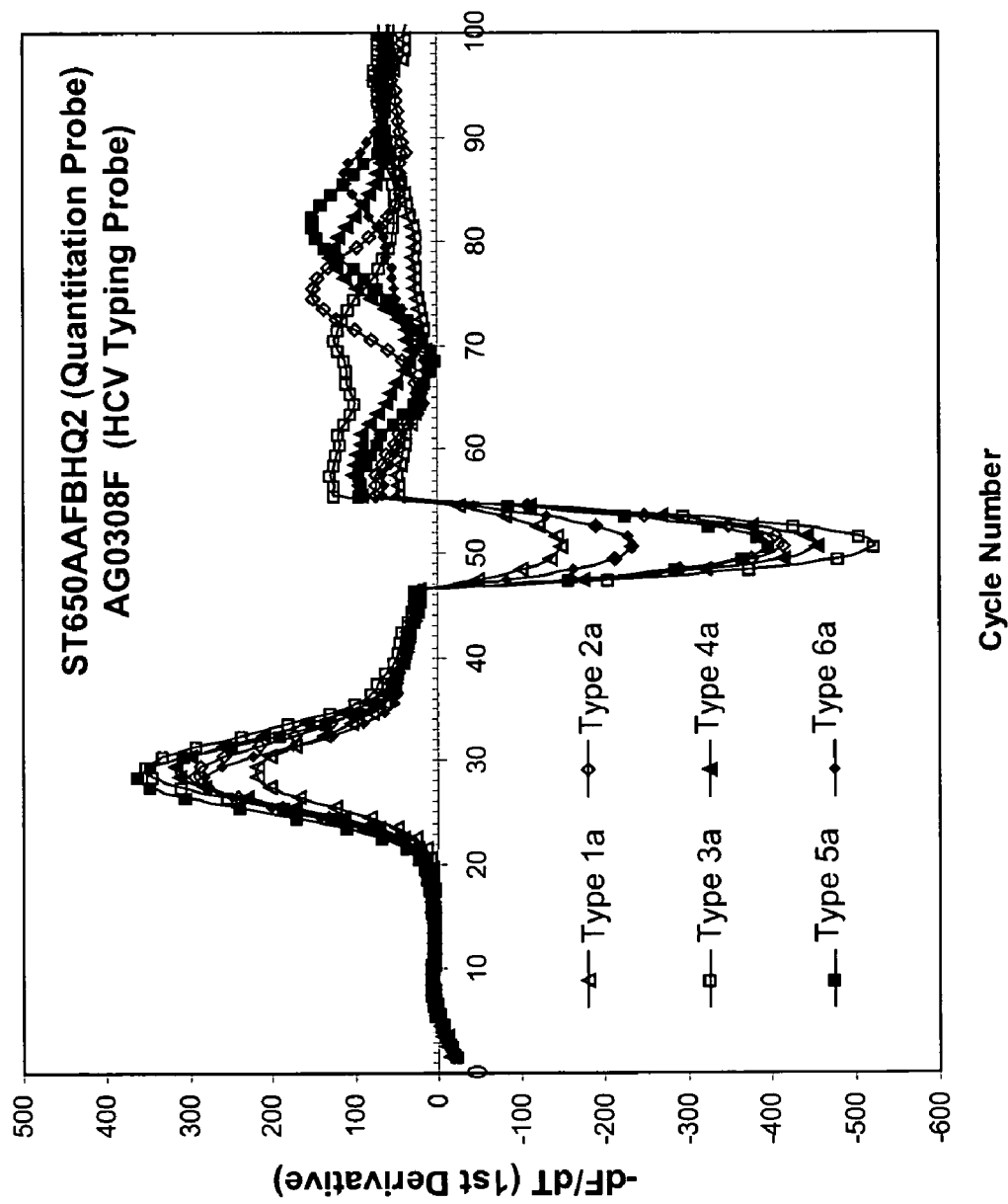
FIG. 22 provides a graph with the results of a "closed-tube" combined RT-PCR, HCV quantitation and HCV typing (melting curve) analysis using RT-PCR templates corresponding to HCV types 1a/b, 2a, 3a, 4a, 5a and 6a, each using a template concentration of $10^6$ copies per reaction. The template material for the RT-PCR reaction used RNA transcripts derived from in vitro transcription of a plasmids carrying subcloned HCV genomic material corresponding to the HCV types listed, and the RT-PCR amplification primers amplified a region within the 5'-UTR. The analysis used TaqMan quantitation probe ST650AAFBHQ2. The HCV typing melting curve analysis used the AG0308F HCV typing probe with new methylene blue soluble quencher. Fluorescence data is displayed as a first derivative plot as a function of cycle number. The results for each HCV type are overlaid on the same graph. A representative set of data is shown.

FIG. 22 provides a graph with the results of a "closed-tube" combined RT-PCR, HCV quantitation and HCV typing (melting curve) analysis using RT-PCR templates corresponding to HCV subtypes 1a/b, 2a, 3a, 4a, 5a and 6a, each using the same template concentration of $10^6$ copies per reaction. Data is shown in a first derivative plot as a function of cycle number. The RT-PCR reactions used HCV RNA templates, amplification primers ST280ATBUA1 (SEQ ID NO: 39) and ST778AATBA1 (SEQ ID NO: 40), and TaqMan probe ST650AAFBHQ2 (SEQ ID NO: 41), as described above. The genotyping melting curve analysis used the AG0308F HCV typing probe (SEQ ID NO: 16) with new methylene blue soluble quencher used at 25 μg/mL. The results of each subtype analysis are overlaid on the same graph, for a total of six plots.

Figure 23:
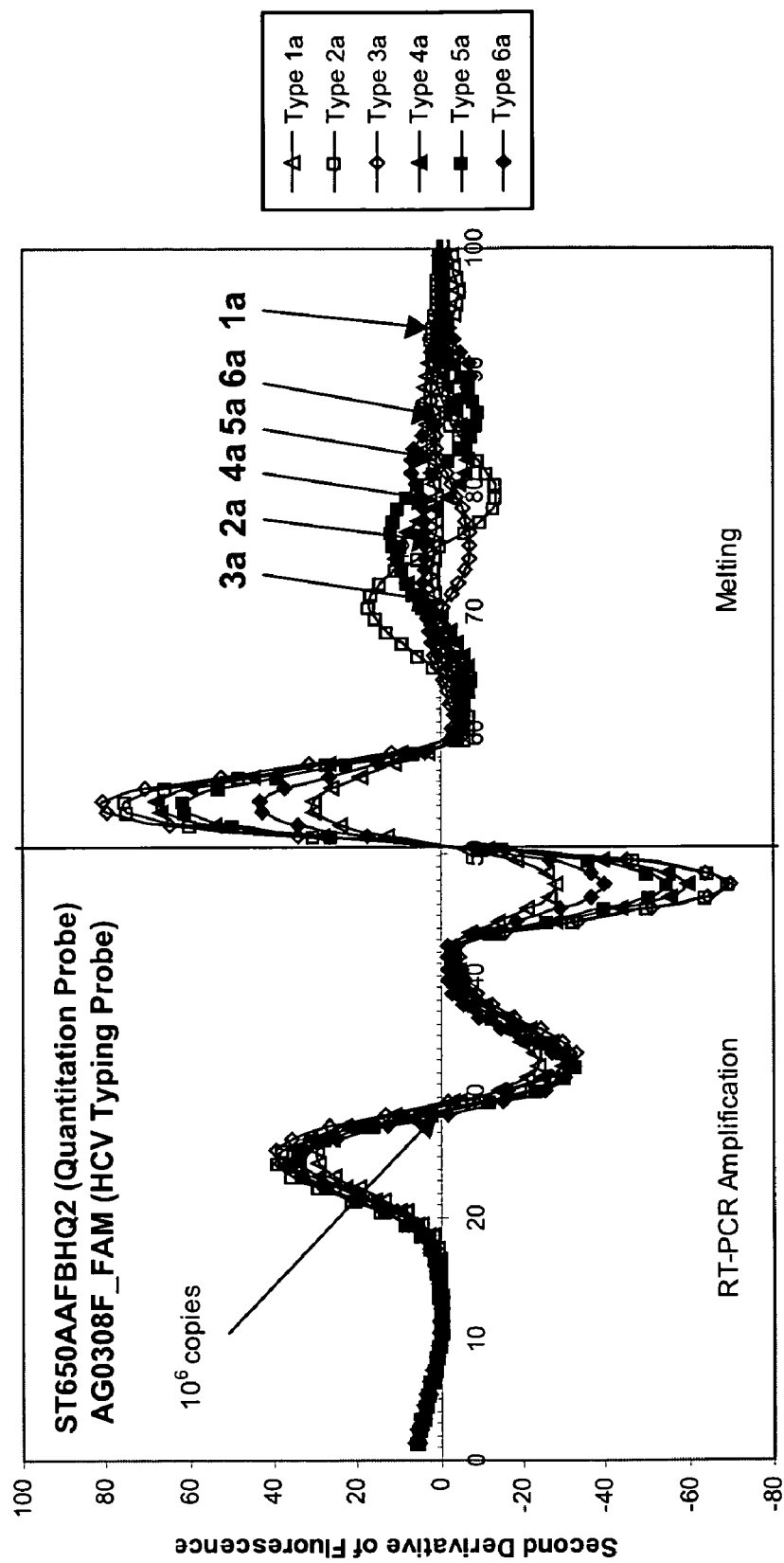
FIG. 23 provides a graph with the results of the closed-tube combined RT-PCR, HCV quantitation and HCV genotyping (melting curve) analysis described in FIG. 22, except using a second derivative plot. The $T_m$ of each hybridization complex can be determined by subtracting 26 from the cycle number.

FIG. 23 provides a graph with the results of the same closed-tube combined RT-PCR, HCV quantitation and HCV genotyping (melting curve) analysis described in FIG. 22 using a second derivative plot.

Figure 24:
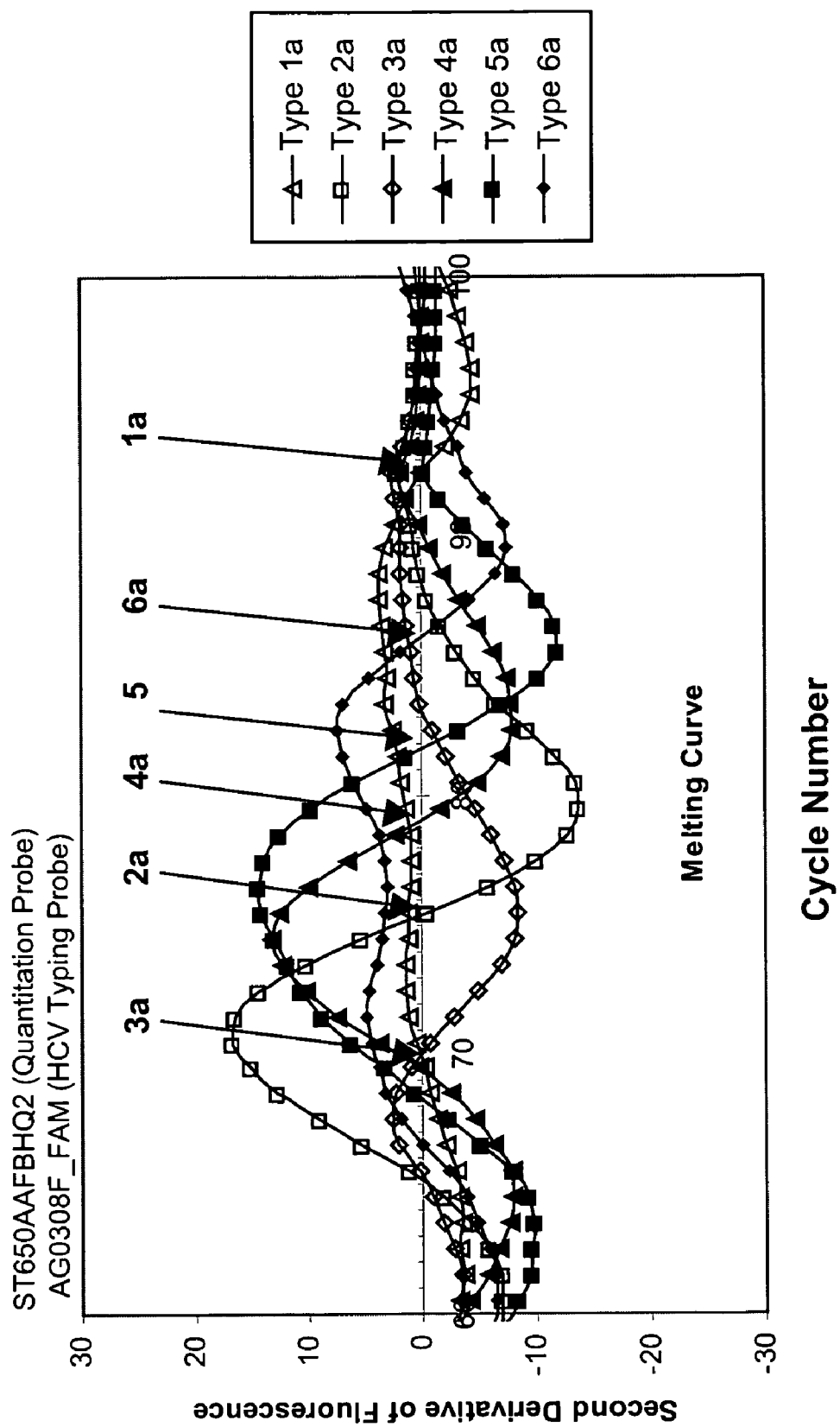
FIG. 24 provides a detailed view of the melting curve HCV typing portion of the graph shown in FIG. 23.

FIG. 24 provides a detailed view of the HCV typing melting curve portion of the graph shown in FIG. 23. The $T_m$ of each hybridization complex can be determined by subtracting 26 from the cycle number in the melting curve portion of the graph (after cycle number 50) at the point where the graph intersects zero on the y-axis. As can be seen in this expanded portion of the second derivative plot, each HCV type gives a clearly resolved $T_m$ value.

This same analysis was successfully repeated using ten other HCV typing probes (listed below) and the same reagents and thermal cycling conditions as described above.

| Probe | SEQ ID NO: |
|---|---|
| AG0308L | 17 |
| AG0308Q | 18 |
| AG0308R | 19 |
| AG0308T | 20 |
| AG0308U | 21 |

| Probe | SEQ ID NO: |
|---|---|
| AG0308V | 22 |
| AG0308W | 23 |
| AG0308X | 24 |
| AG0308Z | 26 |
| AG0308AB | 27 |

It was observed that these probes also were able to distinguish at least five HCV genotypes as well as at least six HCV subtypes in a closed-tube HCV quantitation and HCV typing analysis.

As can be seen in these experiments, it is possible to combine HCV quantitative analysis with HCV typing in a single closed-tube reaction system, where all necessary reagents for the RT-PCR, quantitative (TaqMan) analysis and HCV typing (melting analysis) are included in one reaction mixture that does not require modification (e.g., purification steps or additional components). Progression of these reactions is regulated by the thermal cycling conditions, and use of suitable reaction vessels allows the reading of fluorescence directly in the reaction vessel without removing sample aliquots.

Example 6

Nucleotide Sequences

This EXAMPLE provides nucleotide sequences recited in the description of the present invention. The sequences provided in TABLE 2 below is meant to provide examples only, and it is not intended that the invention be limited in any way to the sequences provided below in TABLE 2.

TABLE 2

| SEQ ID NO: | Description | SEQUENCE |
|---|---|---|
| 1 | HCV 5'-UTR consensus base sequence HCV Type 1a/1b/1c | TGAGTACACCGGAATTGCCAGGACGACCGGGTC |
| 2 | HCV 5'-UTR consensus base sequence HCV Type 2a/2c | TGAGTACACCGGAATTGCCGGGAAGACTGGGTC |
| 3 | HCV 5-UTR consensus base sequence HCV Type 2b | TGAGTACACCGGAATTACCGGAAAGACTGGGTC |
| 4 | HCV 5'-UTR consensus base sequence HCV Type 3a | TGAGTACACCGGAATCGCTGGGGTGACCGGGTC |
| 5 | HCV 5-UTR consensus base sequence HCV Type 4a | TGAGTACACCGGAATCGCCGGGATGACCGGGTC |
| 6 | HCV 5'-UTR consensus base sequence HCV Type 5a | TGAGTACACCGGAATTGCCGGGATGACCGGGTC |
| 7 | HCV 5'-UTR consensus base sequence HCV Type 6a | TGAGTACACCGGAATTGCCAGGATGACCGGGTC |
| 8 | HCV Typing Probe AG0203A | FCGGAATTGCCAGGACGACCGGP |
| 9 | HCV Typing Probe AG0303B | FJCGGAATTGCCAGGACGACCGG |

TABLE 2-continued

| SEQ ID NO: | Description | SEQUENCE |
|---|---|---|
| 10 | HCV Typing Probe AG0503D | FCACCGGAATTGCCAGGACGACCGG |
| 11 | HCV Typing Probe AG0503E | FCGGAATTGCCAGGACGACCGGG |
| 12 | HCV Typing Probe AG0503F | FCGGAATTGCCAGGACGACCGGGT |
| 13 | HCV Typing Probe AG0307D | FDGGAASSGDDAGGADGADDGGP |
| 14 | HCV Typing Probe AG0307M | FCGGAATTGCCAGGACGACCGGGP |
| 15 | HCV Typing Probe AG0307N | FDGGAASSGDDAGGADGADDGGGP |
| 16 | HCV Typing Probe AG0308F | FGTACACCGGAATTGCCAGGACGACCP |
| 17 | HCV Typing Probe AG0308L | FGTACACCGGAATTGCCAGGACGACP |
| 18 | HCV Typing Probe AG0308Q | FACACCGGAATTGCCAGGACGACCP |
| 19 | HCV Typing Probe AG0308R | FCACCGGAATTGCCAGGACGACCP |
| 20 | HCV Typing Probe AG0308T | FAGTACACCGGAATTGCCAGGACCACCP |
| 21 | HCV Typing Probe AG0308U | FGAGTACACCGGAATTGCCAGGACGACCP |
| 22 | HCV Typing Probe AG0308V | TGAGTACACCGGAATTGCCAGGACGACCP |
| 23 | HCV Typing Probe AG0308W | FGTACACCGGAATTGCCAGGACGACCGP |
| 24 | HCV Typing Probe AG0308X | FGTACACCGGAATTGCCAGGACGACCGGP |
| 25 | HCV Typing Probe AG0308Y | FGTACACCGGAATTGCCAGGACGACCGGGP |
| 26 | HCV Typing Probe AG0308Z | FAGTACACCGGAATTGCCAGGACGACCGP |
| 27 | HCV Typing Probe AG0308AB | FAGTACACCGGAATTGCCAGGACGACP |
| 28 | HCV Typing Probe AG0308M | FGTACACCGGAATTGCCAGGACGAP |
| 29 | HCV Typing Probe AG0308N | FGTACACCGGAATTGCCAGGACGP |
| 30 | HCV Typing Probe AG0308P | FTACACCGGAATTGCCAGGACGACCP |
| 31 | HCV Typing Probe AG0503G | FCGGAATTGCCAGGACGACCGGGTC |
| 32 | HCV Typing Probe AG0503H | FCCGGAATTGCCAGGACGACCGGG |
| 33 | HCV Type 1a/b Synthetic Template | AGGACCCGGTCGTCCTGGCAATTCCGGTGTA |
| 34 | HCV Type 2a/c Synthetic Template | AGGACCCAGTCTTCCCGGCAATTCCGGTGTA |
| 35 | HCV Type 3a Synthetic Template | AGGACCCGGTCACCCCAGCGATTCCGGTGTA |

TABLE 2-continued

| SEQ ID NO: | Description | SEQUENCE |
|---|---|---|
| 36 | HCV Type 4a Synthetic Template | AGGACCCGGTCATCCCGGCGATTCCGGTGTA |
| 37 | HCV Type 5a Synthetic Template | AGGACCCGGTCATCCCGGCAATTCCGGTGTA |
| 38 | HCV Type 6a Synthetic Template | AGGACCCGGTCATCCTGGCAATTCCGGTGTA |
| 39 | HCV Amplification Primer ST280ATBUA1 | GCAGAAAGCGTCTAGCCATGGCGTTB |
| 40 | HCV Amplification Primer ST778AATBA1 | GCAAGCACCCTATCAGGCAGTACCACAB |
| 41 | HCV TaqMan Quantitation Probe ST650AAFBHQ2 | FCGGTGTACTCACCGQTTCCGCAGACCACTATGP |
| 42 | HCV 5'-UTR base sequence HCV Type 2a variant | TGAGTACACCGGAATTGCTGGGAAGACTGGGTC |

F = 6-carboxy-fluorescein (FAM)
P = 3'-terminal phosphate group/enzymatically blocked
J = acridine
S = 5-propynyl-dU
D = 5-Me-dC
B = N6-t-butylbenzyl-dA
Q = BHQ-2

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A single-tube method for determining the type of a hepatitis C virus (HCV) and an HCV viral load in a sample, the method comprising:
   a) amplifying a portion of the HCV genome, from the sample via asymmetric PCR, thereby producing a limiting amplicon strand and an excess amplicon strand;
   b) hybridizing said limiting amplicon strand, with an amplicon quantitation probe and quantifying the amount of said limiting amplicon strand;
   c) hybridizing said excess amplicon strand, with a typing probe to form a target hybridization complex, wherein:
      i) said typing probe is complementary or partially complementary to a nucleotide sequence within an HCV genome;
      ii) said nucleotide sequence within an HCV genome shows sequence heterogeneity among at least five HCV genotypes or at least six HCV subtypes; and,
      iii) hybridization complexes comprising said typing probe and the at least five HCV genotypes or the at least six HCV subtypes have a distinguishing hybridization property that differentiates each of the HGV genotypes or HCV subtypes;
   d) measuring said distinguishing hybridization property of the target hybridization complex, and,
   e) correlating said measured distinguishing hybridization property of the target hybridization complex with a similar property of an HCV genotype or subtype wherein all the steps above are performed in a single tube.

2. The method of claim 1, wherein said typing probe comprises a FRET donor, a FRET quencher or both.

3. The method of claim 1, wherein said typing probe is a nucleotide oligomer comprising naturally-occurring nucleotides, modified nucleotides, nucleotide analogs, one or more unnatural bases, unnatural internucleotide linkages, unnatural nucleotide backbones, or any combination thereof.

4. The method of claim 1, wherein said arnplicon quantitation probe comprises a nucleotide sequence of SEQ ID NO: 41.

5. The method of claim 1, wherein said amplicon quantitation probe comprises a FRET donor moiety and a FRET quencher moiety wherein the amplicon quantitation probe forms a quantitation hybridization complex with the amplicon under conditions wherein base-pairing occurs.

6. The method of claim 5, wherein the amplifying step comprises detecting the donor moiety during the amplification step.

* * * * *

UNITED STATES PATENT AND TRADEMARK OFFICE
CERTIFICATE OF CORRECTION

PATENT NO. : 7,465,561 B2
APPLICATION NO. : 11/474125
DATED : December 16, 2008
INVENTOR(S) : Amar Gupta et al.

Page 1 of 1

It is certified that error appears in the above-identified patent and that said Letters Patent is hereby corrected as shown below:

Col. 79, line 22, claim 1 "HGV" should read --HCV--.

Signed and Sealed this

Twenty-fourth Day of March, 2009

JOHN DOLL
*Acting Director of the United States Patent and Trademark Office*